(12) United States Patent
Jin et al.

(10) Patent No.: US 10,767,164 B2
(45) Date of Patent: Sep. 8, 2020

(54) MICROENVIRONMENTS FOR SELF-ASSEMBLY OF ISLET ORGANOIDS FROM STEM CELLS DIFFERENTIATION

(71) Applicant: The Research Foundation for The State University of New York, Binghamton, NY (US)

(72) Inventors: Sha Jin, Vestal, NY (US); Kaiming Ye, Vestal, NY (US); Huanjing Bi, Binghamton, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 13 days.

(21) Appl. No.: 15/841,004

(22) Filed: Dec. 13, 2017

(65) Prior Publication Data

US 2018/0282699 A1    Oct. 4, 2018

Related U.S. Application Data

(60) Provisional application No. 62/479,095, filed on Mar. 30, 2017.

(51) Int. Cl.
| | |
|---|---|
| *C12N 5/071* | (2010.01) |
| *C12N 5/074* | (2010.01) |
| *C12N 5/0789* | (2010.01) |
| *A61L 27/14* | (2006.01) |
| *A61L 27/36* | (2006.01) |

(52) U.S. Cl.
CPC ............ *C12N 5/0677* (2013.01); *A61L 27/14* (2013.01); *A61L 27/3633* (2013.01); *A61L 27/3695* (2013.01); *C12N 5/0647* (2013.01); *C12N 5/0696* (2013.01); *A61L 2430/34* (2013.01); *C12N 2501/117* (2013.01); *C12N 2501/16* (2013.01); *C12N 2501/599* (2013.01); *C12N 2533/54* (2013.01); *C12N 2533/90* (2013.01)

(58) Field of Classification Search
CPC .................................................. C12N 5/0677
See application file for complete search history.

(56) References Cited

U.S. PATENT DOCUMENTS

| | | | |
|---|---|---|---|
| 5,429,938 A | 7/1995 | Humes | |
| 5,549,674 A | 8/1996 | Humes et al. | |
| 5,646,035 A | 7/1997 | Coon et al. | |
| 5,686,289 A | 11/1997 | Humes et al. | |
| 5,695,998 A | 12/1997 | Badylak et al. | |
| 5,747,341 A | 5/1998 | Brothers | |
| 5,780,299 A | 7/1998 | Coon et al. | |
| 5,780,300 A | 7/1998 | Artavanis-Tsakonas et al. | |
| 5,800,537 A | 9/1998 | Bell | |
| 5,821,121 A | 10/1998 | Brothers | |
| 5,849,584 A | 12/1998 | Coon et al. | |
| 5,861,313 A | 1/1999 | Pang et al. | |
| 5,866,414 A | 2/1999 | Badylak et al. | |
| 5,888,816 A | 3/1999 | Coon et al. | |
| 5,902,577 A | 5/1999 | Asfari et al. | |
| 5,928,942 A | 7/1999 | Brothers | |
| 6,008,047 A | 12/1999 | Curcio et al. | |
| 6,020,200 A | 2/2000 | Enevold | |
| 6,022,863 A | 2/2000 | Peyman | |
| 6,051,750 A | 4/2000 | Bell | |
| 6,060,270 A | 5/2000 | Humes | |
| 6,087,157 A | 7/2000 | Badylak et al. | |
| 6,149,902 A | 11/2000 | Artavanis-Tsakonas et al. | |
| 6,197,575 B1 | 3/2001 | Griffith et al. | |
| 6,326,201 B1 | 12/2001 | Fung et al. | |
| 6,372,493 B1 | 4/2002 | Brothers | |
| 6,398,819 B1 | 6/2002 | Bell | |
| 6,410,320 B1 | 6/2002 | Humes | |
| 6,413,735 B1 | 7/2002 | Lau | |
| 6,455,311 B1 | 9/2002 | Vacanti | |
| 6,485,723 B1 | 11/2002 | Badylak et al. | |

(Continued)

OTHER PUBLICATIONS

Meezan et al., 1975, Life Sciences, vol. 17, pp. 1721-1732 (Year: 1975).*

(Continued)

*Primary Examiner* — Thaian N. Ton
*Assistant Examiner* — David A. Montanari
(74) *Attorney, Agent, or Firm* — Hoffberg & Associates; Steven M. Hoffberg

(57) ABSTRACT

Human pluripotent stem cells (hPSCs) are promising cell source to produce therapeutic endocrine cells for diabetes treatment. A gel solution made by decellularized tissue-specific extracellular matrix (dpECM) significantly promotes three-dimensional (3D) islet-like organogenesis during induced hPSC differentiation into endocrine lineages. Islet organoids are self-organized even in a two-dimensional (2D) culture mode. Cells derived from hPSCs differentiated on such ECM coated substrates exhibit similar cellular composition to native pancreatic islets. These cells express islet signature markers insulin, PDX-1, C-peptide, MafA, glucagon, somatostatin, and pancreatic polypeptide, and secrete more insulin in response to glucose level compared to a traditional matrix substrate (Matrigel). The dpECM facilitates generating more C-peptide+/glucagon− cells rather than C-peptide+/glucagon+ cells. Remarkably, dpECM also facilitated intra-organoid vascularity by generating endothelial cells and pericytes. Furthermore, dpECM niches also induced intra-organoid microvascularization during pancreatic differentiation.

8 Claims, 32 Drawing Sheets

Specification includes a Sequence Listing.

(56) References Cited

U.S. PATENT DOCUMENTS

| | | |
|---|---|---|
| 6,541,224 B2 | 4/2003 | Yu et al. |
| 6,552,016 B1 | 4/2003 | Baxter et al. |
| 6,610,535 B1 | 8/2003 | Lu et al. |
| 6,623,941 B1 | 9/2003 | Ruben et al. |
| 6,759,039 B2 | 7/2004 | Tsang et al. |
| 6,821,484 B1 | 11/2004 | Gregersen |
| 6,878,806 B2 | 4/2005 | Ruben et al. |
| 6,900,051 B2 | 5/2005 | Kerr-Conte et al. |
| 6,902,881 B2 | 6/2005 | Falchuk |
| 6,905,688 B2 | 6/2005 | Rosen et al. |
| 6,908,732 B2 | 6/2005 | Falchuk |
| 6,919,433 B2 | 7/2005 | Ruben et al. |
| 6,926,898 B2 | 8/2005 | Rosen et al. |
| 6,946,134 B1 | 9/2005 | Rosen et al. |
| 6,946,293 B1 | 9/2005 | Lu et al. |
| 6,951,924 B2 | 10/2005 | Rosen et al. |
| 6,962,814 B2 | 11/2005 | Mitchell et al. |
| 6,969,519 B2 | 11/2005 | Ruben et al. |
| 7,015,037 B1 | 3/2006 | Furcht et al. |
| 7,026,447 B2 | 4/2006 | Rosen et al. |
| 7,064,185 B2 | 6/2006 | Lau |
| 7,101,546 B2 | 9/2006 | Tsang et al. |
| 7,112,410 B1 | 9/2006 | Ruben et al. |
| 7,135,336 B1 | 11/2006 | Paylian |
| 7,141,547 B2 | 11/2006 | Rosen et al. |
| 7,164,004 B2 | 1/2007 | Ruben et al. |
| 7,175,841 B2 | 2/2007 | Badylak et al. |
| 7,189,690 B2 | 3/2007 | Rosen et al. |
| 7,196,164 B2 | 3/2007 | Rosen et al. |
| 7,211,434 B2 | 5/2007 | Van Der Kooy et al. |
| 7,217,570 B2 | 5/2007 | Herlyn et al. |
| 7,217,788 B2 | 5/2007 | Yu et al. |
| 7,238,660 B2 | 7/2007 | Rosen et al. |
| 7,238,667 B2 | 7/2007 | Rosen et al. |
| 7,244,707 B2 | 7/2007 | Roberts et al. |
| 7,247,477 B2 | 7/2007 | Itskovitz-Eldor et al. |
| 7,300,929 B2 | 11/2007 | Baxter et al. |
| 7,301,016 B2 | 11/2007 | Meyers et al. |
| 7,312,241 B2 | 12/2007 | Muller et al. |
| 7,326,570 B2 | 2/2008 | Nigam et al. |
| 7,351,729 B2 | 4/2008 | Stein et al. |
| 7,354,763 B2 | 4/2008 | Gerecht-Nir et al. |
| 7,355,008 B2 | 4/2008 | Stavenhagen et al. |
| 7,368,527 B2 | 5/2008 | Rosen et al. |
| 7,368,531 B2 | 5/2008 | Rosen et al. |
| 7,371,388 B1 | 5/2008 | Ruben et al. |
| 7,371,576 B2 | 5/2008 | Tsang et al. |
| 7,381,800 B2 | 6/2008 | Shi et al. |
| 7,390,637 B2 | 6/2008 | LaFleur et al. |
| 7,396,809 B1 | 7/2008 | Lu et al. |
| 7,413,897 B2 | 8/2008 | Reid et al. |
| 7,416,885 B2 | 8/2008 | Freeman et al. |
| 7,425,619 B2 | 9/2008 | Koenig et al. |
| 7,425,620 B2 | 9/2008 | Koenig et al. |
| 7,452,964 B2 | 11/2008 | Pasqualini et al. |
| 7,468,446 B2 | 12/2008 | Muller et al. |
| 7,469,185 B2 | 12/2008 | Mendrick et al. |
| 7,470,723 B2 | 12/2008 | Muller et al. |
| 7,482,013 B2 | 1/2009 | Ballance et al. |
| 7,485,297 B2 | 2/2009 | Wood et al. |
| 7,497,686 B2 | 3/2009 | Sharpe et al. |
| 7,498,027 B2 | 3/2009 | Ruben et al. |
| 7,498,168 B2 | 3/2009 | Sharpe |
| 7,501,123 B2 | 3/2009 | Roschke et al. |
| 7,507,413 B2 | 3/2009 | Rosen et al. |
| 7,507,414 B2 | 3/2009 | Rosen et al. |
| 7,510,873 B2 | 3/2009 | Mistry et al. |
| 7,521,424 B2 | 4/2009 | Rosen et al. |
| 7,521,540 B2 | 4/2009 | Lau et al. |
| 7,521,542 B2 | 4/2009 | Johnson et al. |
| 7,534,608 B2 | 5/2009 | Martinson et al. |
| 7,560,276 B2 | 7/2009 | Harmon et al. |
| 7,563,619 B2 | 7/2009 | Williams et al. |
| 7,569,384 B2 | 8/2009 | Rosen et al. |
| 7,582,292 B2 | 9/2009 | Wilkison et al. |
| 7,588,936 B2 | 9/2009 | Sharpe |
| 7,592,010 B2 | 9/2009 | Rosen et al. |
| 7,601,525 B2 | 10/2009 | Batich et al. |
| 7,604,991 B2 | 10/2009 | Bouwens et al. |
| 7,615,373 B2 | 11/2009 | Simpson et al. |
| 7,632,497 B2 | 12/2009 | Stavenhagen |
| 7,632,679 B2 | 12/2009 | Jessell et al. |
| 7,648,964 B2 | 1/2010 | Laurie et al. |
| 7,655,674 B2 | 2/2010 | Beachy et al. |
| 7,659,118 B2 | 2/2010 | Furcht et al. |
| 7,670,797 B2 | 3/2010 | Vacanti et al. |
| 7,695,965 B2 | 4/2010 | Martinson et al. |
| 7,723,112 B2 | 5/2010 | Clarke et al. |
| 7,745,216 B2 | 6/2010 | Pang et al. |
| 7,754,483 B2 | 7/2010 | Salli et al. |
| 7,759,113 B2 | 7/2010 | Vacanti et al. |
| 7,771,717 B2 | 8/2010 | Badylak et al. |
| 7,776,592 B2 | 8/2010 | Wandinger-Ness et al. |
| 7,776,597 B2 | 8/2010 | Deng et al. |
| 7,781,179 B2 | 8/2010 | Weissman et al. |
| 7,785,599 B2 | 8/2010 | Ballance et al. |
| 7,799,759 B2 | 9/2010 | Rosen et al. |
| 7,799,898 B2 | 9/2010 | Meyers |
| 7,803,377 B2 | 9/2010 | Yan et al. |
| 7,807,459 B2 | 10/2010 | Tsang et al. |
| 7,807,641 B2 | 10/2010 | Pang et al. |
| 7,811,819 B2 | 10/2010 | Ware et al. |
| 7,838,503 B2 | 11/2010 | Alt et al. |
| 7,838,636 B1 | 11/2010 | Ruben et al. |
| 7,847,079 B2 | 12/2010 | Rosen et al. |
| 7,875,272 B2 | 1/2011 | Messina et al. |
| 7,883,847 B2 | 2/2011 | Hipp et al. |
| 7,883,892 B2 | 2/2011 | Verfaillie et al. |
| 7,910,555 B2 | 3/2011 | Harding et al. |
| 7,914,779 B2 | 3/2011 | Hariri |
| 7,939,322 B2 | 5/2011 | Rezania |
| 7,951,362 B2 | 5/2011 | Pasqualini et al. |
| 7,960,512 B2 | 6/2011 | Stavenhagen et al. |
| 7,977,306 B2 | 7/2011 | Rosen et al. |
| 7,985,537 B2 | 7/2011 | Zheng et al. |
| 7,993,920 B2 | 8/2011 | Martinson et al. |
| 8,003,774 B2 | 8/2011 | Stavenhagen et al. |
| 8,008,075 B2 | 8/2011 | Green et al. |
| 8,012,464 B2 | 9/2011 | Rosen et al. |
| 8,022,178 B2 | 9/2011 | Horii et al. |
| 8,030,025 B2 | 10/2011 | Boone et al. |
| 8,044,180 B2 | 10/2011 | Koenig et al. |
| 8,053,456 B2 | 11/2011 | Sun et al. |
| 8,067,377 B2 | 11/2011 | Arap et al. |
| 8,071,539 B2 | 12/2011 | Rosen et al. |
| 8,075,881 B2 | 12/2011 | Verfaillie et al. |
| 8,084,258 B2 | 12/2011 | Gehring et al. |
| 8,092,102 B2 | 1/2012 | Shangguan et al. |
| 8,106,083 B2 | 1/2012 | Burlison et al. |
| 8,110,400 B2 | 2/2012 | De Sousa |
| 8,129,182 B2 | 3/2012 | D'Amour et al. |
| 8,133,982 B2 | 3/2012 | Johnson et al. |
| 8,137,662 B2 | 3/2012 | Freeman et al. |
| 8,143,026 B2 | 3/2012 | Rosen et al. |
| 8,147,824 B2 | 4/2012 | Maziarz et al. |
| 8,148,149 B2 | 4/2012 | Nigam et al. |
| 8,173,361 B2 | 5/2012 | Vacanti et al. |
| 8,183,384 B2 | 5/2012 | Chimmanamada et al. |
| 8,187,593 B2 | 5/2012 | Koenig et al. |
| 8,187,878 B2 | 5/2012 | Dalton et al. |
| 8,192,737 B2 | 6/2012 | Stavenhagen et al. |
| 8,193,318 B2 | 6/2012 | Koenig et al. |
| 8,197,815 B2 | 6/2012 | Wu et al. |
| 8,198,255 B2 | 6/2012 | Houchen et al. |
| 8,211,439 B2 | 7/2012 | Rosen et al. |
| 8,211,697 B2 | 7/2012 | Sakurada et al. |
| 8,211,867 B2 | 7/2012 | Bennett et al. |
| 8,216,574 B2 | 7/2012 | Stavenhagen et al. |
| 8,217,147 B2 | 7/2012 | Stavenhagen et al. |
| 8,221,749 B2 | 7/2012 | Boone et al. |
| 8,222,253 B2 | 7/2012 | Wang et al. |
| 8,236,761 B2 | 8/2012 | Harding et al. |
| 8,247,423 B2 | 8/2012 | Estok et al. |
| 8,252,280 B1 | 8/2012 | Verfaillie et al. |

(56) References Cited

U.S. PATENT DOCUMENTS

| | | |
|---|---|---|
| 8,252,739 B2 | 8/2012 | Rosen et al. |
| 8,252,764 B2 | 8/2012 | Pasqualini et al. |
| 8,252,915 B2 | 8/2012 | Meyers et al. |
| 8,273,570 B2 | 9/2012 | Sasai et al. |
| 8,278,095 B2 | 10/2012 | Clarke et al. |
| 8,287,859 B2 | 10/2012 | Rosen et al. |
| 8,299,107 B2 | 10/2012 | Chimmanamada et al. |
| 8,299,212 B2 | 10/2012 | Carlson et al. |
| 8,303,972 B2 | 11/2012 | Michal |
| 8,318,483 B2 | 11/2012 | Mistry et al. |
| 8,318,790 B2 | 11/2012 | Ying et al. |
| RE43,876 E | 12/2012 | Rezania |
| 8,329,467 B2 | 12/2012 | Zaret et al. |
| 8,329,736 B2 | 12/2012 | Chimmanamada et al. |
| 8,334,365 B2 | 12/2012 | Rosen et al. |
| 8,337,829 B2 | 12/2012 | Freeman et al. |
| 8,354,397 B2 | 1/2013 | Rubin et al. |
| 8,357,528 B2 | 1/2013 | Vacanti et al. |
| 8,357,690 B2 | 1/2013 | Armstrong et al. |
| 8,361,459 B2 | 1/2013 | Messina et al. |
| 8,377,689 B2 | 2/2013 | Tsang et al. |
| 8,404,242 B2 | 3/2013 | Zhou et al. |
| 8,409,859 B2 | 4/2013 | Verfaillie et al. |
| 8,410,246 B2 | 4/2013 | Carlson et al. |
| 8,415,153 B2 | 4/2013 | Majumdar et al. |
| 8,415,377 B2 | 4/2013 | Sun et al. |
| 8,445,273 B2 | 5/2013 | Green et al. |
| 8,445,645 B2 | 5/2013 | Stavenhagen et al. |
| 8,450,500 B2 | 5/2013 | Chimmanamada et al. |
| 8,460,864 B2 | 6/2013 | Cao et al. |
| 8,460,929 B2 | 6/2013 | Nigam et al. |
| 8,470,308 B2 | 6/2013 | Wasielewski |
| 8,470,309 B2 | 6/2013 | Wasielewski |
| 8,470,599 B2 | 6/2013 | Dressler et al. |
| 8,481,308 B2 | 7/2013 | Stern et al. |
| 8,486,932 B2 | 7/2013 | Burlison et al. |
| 8,513,189 B2 | 8/2013 | Rosen et al. |
| 8,518,390 B2 | 8/2013 | Kramer et al. |
| 8,524,712 B2 | 9/2013 | Lee et al. |
| 8,530,627 B2 | 9/2013 | Koenig et al. |
| 8,540,978 B2 | 9/2013 | Wasielewski |
| 8,551,779 B2 | 10/2013 | Hald et al. |
| 8,562,969 B2 | 10/2013 | Wasielewski |
| 8,586,345 B2 | 11/2013 | Simpson et al. |
| 8,596,607 B2 | 12/2013 | Maercovich |
| 8,603,811 B2 | 12/2013 | D'Amour et al. |
| 8,609,406 B2 | 12/2013 | Subramanian et al. |
| 8,623,648 B2 | 1/2014 | Davis et al. |
| 8,642,336 B2 | 2/2014 | Vacanti et al. |
| 8,642,339 B2 | 2/2014 | Sato et al. |
| 8,648,071 B2 | 2/2014 | Burlison et al. |
| 8,652,466 B2 | 2/2014 | Stavenhagen et al. |
| 8,680,067 B2 | 3/2014 | Bennett et al. |
| 8,685,390 B2 | 4/2014 | Emig et al. |
| 8,685,720 B2 | 4/2014 | Weiss et al. |
| 8,685,730 B2 | 4/2014 | Odorico et al. |
| 8,691,523 B2 | 4/2014 | Reid et al. |
| 8,697,071 B2 | 4/2014 | Stavenhagen et al. |
| 8,703,121 B2 | 4/2014 | Harris et al. |
| 8,703,424 B2 | 4/2014 | West et al. |
| 8,703,483 B2 | 4/2014 | Cezar |
| 8,709,402 B2 | 4/2014 | Emig et al. |
| 8,710,017 B2 | 4/2014 | Arap et al. |
| 8,716,465 B2 | 5/2014 | Rossi et al. |
| 8,722,034 B2 | 5/2014 | Kihm et al. |
| 8,728,813 B2 | 5/2014 | Efrat et al. |
| 8,735,154 B2 | 5/2014 | Berkland et al. |
| 8,741,643 B2 | 6/2014 | Rezania et al. |
| 8,741,646 B2 | 6/2014 | Emig et al. |
| 8,742,133 B2 | 6/2014 | Ying et al. |
| 8,748,171 B2 | 6/2014 | Keller et al. |
| 8,748,424 B2 | 6/2014 | Chimmanamada et al. |
| 8,753,638 B2 | 6/2014 | Zhou et al. |
| 8,765,390 B2 | 7/2014 | Ailles et al. |
| 8,765,470 B2 | 7/2014 | Thomson et al. |
| 8,772,275 B2 | 7/2014 | Rubin et al. |
| 8,778,899 B2 | 7/2014 | Ferber |
| 8,784,772 B2 | 7/2014 | Berman et al. |
| 8,784,808 B2 | 7/2014 | Johnson et al. |
| 8,785,184 B2 | 7/2014 | Xu |
| 8,785,185 B2 | 7/2014 | Xu et al. |
| 8,785,599 B2 | 7/2014 | Johnson et al. |
| 8,785,658 B2 | 7/2014 | Chimmanamada et al. |
| 8,802,438 B2 | 8/2014 | Rossi et al. |
| 8,815,584 B1 | 8/2014 | Hickman et al. |
| 8,815,587 B2 | 8/2014 | Harris et al. |
| 8,815,591 B2 | 8/2014 | Keller et al. |
| 8,822,684 B1 | 9/2014 | Hong et al. |
| 8,828,433 B2 | 9/2014 | Claude et al. |
| 8,828,685 B2 | 9/2014 | Schimmel et al. |
| 8,828,721 B1 | 9/2014 | Hickman et al. |
| 8,835,168 B2 | 9/2014 | Hickman et al. |
| 8,835,464 B2 | 9/2014 | Sun et al. |
| 8,836,218 B2 | 9/2014 | Armstrong et al. |
| 8,841,123 B2 | 9/2014 | Stern et al. |
| 8,846,859 B2 | 9/2014 | Pasqualini et al. |
| 8,852,934 B2 | 10/2014 | Kanamune et al. |
| 8,853,162 B2 | 10/2014 | Kurisawa et al. |
| 8,859,286 B2 | 10/2014 | Agulnick |
| 8,877,181 B2 | 11/2014 | Emig et al. |
| 8,877,497 B2 | 11/2014 | Ruiz et al. |
| 8,883,160 B2 | 11/2014 | Chang et al. |
| 8,883,506 B2 | 11/2014 | Rossi et al. |
| 8,895,048 B2 | 11/2014 | Stehno-Bittel et al. |
| 8,895,300 B2 | 11/2014 | Schulz |
| 8,906,360 B2 | 12/2014 | Deisseroth et al. |
| 8,911,690 B2 | 12/2014 | Kugelmeier et al. |
| 8,911,953 B2 | 12/2014 | Carlson et al. |
| 8,916,686 B2 | 12/2014 | Carlson et al. |
| 8,927,548 B2 | 1/2015 | Ying et al. |
| 8,937,094 B2 | 1/2015 | Burlison et al. |
| 8,940,292 B2 | 1/2015 | Atala et al. |
| 8,946,156 B2 | 2/2015 | Ballance et al. |
| 8,946,387 B2 | 2/2015 | Koenig et al. |
| 8,951,517 B2 | 2/2015 | Stavenhagen et al. |
| 8,968,730 B2 | 3/2015 | Koenig et al. |
| 8,969,301 B2 | 3/2015 | Greene et al. |
| 8,969,538 B2 | 3/2015 | Rosen et al. |
| 8,993,517 B2 | 3/2015 | Rosen et al. |
| 9,005,897 B2 | 4/2015 | Lim et al. |
| 9,005,962 B2 | 4/2015 | Morrison et al. |
| 9,005,964 B2 | 4/2015 | Verfaillie et al. |
| 9,006,277 B2 | 4/2015 | Sun et al. |
| 9,012,218 B2 | 4/2015 | Rezania |
| 9,018,005 B2 | 4/2015 | Lim et al. |
| 9,028,815 B2 | 5/2015 | Stavenhagen et al. |
| 9,029,147 B2 | 5/2015 | Colton et al. |
| 9,040,694 B1 | 5/2015 | Hong et al. |
| 9,056,093 B2 | 6/2015 | Atala et al. |
| 9,062,290 B2 | 6/2015 | Rezania |
| 9,062,346 B2 | 6/2015 | Hipp et al. |
| 9,066,930 B2 | 6/2015 | Yan et al. |
| 9,067,884 B2 | 6/2015 | Chimmanamada et al. |
| 9,068,169 B2 | 6/2015 | Tsang et al. |
| 9,080,145 B2 | 7/2015 | Nelson |
| 9,085,756 B2 | 7/2015 | Fisk et al. |
| 9,096,832 B2 | 8/2015 | Xu |
| 9,096,877 B2 | 8/2015 | Johnson et al. |
| 9,101,690 B2 | 8/2015 | Deisseroth et al. |
| 9,115,191 B2 | 8/2015 | Wu et al. |
| 9,120,745 B2 | 9/2015 | Ying et al. |
| 9,125,906 B2 | 9/2015 | Buensuceso et al. |
| 9,126,953 B2 | 9/2015 | Ying et al. |
| 9,127,268 B2 | 9/2015 | Watkins et al. |
| 9,133,439 B2 | 9/2015 | Davis et al. |
| 9,150,833 B2 | 10/2015 | Xu |
| 9,150,857 B2 | 10/2015 | Bennett et al. |
| 9,151,744 B2 | 10/2015 | Pongracz et al. |
| 9,151,760 B2 | 10/2015 | Weissman et al. |
| 9,156,836 B2 | 10/2015 | Burlison et al. |
| 9,157,069 B2 | 10/2015 | Hosoya et al. |
| 9,163,216 B1 | 10/2015 | Hickman et al. |
| 9,173,869 B2 | 11/2015 | Guicherit et al. |
| 9,175,089 B2 | 11/2015 | Hongo et al. |

(56) References Cited

U.S. PATENT DOCUMENTS

| | | |
|---|---|---|
| 9,181,301 B2 | 11/2015 | Carlson et al. |
| 9,181,528 B2 | 11/2015 | Rezania |
| 9,186,388 B2 | 11/2015 | Deb |
| 9,206,162 B2 | 12/2015 | Sun et al. |
| 9,221,896 B2 | 12/2015 | Rosen et al. |
| 9,234,176 B2 | 1/2016 | Wu et al. |
| 9,234,178 B2 | 1/2016 | Rezania et al. |
| 9,267,936 B2 | 2/2016 | Hickman et al. |
| 9,267,938 B2 | 2/2016 | Lee et al. |
| 9,278,159 B2 | 3/2016 | Deisseroth et al. |
| 9,284,531 B2 | 3/2016 | Stachelscheid et al. |
| 9,289,453 B2 | 3/2016 | Bloch et al. |
| 9,296,809 B2 | 3/2016 | Rosen et al. |
| 9,308,238 B2 | 4/2016 | Scheel et al. |
| 9,315,794 B2 | 4/2016 | Greene et al. |
| 9,328,340 B2 | 5/2016 | Watkins et al. |
| 9,365,830 B2 | 6/2016 | Schulz et al. |
| 9,365,851 B2 | 6/2016 | Chai et al. |
| 9,371,516 B2 | 6/2016 | Xu et al. |
| 9,388,381 B2 | 7/2016 | Colton et al. |
| 9,388,387 B2 | 7/2016 | Rezania |
| 9,394,522 B2 | 7/2016 | Brolen et al. |
| 9,404,087 B2 | 8/2016 | Revel et al. |
| 9,404,140 B1 | 8/2016 | Molnar et al. |
| 9,409,995 B2 | 8/2016 | Foord et al. |
| 9,415,086 B2 | 8/2016 | Wang et al. |
| 9,434,920 B2 | 9/2016 | Rezania |
| 9,447,378 B2 | 9/2016 | Colton et al. |
| 9,447,380 B2 | 9/2016 | Subramanian et al. |
| 9,453,205 B2 | 9/2016 | Ahlfors et al. |
| 9,458,430 B2 | 10/2016 | Rezania |
| 9,458,471 B2 | 10/2016 | Weiss et al. |
| 9,476,030 B2 | 10/2016 | Gadue et al. |
| 9,481,894 B2 | 11/2016 | Ferber |
| 9,487,750 B2 | 11/2016 | Smith et al. |
| 9,489,474 B2 | 11/2016 | Hickman et al. |
| 9,493,845 B2 | 11/2016 | Cao et al. |
| 9,498,501 B2 | 11/2016 | Mistry et al. |
| 9,499,789 B2 | 11/2016 | Nakahata et al. |
| 9,499,793 B2 | 11/2016 | Hornstein et al. |
| 9,504,719 B2 | 11/2016 | Brown et al. |
| 9,506,036 B2 | 11/2016 | Fryer |
| 9,506,062 B2 | 11/2016 | Bennett et al. |
| 9,526,747 B2 | 12/2016 | Verfaillie et al. |
| 9,527,912 B2 | 12/2016 | Pearl et al. |
| 9,528,090 B2 | 12/2016 | Rezania |
| 9,534,203 B2 | 1/2017 | Atala et al. |
| 9,539,243 B2 | 1/2017 | Burlison et al. |
| 9,540,613 B2 | 1/2017 | Odorico et al. |
| 9,540,628 B2 | 1/2017 | Watkins et al. |
| 9,546,379 B2 | 1/2017 | Evans et al. |
| 9,550,838 B2 | 1/2017 | Chang et al. |
| 9,555,007 B2 | 1/2017 | Ma et al. |
| 9,579,351 B2 | 2/2017 | Kihm et al. |
| 9,580,688 B2 | 2/2017 | Atala et al. |
| 9,585,917 B2 | 3/2017 | Martinson et al. |
| 9,585,918 B2 | 3/2017 | Buensuceso et al. |
| 9,592,256 B2 | 3/2017 | Christman et al. |
| 9,592,258 B2 | 3/2017 | Seyda et al. |
| 9,593,305 B2 | 3/2017 | Davis et al. |
| 9,593,306 B2 | 3/2017 | Davis et al. |
| 9,593,307 B2 | 3/2017 | Rezania |
| 9,605,244 B2 | 3/2017 | Ruiz et al. |
| 9,605,265 B2 | 3/2017 | Zhou et al. |
| 9,951,000 B2 | 4/2018 | Peng et al. |
| 2001/0000324 A1 | 4/2001 | Todorov et al. |
| 2002/0006640 A1 | 1/2002 | Ni et al. |
| 2002/0012653 A1 | 1/2002 | Pang et al. |
| 2002/0012966 A1 | 1/2002 | Shi et al. |
| 2002/0042096 A1 | 4/2002 | Rosen et al. |
| 2002/0042386 A1 | 4/2002 | Rosen et al. |
| 2002/0045230 A1 | 4/2002 | Rosen et al. |
| 2002/0061521 A1 | 5/2002 | Rosen et al. |
| 2002/0064818 A1 | 5/2002 | Ni et al. |
| 2002/0064829 A1 | 5/2002 | Yu et al. |
| 2002/0076756 A1 | 6/2002 | Ruben et al. |
| 2002/0077270 A1 | 6/2002 | Rosen et al. |
| 2002/0077287 A1 | 6/2002 | Ruben et al. |
| 2002/0081725 A1 | 6/2002 | Tsang et al. |
| 2002/0086330 A1 | 7/2002 | Rosen et al. |
| 2002/0086353 A1 | 7/2002 | Rosen et al. |
| 2002/0086811 A1 | 7/2002 | Rosen et al. |
| 2002/0086820 A1 | 7/2002 | Rosen et al. |
| 2002/0086821 A1 | 7/2002 | Rosen et al. |
| 2002/0086822 A1 | 7/2002 | Rosen et al. |
| 2002/0086823 A1 | 7/2002 | Rosen et al. |
| 2002/0090615 A1 | 7/2002 | Rosen et al. |
| 2002/0090672 A1 | 7/2002 | Rosen et al. |
| 2002/0090673 A1 | 7/2002 | Rosen et al. |
| 2002/0090674 A1 | 7/2002 | Rosen et al. |
| 2002/0094953 A1 | 7/2002 | Rosen et al. |
| 2002/0099085 A1 | 7/2002 | Falchuk |
| 2002/0102638 A1 | 8/2002 | Rosen et al. |
| 2002/0106736 A1 | 8/2002 | Ruben et al. |
| 2002/0119566 A1 | 8/2002 | Humes |
| 2002/0119919 A1 | 8/2002 | Rosen et al. |
| 2002/0120103 A1 | 8/2002 | Rosen et al. |
| 2002/0132753 A1 | 9/2002 | Rosen et al. |
| 2002/0132767 A1 | 9/2002 | Rosen et al. |
| 2002/0147140 A1 | 10/2002 | Rosen et al. |
| 2002/0150986 A1 | 10/2002 | Lau |
| 2002/0151056 A1 | 10/2002 | Sasai et al. |
| 2002/0151479 A1 | 10/2002 | Rosen et al. |
| 2002/0155598 A1 | 10/2002 | Kerr-Conte et al. |
| 2002/0161208 A1 | 10/2002 | Rosen et al. |
| 2002/0164685 A1 | 11/2002 | Rosen et al. |
| 2002/0164791 A1 | 11/2002 | Van Der Kooy et al. |
| 2002/0165137 A1 | 11/2002 | Ruben et al. |
| 2002/0165221 A1 | 11/2002 | Baxter et al. |
| 2002/0168711 A1 | 11/2002 | Rosen et al. |
| 2002/0172994 A1 | 11/2002 | Ruben et al. |
| 2002/0173454 A1 | 11/2002 | Rosen et al. |
| 2003/0003088 A1 | 1/2003 | Tsao et al. |
| 2003/0013649 A1 | 1/2003 | Rosen et al. |
| 2003/0027330 A1 | 2/2003 | Lanza et al. |
| 2003/0027776 A1 | 2/2003 | Roschke |
| 2003/0027999 A1 | 2/2003 | Rosen et al. |
| 2003/0036505 A1 | 2/2003 | Barash et al. |
| 2003/0039993 A1 | 2/2003 | Rosen et al. |
| 2003/0039994 A1 | 2/2003 | Rosen et al. |
| 2003/0044890 A1 | 3/2003 | Rosen et al. |
| 2003/0044904 A1 | 3/2003 | Rosen et al. |
| 2003/0044905 A1 | 3/2003 | Rosen et al. |
| 2003/0044907 A1 | 3/2003 | Rosen et al. |
| 2003/0044976 A1 | 3/2003 | Dominko et al. |
| 2003/0045459 A1 | 3/2003 | Ruben et al. |
| 2003/0049618 A1 | 3/2003 | Ruben et al. |
| 2003/0049650 A1 | 3/2003 | Rosen et al. |
| 2003/0049652 A1 | 3/2003 | Rosen et al. |
| 2003/0049703 A1 | 3/2003 | Rosen et al. |
| 2003/0050231 A1 | 3/2003 | Rosen et al. |
| 2003/0050455 A1 | 3/2003 | Ruben et al. |
| 2003/0054368 A1 | 3/2003 | Rosen et al. |
| 2003/0054373 A1 | 3/2003 | Rosen et al. |
| 2003/0054375 A1 | 3/2003 | Rosen et al. |
| 2003/0054377 A1 | 3/2003 | Rosen et al. |
| 2003/0054379 A1 | 3/2003 | Rosen et al. |
| 2003/0054420 A1 | 3/2003 | Rosen et al. |
| 2003/0059875 A1 | 3/2003 | Rosen et al. |
| 2003/0059908 A1 | 3/2003 | Rosen et al. |
| 2003/0068627 A1 | 4/2003 | Rosen et al. |
| 2003/0077602 A1 | 4/2003 | Rosen et al. |
| 2003/0077606 A1 | 4/2003 | Rosen et al. |
| 2003/0077703 A1 | 4/2003 | Rosen et al. |
| 2003/0077704 A1 | 4/2003 | Rosen et al. |
| 2003/0077808 A1 | 4/2003 | Rosen et al. |
| 2003/0082681 A1 | 5/2003 | Rosen et al. |
| 2003/0082758 A1 | 5/2003 | Rosen et al. |
| 2003/0083481 A1 | 5/2003 | Birse et al. |
| 2003/0092102 A1 | 5/2003 | Rosen et al. |
| 2003/0092611 A9 | 5/2003 | Rosen et al. |
| 2003/0092615 A1 | 5/2003 | Rosen et al. |
| 2003/0096346 A1 | 5/2003 | Rosen et al. |
| 2003/0103950 A1 | 6/2003 | Sharpe |

(56) References Cited

U.S. PATENT DOCUMENTS

| | | |
|---|---|---|
| 2003/0108907 A1 | 6/2003 | Rosen et al. |
| 2003/0109690 A1 | 6/2003 | Ruben et al. |
| 2003/0113840 A1 | 6/2003 | Rosen et al. |
| 2003/0113910 A1 | 6/2003 | Levanduski |
| 2003/0124721 A1 | 7/2003 | Cheatham et al. |
| 2003/0125246 A9 | 7/2003 | Rosen et al. |
| 2003/0129685 A1 | 7/2003 | Ni et al. |
| 2003/0139327 A9 | 7/2003 | Rosen et al. |
| 2003/0143191 A1 | 7/2003 | Bell et al. |
| 2003/0152933 A1 | 8/2003 | Barash et al. |
| 2003/0157508 A1 | 8/2003 | Ebner et al. |
| 2003/0161817 A1 | 8/2003 | Young et al. |
| 2003/0166541 A1 | 9/2003 | Ruben et al. |
| 2003/0166864 A1 | 9/2003 | Yu et al. |
| 2003/0170215 A1 | 9/2003 | Tsang et al. |
| 2003/0171252 A9 | 9/2003 | Rosen et al. |
| 2003/0171267 A1 | 9/2003 | Rosen et al. |
| 2003/0175739 A1 | 9/2003 | Rosen et al. |
| 2003/0175858 A1 | 9/2003 | Ruben et al. |
| 2003/0181692 A1 | 9/2003 | Ni et al. |
| 2003/0190707 A1 | 10/2003 | Rosen et al. |
| 2003/0191298 A1 | 10/2003 | Barash et al. |
| 2003/0194708 A1 | 10/2003 | Binnerts et al. |
| 2003/0194802 A1 | 10/2003 | Itskovitz-Eldor et al. |
| 2003/0199008 A1 | 10/2003 | Rosen et al. |
| 2003/0199043 A1 | 10/2003 | Ballance et al. |
| 2003/0203361 A1 | 10/2003 | Rosen et al. |
| 2003/0207285 A1 | 11/2003 | Rosen et al. |
| 2003/0215893 A1 | 11/2003 | Rosen et al. |
| 2003/0219758 A1 | 11/2003 | Rosen et al. |
| 2003/0219875 A1 | 11/2003 | Rosen et al. |
| 2003/0220489 A1 | 11/2003 | Rosen et al. |
| 2003/0224376 A1 | 12/2003 | Meyers et al. |
| 2003/0224461 A1 | 12/2003 | Rosen et al. |
| 2003/0225009 A1 | 12/2003 | Rosen et al. |
| 2003/0232752 A1 | 12/2003 | Freeman et al. |
| 2003/0232975 A1 | 12/2003 | Rosen et al. |
| 2003/0235563 A1 | 12/2003 | Strom et al. |
| 2003/0235829 A1 | 12/2003 | Ruben et al. |
| 2003/0235831 A1 | 12/2003 | Rosen et al. |
| 2004/0002124 A1 | 1/2004 | Lau et al. |
| 2004/0002591 A1 | 1/2004 | Moore et al. |
| 2004/0005575 A1 | 1/2004 | Rosen et al. |
| 2004/0005577 A1 | 1/2004 | Rosen et al. |
| 2004/0005579 A1 | 1/2004 | Birse et al. |
| 2004/0009488 A1 | 1/2004 | Rosen et al. |
| 2004/0009491 A1 | 1/2004 | Birse et al. |
| 2004/0009589 A1 | 1/2004 | Levenberg et al. |
| 2004/0010121 A1 | 1/2004 | Birse et al. |
| 2004/0010132 A1 | 1/2004 | Rosen et al. |
| 2004/0010134 A1 | 1/2004 | Rosen et al. |
| 2004/0014039 A1 | 1/2004 | Rosen et al. |
| 2004/0018621 A1 | 1/2004 | Reid et al. |
| 2004/0018623 A1 | 1/2004 | Rosenberg |
| 2004/0023949 A1 | 2/2004 | Baxter et al. |
| 2004/0031067 A1 | 2/2004 | Herlyn et al. |
| 2004/0033599 A1 | 2/2004 | Rosenberg |
| 2004/0034196 A1 | 2/2004 | Komatsoulis et al. |
| 2004/0037813 A1 | 2/2004 | Simpson et al. |
| 2004/0044191 A1 | 3/2004 | Fischer et al. |
| 2004/0048296 A1 | 3/2004 | Ruben et al. |
| 2004/0052771 A1 | 3/2004 | Lim |
| 2004/0058443 A1 | 3/2004 | Artavanis-Tsakonas et al. |
| 2004/0067882 A1 | 4/2004 | Alsobrook, II et al. |
| 2004/0067953 A1 | 4/2004 | Stein et al. |
| 2004/0071687 A1 | 4/2004 | Rafii et al. |
| 2004/0101927 A9 | 5/2004 | Rosen et al. |
| 2004/0110287 A1 | 6/2004 | Clarke et al. |
| 2004/0115805 A1 | 6/2004 | Tsang et al. |
| 2004/0127406 A1 | 7/2004 | Presnell et al. |
| 2004/0132183 A1 | 7/2004 | Scharp et al. |
| 2004/0141957 A1 | 7/2004 | Tsang et al. |
| 2004/0146893 A1 | 7/2004 | Ruben et al. |
| 2004/0161419 A1 | 8/2004 | Strom et al. |
| 2004/0171123 A1 | 9/2004 | Rosen et al. |
| 2004/0175367 A1 | 9/2004 | Herlyn et al. |
| 2004/0185045 A1 | 9/2004 | Koenig et al. |
| 2004/0191901 A1 | 9/2004 | Assady et al. |
| 2004/0208869 A1 | 10/2004 | Allan |
| 2004/0208870 A1 | 10/2004 | Allan |
| 2004/0224302 A1 | 11/2004 | Jessel et al. |
| 2004/0224887 A1 | 11/2004 | Jessel et al. |
| 2004/0225113 A1 | 11/2004 | LaFleur et al. |
| 2004/0228846 A1 | 11/2004 | Pang et al. |
| 2004/0235113 A1 | 11/2004 | Shi et al. |
| 2004/0241803 A1 | 12/2004 | Rosen et al. |
| 2004/0242469 A1 | 12/2004 | Lee et al. |
| 2004/0242482 A1 | 12/2004 | Gehring et al. |
| 2004/0247567 A1 | 12/2004 | Gurtner |
| 2004/0253672 A1 | 12/2004 | Ruben et al. |
| 2004/0259244 A1 | 12/2004 | Scharp et al. |
| 2004/0266674 A1 | 12/2004 | Mills et al. |
| 2005/0002915 A1 | 1/2005 | Atala et al. |
| 2005/0013870 A1 | 1/2005 | Freyman et al. |
| 2005/0014727 A1 | 1/2005 | Muller et al. |
| 2005/0019866 A1 | 1/2005 | Ni et al. |
| 2005/0031598 A1 | 2/2005 | Levenberg et al. |
| 2005/0032168 A1 | 2/2005 | Rosen et al. |
| 2005/0037000 A1 | 2/2005 | Stavenhagen et al. |
| 2005/0037022 A1 | 2/2005 | Rosen et al. |
| 2005/0037467 A1 | 2/2005 | Ruben et al. |
| 2005/0037490 A1 | 2/2005 | Rosenberg et al. |
| 2005/0048490 A1 | 3/2005 | Azimzai et al. |
| 2005/0054051 A1 | 3/2005 | Rosen et al. |
| 2005/0054098 A1 | 3/2005 | Mistry et al. |
| 2005/0054102 A1 | 3/2005 | Wobus et al. |
| 2005/0054570 A1 | 3/2005 | Rosen et al. |
| 2005/0064514 A1 | 3/2005 | Stavenhagen et al. |
| 2005/0074875 A1 | 4/2005 | Nigam et al. |
| 2005/0080138 A1 | 4/2005 | Guicherit et al. |
| 2005/0085519 A1 | 4/2005 | Rubin et al. |
| 2005/0090465 A1 | 4/2005 | Ferber |
| 2005/0100549 A1 | 5/2005 | Roberts et al. |
| 2005/0100991 A1 | 5/2005 | Rosen et al. |
| 2005/0107339 A1 | 5/2005 | Muller et al. |
| 2005/0112106 A1 | 5/2005 | Gerecht-Nir et al. |
| 2005/0147593 A1 | 7/2005 | Kinch |
| 2005/0147960 A1 | 7/2005 | Levinson et al. |
| 2005/0153443 A1 | 7/2005 | Lanza et al. |
| 2005/0158859 A1 | 7/2005 | Artavanis-Tsakonas et al. |
| 2005/0176061 A1 | 8/2005 | Rosen et al. |
| 2005/0181371 A1 | 8/2005 | Rosen et al. |
| 2005/0181502 A1 | 8/2005 | Furcht et al. |
| 2005/0186664 A1 | 8/2005 | Rosen et al. |
| 2005/0191743 A1 | 9/2005 | Wu et al. |
| 2005/0196423 A1 | 9/2005 | Batich et al. |
| 2005/0197285 A1 | 9/2005 | Rosen et al. |
| 2005/0208565 A1 | 9/2005 | Roschke |
| 2005/0208602 A1 | 9/2005 | Rosen et al. |
| 2005/0208619 A1 | 9/2005 | Rosen et al. |
| 2005/0208653 A1 | 9/2005 | Pang et al. |
| 2005/0214786 A1 | 9/2005 | Birse et al. |
| 2005/0215767 A1 | 9/2005 | Koenig et al. |
| 2005/0222087 A1 | 10/2005 | Beachy et al. |
| 2005/0239059 A1 | 10/2005 | Ruben et al. |
| 2005/0244388 A1 | 11/2005 | Petersen et al. |
| 2005/0244931 A1 | 11/2005 | Rosen et al. |
| 2005/0255588 A1 | 11/2005 | Young et al. |
| 2005/0260213 A1 | 11/2005 | Koenig et al. |
| 2005/0260750 A1 | 11/2005 | Kerr-Conte et al. |
| 2005/0266532 A1 | 12/2005 | Rosen et al. |
| 2005/0266533 A1 | 12/2005 | Ballance et al. |
| 2005/0266555 A1 | 12/2005 | Lu et al. |
| 2005/0277190 A1 | 12/2005 | Seaberg et al. |
| 2006/0003380 A1 | 1/2006 | Ruben et al. |
| 2006/0008450 A1 | 1/2006 | Verfaillie et al. |
| 2006/0013810 A1 | 1/2006 | Johnson et al. |
| 2006/0014254 A1 | 1/2006 | Haseltine et al. |
| 2006/0025406 A1 | 2/2006 | Zembower et al. |
| 2006/0030041 A1 | 2/2006 | Furcht et al. |
| 2006/0030042 A1 | 2/2006 | Brivanlou et al. |
| 2006/0052596 A1 | 3/2006 | Muller et al. |
| 2006/0057138 A1 | 3/2006 | Wood et al. |
| 2006/0057542 A1 | 3/2006 | Sharpe et al. |

(56) References Cited

U.S. PATENT DOCUMENTS

| | | |
|---|---|---|
| 2006/0057582 A1 | 3/2006 | Rosen et al. |
| 2006/0068496 A1 | 3/2006 | Kelly |
| 2006/0073561 A1 | 4/2006 | Rosen et al. |
| 2006/0084082 A1 | 4/2006 | Ruben et al. |
| 2006/0084167 A1 | 4/2006 | Cohenford et al. |
| 2006/0084794 A1 | 4/2006 | Rosen et al. |
| 2006/0093586 A1 | 5/2006 | Musick |
| 2006/0094046 A1 | 5/2006 | Abo et al. |
| 2006/0099575 A9 | 5/2006 | Ruben et al. |
| 2006/0110830 A1 | 5/2006 | Dominko et al. |
| 2006/0122104 A1 | 6/2006 | Presnell et al. |
| 2006/0134709 A1 | 6/2006 | Stavenhagen et al. |
| 2006/0165666 A1 | 7/2006 | Lim |
| 2006/0166329 A1 | 7/2006 | Rosen et al. |
| 2006/0171930 A1 | 8/2006 | Seyda et al. |
| 2006/0177439 A1 | 8/2006 | Koenig et al. |
| 2006/0194321 A1 | 8/2006 | Colman et al. |
| 2006/0194735 A1 | 8/2006 | Rosen et al. |
| 2006/0198827 A1 | 9/2006 | Levenberg et al. |
| 2006/0222634 A1 | 10/2006 | Clarke et al. |
| 2006/0223077 A1 | 10/2006 | Ni et al. |
| 2006/0223177 A1 | 10/2006 | Harris et al. |
| 2006/0246483 A1 | 11/2006 | Rosen et al. |
| 2006/0246488 A1 | 11/2006 | Hipp et al. |
| 2006/0257965 A1 | 11/2006 | Lau |
| 2006/0258586 A1 | 11/2006 | Sheppard et al. |
| 2006/0263337 A1 | 11/2006 | Maziarz et al. |
| 2006/0269908 A1 | 11/2006 | Ware et al. |
| 2006/0270032 A1 | 11/2006 | Bhatia et al. |
| 2006/0275900 A1 | 12/2006 | Presnell et al. |
| 2006/0276396 A1 | 12/2006 | Rosen et al. |
| 2006/0281174 A1 | 12/2006 | Xu et al. |
| 2006/0281179 A1 | 12/2006 | Sasai et al. |
| 2006/0286635 A1 | 12/2006 | Rosen et al. |
| 2007/0003526 A1 | 1/2007 | Hayashi |
| 2007/0003529 A1 | 1/2007 | Sharpe |
| 2007/0009494 A1 | 1/2007 | Mistry et al. |
| 2007/0009521 A1 | 1/2007 | Ruben et al. |
| 2007/0009882 A1 | 1/2007 | Rosenberg |
| 2007/0014771 A1 | 1/2007 | Mistry et al. |
| 2007/0015162 A1 | 1/2007 | Rosen et al. |
| 2007/0015271 A1 | 1/2007 | Rosen et al. |
| 2007/0015279 A1 | 1/2007 | Tsang et al. |
| 2007/0015696 A1 | 1/2007 | Rosen et al. |
| 2007/0015908 A1 | 1/2007 | Fischer et al. |
| 2007/0020724 A1 | 1/2007 | Ruben et al. |
| 2007/0021493 A1 | 1/2007 | Guicherit et al. |
| 2007/0026013 A1 | 2/2007 | Rosen et al. |
| 2007/0026454 A1 | 2/2007 | Rosen et al. |
| 2007/0027306 A1 | 2/2007 | Rosen et al. |
| 2007/0031842 A1 | 2/2007 | Rosen et al. |
| 2007/0031966 A1 | 2/2007 | Dressler et al. |
| 2007/0032413 A1 | 2/2007 | Rosen et al. |
| 2007/0032414 A1 | 2/2007 | Rosen et al. |
| 2007/0036767 A1 | 2/2007 | Mistry et al. |
| 2007/0036799 A1 | 2/2007 | Stavenhagen et al. |
| 2007/0037206 A1 | 2/2007 | Rosen et al. |
| 2007/0037281 A1 | 2/2007 | Kruse |
| 2007/0042361 A1 | 2/2007 | Rosen et al. |
| 2007/0048282 A1 | 3/2007 | Rosen et al. |
| 2007/0048297 A1 | 3/2007 | Rosen et al. |
| 2007/0048818 A1 | 3/2007 | Rosen et al. |
| 2007/0053996 A1 | 3/2007 | Boyden et al. |
| 2007/0054319 A1 | 3/2007 | Boyden et al. |
| 2007/0055056 A1 | 3/2007 | Rosen et al. |
| 2007/0065942 A1 | 3/2007 | Wandinger-Ness et al. |
| 2007/0072292 A1 | 3/2007 | Tsang et al. |
| 2007/0099297 A1 | 5/2007 | Reid et al. |
| 2007/0099833 A1 | 5/2007 | Rosen et al. |
| 2007/0104697 A1 | 5/2007 | Wilkison et al. |
| 2007/0111203 A1 | 5/2007 | Cao et al. |
| 2007/0111306 A1 | 5/2007 | Salli et al. |
| 2007/0122903 A1 | 5/2007 | Rezania et al. |
| 2007/0149571 A1 | 6/2007 | Stein et al. |
| 2007/0160586 A1 | 7/2007 | Alt et al. |
| 2007/0166824 A1 | 7/2007 | Artavanis-Tsakonas et al. |
| 2007/0185024 A1 | 8/2007 | Jessell et al. |
| 2007/0190068 A1 | 8/2007 | Hart et al. |
| 2007/0190165 A1 | 8/2007 | Brey et al. |
| 2007/0207522 A1 | 9/2007 | Laurie et al. |
| 2007/0224650 A1 | 9/2007 | Jessell et al. |
| 2007/0238169 A1 | 10/2007 | Abilez et al. |
| 2007/0244047 A1 | 10/2007 | Rosen et al. |
| 2007/0248947 A1 | 10/2007 | Cezar |
| 2007/0254319 A1 | 11/2007 | Donnenberg et al. |
| 2007/0254359 A1 | 11/2007 | Rezania et al. |
| 2007/0259421 A1 | 11/2007 | D'Amour et al. |
| 2007/0259815 A1 | 11/2007 | Rosen et al. |
| 2007/0261127 A1 | 11/2007 | Boyden et al. |
| 2007/0280948 A1 | 12/2007 | Williams et al. |
| 2007/0281355 A1 | 12/2007 | Dalton et al. |
| 2007/0287173 A9 | 12/2007 | Rosen et al. |
| 2007/0292389 A1 | 12/2007 | Stassi et al. |
| 2007/0298491 A1 | 12/2007 | Rosen et al. |
| 2008/0004206 A1 | 1/2008 | Rosen et al. |
| 2008/0004277 A1 | 1/2008 | Chimmanamada et al. |
| 2008/0019950 A1 | 1/2008 | Heins et al. |
| 2008/0027147 A1 | 1/2008 | Meyers et al. |
| 2008/0031820 A1 | 2/2008 | Verfaillie et al. |
| 2008/0038352 A1 | 2/2008 | Simpson et al. |
| 2008/0044417 A1 | 2/2008 | Johnson et al. |
| 2008/0044429 A1 | 2/2008 | Johnson et al. |
| 2008/0064049 A1 | 3/2008 | Clarke et al. |
| 2008/0076176 A1 | 3/2008 | Dominko et al. |
| 2008/0089931 A1 | 4/2008 | Kinch |
| 2008/0090887 A1 | 4/2008 | Ying et al. |
| 2008/0103606 A1 | 5/2008 | Berkland et al. |
| 2008/0112961 A1 | 5/2008 | Stavenhagen et al. |
| 2008/0114061 A1 | 5/2008 | Muller et al. |
| 2008/0131399 A1 | 6/2008 | Ballance et al. |
| 2008/0131435 A1 | 6/2008 | Stavenhagen et al. |
| 2008/0131966 A1 | 6/2008 | Hariri |
| 2008/0138344 A1 | 6/2008 | Stavenhagen et al. |
| 2008/0138349 A1 | 6/2008 | Stavenhagen et al. |
| 2008/0146503 A1 | 6/2008 | Rosen et al. |
| 2008/0153751 A1 | 6/2008 | Rosen et al. |
| 2008/0159999 A1 | 7/2008 | Stefanidis |
| 2008/0160617 A1 | 7/2008 | Sasai et al. |
| 2008/0161243 A1 | 7/2008 | Rosen et al. |
| 2008/0167238 A1 | 7/2008 | Rosen et al. |
| 2008/0167239 A1 | 7/2008 | Rosen et al. |
| 2008/0167240 A1 | 7/2008 | Rosen et al. |
| 2008/0175828 A1 | 7/2008 | Freeman et al. |
| 2008/0176840 A1 | 7/2008 | Sun et al. |
| 2008/0182278 A1 | 7/2008 | Weissman et al. |
| 2008/0188406 A1 | 8/2008 | Pang et al. |
| 2008/0194023 A1 | 8/2008 | Gerecht-Nir et al. |
| 2008/0194481 A1 | 8/2008 | Rosen et al. |
| 2008/0199849 A1 | 8/2008 | Lim et al. |
| 2008/0213886 A1 | 9/2008 | Rosen et al. |
| 2008/0220453 A1 | 9/2008 | Ailles et al. |
| 2008/0227714 A1 | 9/2008 | Ruben et al. |
| 2008/0233649 A1 | 9/2008 | Seaberg et al. |
| 2008/0261877 A1 | 10/2008 | Ballance et al. |
| 2008/0267926 A1 | 10/2008 | Martinson et al. |
| 2008/0267962 A1 | 10/2008 | Ballance et al. |
| 2008/0269125 A1 | 10/2008 | Ballance et al. |
| 2008/0269126 A1 | 10/2008 | Ballance et al. |
| 2008/0269127 A1 | 10/2008 | Ballance et al. |
| 2008/0269128 A1 | 10/2008 | Ballance et al. |
| 2008/0286867 A1 | 11/2008 | Deng et al. |
| 2008/0293629 A1 | 11/2008 | Rosen et al. |
| 2008/0299655 A1 | 12/2008 | Nigam et al. |
| 2009/0004152 A1 | 1/2009 | Martinson et al. |
| 2009/0017023 A1 | 1/2009 | Koenig et al. |
| 2009/0017024 A1 | 1/2009 | Estok et al. |
| 2009/0017026 A1 | 1/2009 | Koenig et al. |
| 2009/0017027 A1 | 1/2009 | Koenig et al. |
| 2009/0029914 A1 | 1/2009 | Rosen et al. |
| 2009/0042792 A1 | 2/2009 | Shi et al. |
| 2009/0042875 A1 | 2/2009 | Muller et al. |
| 2009/0047212 A1 | 2/2009 | Berman et al. |
| 2009/0053218 A1 | 2/2009 | Koenig et al. |
| 2009/0053238 A1 | 2/2009 | Allan |

(56) References Cited

U.S. PATENT DOCUMENTS

| | | |
|---|---|---|
| 2009/0074771 A1 | 3/2009 | Koenig et al. |
| 2009/0075381 A1 | 3/2009 | Clarke et al. |
| 2009/0075880 A1 | 3/2009 | Rosen et al. |
| 2009/0076251 A1 | 3/2009 | Koenig et al. |
| 2009/0081228 A1 | 3/2009 | Lau et al. |
| 2009/0092586 A1 | 4/2009 | Verfaillie et al. |
| 2009/0092610 A1 | 4/2009 | Koenig et al. |
| 2009/0093402 A1 | 4/2009 | Rosen et al. |
| 2009/0098124 A1 | 4/2009 | Stavenhagen |
| 2009/0099073 A1 | 4/2009 | Rosen et al. |
| 2009/0104159 A1 | 4/2009 | Prosper et al. |
| 2009/0104163 A1 | 4/2009 | Deans et al. |
| 2009/0105140 A1 | 4/2009 | Rosen et al. |
| 2009/0111177 A1 | 4/2009 | Brivanlou et al. |
| 2009/0123430 A1 | 5/2009 | De Sousa |
| 2009/0162329 A1 | 6/2009 | Anversa et al. |
| 2009/0162437 A1 | 6/2009 | Horii et al. |
| 2009/0170198 A1 | 7/2009 | Rezania |
| 2009/0191159 A1 | 7/2009 | Sakurada et al. |
| 2009/0202537 A1 | 8/2009 | Johnson et al. |
| 2009/0202977 A1 | 8/2009 | Ott et al. |
| 2009/0203129 A1 | 8/2009 | Furcht et al. |
| 2009/0203130 A1 | 8/2009 | Furcht et al. |
| 2009/0203635 A1 | 8/2009 | Rosen et al. |
| 2009/0220996 A1 | 9/2009 | Mehtal et al. |
| 2009/0221072 A1 | 9/2009 | Chen et al. |
| 2009/0226447 A1 | 9/2009 | Boone et al. |
| 2009/0227533 A1 | 9/2009 | Bader et al. |
| 2009/0232808 A1 | 9/2009 | Priest et al. |
| 2009/0233353 A1 | 9/2009 | Furcht et al. |
| 2009/0233354 A1 | 9/2009 | Furcht et al. |
| 2009/0246178 A1 | 10/2009 | Tsang et al. |
| 2009/0247540 A1 | 10/2009 | Wang et al. |
| 2009/0269845 A1 | 10/2009 | Rezania |
| 2009/0274663 A1 | 11/2009 | Shiels et al. |
| 2009/0285816 A9 | 11/2009 | Ballance et al. |
| 2009/0285883 A1 | 11/2009 | Houchen et al. |
| 2009/0298169 A1 | 12/2009 | Dalton et al. |
| 2009/0304646 A1 | 12/2009 | Sakurada et al. |
| 2009/0325293 A1 | 12/2009 | Davis et al. |
| 2010/0010068 A1 | 1/2010 | Ren et al. |
| 2010/0015100 A1 | 1/2010 | Xu |
| 2010/0015150 A1 | 1/2010 | Carlson et al. |
| 2010/0015711 A1 | 1/2010 | Davis et al. |
| 2010/0028306 A1 | 2/2010 | Clarke et al. |
| 2010/0028307 A1 | 2/2010 | O'Neil |
| 2010/0034791 A1 | 2/2010 | Lelkes et al. |
| 2010/0048472 A1 | 2/2010 | Rosen et al. |
| 2010/0068190 A1 | 3/2010 | Dimmeler et al. |
| 2010/0069386 A1 | 3/2010 | Beachy et al. |
| 2010/0086525 A1 | 4/2010 | Zaret et al. |
| 2010/0093627 A1 | 4/2010 | Rosen et al. |
| 2010/0105100 A1 | 4/2010 | Sakurada et al. |
| 2010/0112691 A1 | 5/2010 | Green et al. |
| 2010/0113447 A1 | 5/2010 | Burlison et al. |
| 2010/0119496 A1 | 5/2010 | Wilkison et al. |
| 2010/0120069 A1 | 5/2010 | Sakurada et al. |
| 2010/0129351 A1 | 5/2010 | Zaret et al. |
| 2010/0136688 A1 | 6/2010 | Ruiz et al. |
| 2010/0150876 A1 | 6/2010 | Verfaillie et al. |
| 2010/0166713 A1 | 7/2010 | Dalton et al. |
| 2010/0169990 A1 | 7/2010 | Clarke et al. |
| 2010/0172994 A1 | 7/2010 | Sigmund et al. |
| 2010/0189686 A1 | 7/2010 | Rosen et al. |
| 2010/0196361 A1 | 8/2010 | Wood et al. |
| 2010/0196362 A1 | 8/2010 | Stavenhagen et al. |
| 2010/0209396 A1 | 8/2010 | Daley et al. |
| 2010/0209467 A1 | 8/2010 | Carlson et al. |
| 2010/0210013 A1 | 8/2010 | Mistry et al. |
| 2010/0233239 A1 | 9/2010 | Berkland et al. |
| 2010/0234273 A1 | 9/2010 | Boyden et al. |
| 2010/0240130 A1 | 9/2010 | Majumdar et al. |
| 2010/0247601 A1 | 9/2010 | Okihana |
| 2010/0249026 A1 | 9/2010 | Rosen et al. |
| 2010/0254944 A1 | 10/2010 | Subramanian et al. |
| 2010/0254996 A1 | 10/2010 | Brantley-Sieders et al. |
| 2010/0255580 A1 | 10/2010 | Rezania |
| 2010/0260728 A1 | 10/2010 | Martinson et al. |
| 2010/0267079 A1 | 10/2010 | Weissman et al. |
| 2010/0267135 A1 | 10/2010 | Sakurada et al. |
| 2010/0267814 A1 | 10/2010 | Bennett et al. |
| 2010/0285031 A1 | 11/2010 | Sukumar et al. |
| 2010/0285584 A1 | 11/2010 | Weiss et al. |
| 2010/0286048 A1 | 11/2010 | Rosen et al. |
| 2010/0291033 A1 | 11/2010 | Rosen et al. |
| 2010/0292177 A1 | 11/2010 | Armstrong et al. |
| 2010/0297149 A1 | 11/2010 | Zhou et al. |
| 2010/0297210 A1 | 11/2010 | Okihana |
| 2010/0297757 A1 | 11/2010 | Dressler et al. |
| 2010/0298331 A1 | 11/2010 | Lee et al. |
| 2010/0310576 A1 | 12/2010 | Adams et al. |
| 2011/0002888 A1 | 1/2011 | Rosen et al. |
| 2011/0002897 A1 | 1/2011 | Snyder et al. |
| 2011/0008298 A1 | 1/2011 | Lim et al. |
| 2011/0008887 A1 | 1/2011 | Tsang et al. |
| 2011/0008892 A1 | 1/2011 | Nigam et al. |
| 2011/0009312 A1 | 1/2011 | Rosen et al. |
| 2011/0014160 A1 | 1/2011 | Hald et al. |
| 2011/0014163 A1 | 1/2011 | Xu |
| 2011/0014692 A1 | 1/2011 | Lim et al. |
| 2011/0014702 A1 | 1/2011 | Xu |
| 2011/0020380 A1 | 1/2011 | Ruben et al. |
| 2011/0021607 A1 | 1/2011 | Clarke et al. |
| 2011/0033928 A1 | 2/2011 | Smith et al. |
| 2011/0045045 A1 | 2/2011 | Cortiella et al. |
| 2011/0064701 A1 | 3/2011 | Young et al. |
| 2011/0077256 A1 | 3/2011 | Guicherit et al. |
| 2011/0081654 A1 | 4/2011 | Hipp et al. |
| 2011/0104805 A1 | 5/2011 | Fung et al. |
| 2011/0105483 A1 | 5/2011 | Chimmanamada et al. |
| 2011/0124032 A1 | 5/2011 | Diehn et al. |
| 2011/0135610 A1 | 6/2011 | Reid et al. |
| 2011/0144103 A1 | 6/2011 | Chimmanamada et al. |
| 2011/0151561 A1 | 6/2011 | Davis et al. |
| 2011/0152310 A1 | 6/2011 | Burlison et al. |
| 2011/0158905 A1 | 6/2011 | Goldenberg et al. |
| 2011/0177042 A1 | 7/2011 | Herlyn et al. |
| 2011/0182879 A1 | 7/2011 | Meyers et al. |
| 2011/0189140 A1 | 8/2011 | Christman et al. |
| 2011/0195094 A1 | 8/2011 | Ying et al. |
| 2011/0195503 A1 | 8/2011 | Totey et al. |
| 2011/0212067 A1 | 9/2011 | Karanu et al. |
| 2011/0224206 A1 | 9/2011 | Ying et al. |
| 2011/0224223 A1 | 9/2011 | Shokat et al. |
| 2011/0243941 A1 | 10/2011 | Stavenhagen et al. |
| 2011/0250686 A1 | 10/2011 | Heins et al. |
| 2011/0251150 A2 | 10/2011 | Bennett et al. |
| 2011/0265197 A1 | 10/2011 | Depinho et al. |
| 2011/0274662 A1 | 11/2011 | Malcuit et al. |
| 2011/0280830 A9 | 11/2011 | Rosen et al. |
| 2011/0287071 A1 | 11/2011 | Mitrani |
| 2011/0288026 A1 | 11/2011 | Simpson et al. |
| 2011/0293611 A1 | 12/2011 | Pearl et al. |
| 2011/0301209 A1 | 12/2011 | Zaknoen et al. |
| 2011/0305714 A1 | 12/2011 | Stavenhagen et al. |
| 2011/0312019 A1 | 12/2011 | West et al. |
| 2011/0318389 A1 | 12/2011 | Czernichow et al. |
| 2011/0319447 A1 | 12/2011 | Sun et al. |
| 2012/0003736 A1 | 1/2012 | Stern et al. |
| 2012/0009186 A1 | 1/2012 | Koenig et al. |
| 2012/0009203 A1 | 1/2012 | Jewett |
| 2012/0009675 A1 | 1/2012 | Martinson et al. |
| 2012/0021513 A1 | 1/2012 | Schulz et al. |
| 2012/0021985 A1 | 1/2012 | Rosen et al. |
| 2012/0028355 A1 | 2/2012 | Sato et al. |
| 2012/0034237 A1 | 2/2012 | Boone et al. |
| 2012/0034692 A1 | 2/2012 | D'Amour et al. |
| 2012/0039955 A1 | 2/2012 | Xu |
| 2012/0045830 A1 | 2/2012 | Green et al. |
| 2012/0046221 A1 | 2/2012 | Rosen et al. |
| 2012/0046288 A1 | 2/2012 | Burlison et al. |
| 2012/0046346 A1 | 2/2012 | Rossi et al. |
| 2012/0052568 A1 | 3/2012 | Subramanian et al. |
| 2012/0052571 A1 | 3/2012 | Fryer |

(56) References Cited

U.S. PATENT DOCUMENTS

| | | |
|---|---|---|
| 2012/0052576 A1 | 3/2012 | Rezania |
| 2012/0058562 A1 | 3/2012 | Thomson et al. |
| 2012/0064047 A1 | 3/2012 | Verfaillie et al. |
| 2012/0064537 A1 | 3/2012 | Ross |
| 2012/0100115 A1 | 4/2012 | Morrison et al. |
| 2012/0101072 A1 | 4/2012 | Burlison et al. |
| 2012/0115226 A1 | 5/2012 | Stachelsheid et al. |
| 2012/0121554 A1 | 5/2012 | Pappan |
| 2012/0121560 A1 | 5/2012 | Efrat et al. |
| 2012/0122869 A1 | 5/2012 | Ying et al. |
| 2012/0135043 A1 | 5/2012 | Maziarz et al. |
| 2012/0141415 A1 | 6/2012 | Ballance et al. |
| 2012/0141449 A1 | 6/2012 | Ballance et al. |
| 2012/0141476 A1 | 6/2012 | Johnson et al. |
| 2012/0142093 A1 | 6/2012 | Takahashi et al. |
| 2012/0148540 A1 | 6/2012 | Freeman et al. |
| 2012/0149051 A1 | 6/2012 | Kugelmeier et al. |
| 2012/0156250 A1 | 6/2012 | Christman et al. |
| 2012/0159655 A1 | 6/2012 | Lorens et al. |
| 2012/0190111 A1 | 7/2012 | Davis et al. |
| 2012/0190112 A1 | 7/2012 | Davis et al. |
| 2012/0196312 A1 | 8/2012 | Sato et al. |
| 2012/0196365 A1 | 8/2012 | Davis et al. |
| 2012/0202813 A1 | 8/2012 | Chimmanamada et al. |
| 2012/0216304 A1 | 8/2012 | Bhatia et al. |
| 2012/0219535 A1 | 8/2012 | Maxson, Jr. et al. |
| 2012/0219551 A1 | 8/2012 | Johnson et al. |
| 2012/0225073 A1 | 9/2012 | Weissman et al. |
| 2012/0230966 A1 | 9/2012 | Crawford et al. |
| 2012/0252732 A1 | 10/2012 | Ballance et al. |
| 2012/0253102 A1 | 10/2012 | Marban et al. |
| 2012/0258122 A1 | 10/2012 | Boone et al. |
| 2012/0263711 A1 | 10/2012 | Stavenhagen et al. |
| 2012/0264209 A1 | 10/2012 | Odorico et al. |
| 2012/0270319 A1 | 10/2012 | Clarke et al. |
| 2012/0276094 A1 | 11/2012 | Stavenhagen et al. |
| 2012/0288564 A1 | 11/2012 | Kurisawa et al. |
| 2012/0288936 A1 | 11/2012 | Ahlfors et al. |
| 2012/0295962 A1 | 11/2012 | Bennett et al. |
| 2012/0301444 A1 | 11/2012 | Clarke et al. |
| 2012/0315251 A1 | 12/2012 | Harris et al. |
| 2012/0322864 A1 | 12/2012 | Rossi et al. |
| 2012/0322865 A1 | 12/2012 | Rossi et al. |
| 2013/0029416 A1 | 1/2013 | Thatava et al. |
| 2013/0029875 A1 | 1/2013 | Stehno-Bittel et al. |
| 2013/0029911 A1 | 1/2013 | Rosen et al. |
| 2013/0031645 A1 | 1/2013 | Touboul et al. |
| 2013/0034525 A1 | 2/2013 | Yu et al. |
| 2013/0040853 A1 | 2/2013 | Chin et al. |
| 2013/0045187 A1 | 2/2013 | Semechkin et al. |
| 2013/0052177 A1 | 2/2013 | Schimmel et al. |
| 2013/0058900 A1 | 3/2013 | Lanza et al. |
| 2013/0061340 A1 | 3/2013 | Dylla et al. |
| 2013/0061342 A1 | 3/2013 | Dylla et al. |
| 2013/0071363 A1 | 3/2013 | Smith et al. |
| 2013/0071364 A1 | 3/2013 | Smith et al. |
| 2013/0072461 A1 | 3/2013 | Chimmanamada et al. |
| 2013/0072489 A1 | 3/2013 | Chimmanamada et al. |
| 2013/0072564 A1 | 3/2013 | Wang et al. |
| 2013/0084281 A1 | 4/2013 | Estok et al. |
| 2013/0095567 A1 | 4/2013 | Brolen et al. |
| 2013/0102023 A1 | 4/2013 | Smith et al. |
| 2013/0102533 A1 | 4/2013 | Rosen et al. |
| 2013/0108606 A1 | 5/2013 | Rosen et al. |
| 2013/0108630 A1 | 5/2013 | Watkins et al. |
| 2013/0115197 A1 | 5/2013 | Emig et al. |
| 2013/0115695 A1 | 5/2013 | Schulz |
| 2013/0122586 A1 | 5/2013 | Kanamune et al. |
| 2013/0137650 A1 | 5/2013 | Armstrong et al. |
| 2013/0150296 A1 | 6/2013 | Rosen et al. |
| 2013/0157933 A1 | 6/2013 | Rosen et al. |
| 2013/0184817 A1 | 7/2013 | Boyden et al. |
| 2013/0190350 A1 | 7/2013 | Rubin et al. |
| 2013/0202563 A1 | 8/2013 | Badylak et al. |
| 2013/0202606 A1 | 8/2013 | Stavenhagen et al. |
| 2013/0209427 A1 | 8/2013 | Thangapazham et al. |
| 2013/0210060 A1 | 8/2013 | Hosoya et al. |
| 2013/0224116 A1 | 8/2013 | Bonder et al. |
| 2013/0231294 A1 | 9/2013 | Carlson et al. |
| 2013/0243766 A1 | 9/2013 | Zhou et al. |
| 2013/0251687 A1 | 9/2013 | Christman et al. |
| 2013/0260385 A1 | 10/2013 | Dylla et al. |
| 2013/0261164 A1 | 10/2013 | Chimmanamada et al. |
| 2013/0263297 A1 | 10/2013 | Chu et al. |
| 2013/0266553 A1 | 10/2013 | Ballance et al. |
| 2013/0266939 A1 | 10/2013 | McVay et al. |
| 2013/0273045 A1 | 10/2013 | Watkins et al. |
| 2013/0273083 A1 | 10/2013 | Parenteau et al. |
| 2013/0280230 A1 | 10/2013 | Greene et al. |
| 2013/0280719 A1 | 10/2013 | Lim et al. |
| 2013/0280802 A1 | 10/2013 | Schulz et al. |
| 2013/0287744 A1 | 10/2013 | Paukshto et al. |
| 2013/0296378 A1 | 11/2013 | Sun et al. |
| 2013/0303493 A1 | 11/2013 | Burlison et al. |
| 2013/0330822 A1 | 12/2013 | Nakahata et al. |
| 2013/0333059 A1 | 12/2013 | Sukumar et al. |
| 2013/0336938 A1 | 12/2013 | Bloch et al. |
| 2013/0336992 A1 | 12/2013 | Boone et al. |
| 2013/0337561 A1 | 12/2013 | Majumdar et al. |
| 2013/0337562 A1 | 12/2013 | Stern et al. |
| 2013/0337564 A1 | 12/2013 | Davis et al. |
| 2013/0345219 A1 | 12/2013 | Lee et al. |
| 2013/0347133 A1 | 12/2013 | Cao et al. |
| 2014/0004095 A1 | 1/2014 | Ballance et al. |
| 2014/0004121 A1 | 1/2014 | Fanslow et al. |
| 2014/0010789 A1 | 1/2014 | Scheel et al. |
| 2014/0010798 A1 | 1/2014 | Ballance et al. |
| 2014/0011278 A1 | 1/2014 | Nigam et al. |
| 2014/0023624 A1 | 1/2014 | Zhou et al. |
| 2014/0024116 A1 | 1/2014 | Subramanian et al. |
| 2014/0030786 A1 | 1/2014 | Clarke et al. |
| 2014/0038291 A1 | 2/2014 | Ahlfors et al. |
| 2014/0044754 A1 | 2/2014 | Carlson et al. |
| 2014/0045263 A1 | 2/2014 | Mistry et al. |
| 2014/0073527 A1 | 3/2014 | Hurley et al. |
| 2014/0080210 A1 | 3/2014 | Davis et al. |
| 2014/0105888 A1 | 4/2014 | Foord et al. |
| 2014/0134162 A1 | 5/2014 | Stavenhagen et al. |
| 2014/0134733 A1 | 5/2014 | Wu et al. |
| 2014/0141509 A1 | 5/2014 | Gadue et al. |
| 2014/0154801 A1 | 6/2014 | D'Amour et al. |
| 2014/0178450 A1 | 6/2014 | Christman et al. |
| 2014/0179596 A1 | 6/2014 | Rosen et al. |
| 2014/0186305 A1 | 7/2014 | Rezina |
| 2014/0193373 A1 | 7/2014 | Ku |
| 2014/0206854 A1 | 7/2014 | Bennett et al. |
| 2014/0212395 A1 | 7/2014 | Hornstein et al. |
| 2014/0219997 A1 | 8/2014 | Berkland et al. |
| 2014/0234957 A1 | 8/2014 | Weiss et al. |
| 2014/0235479 A1 | 8/2014 | Depinho et al. |
| 2014/0242038 A1 | 8/2014 | Hua et al. |
| 2014/0243227 A1 | 8/2014 | Clevers et al. |
| 2014/0248238 A1 | 9/2014 | Wilson, Jr. et al. |
| 2014/0255861 A1 | 9/2014 | Smith et al. |
| 2014/0255969 A1 | 9/2014 | Cezar |
| 2014/0256037 A1 | 9/2014 | Sato et al. |
| 2014/0271566 A1 | 9/2014 | Agulnick |
| 2014/0271843 A1 | 9/2014 | Ma et al. |
| 2014/0273069 A1 | 9/2014 | West et al. |
| 2014/0274953 A1 | 9/2014 | Lee et al. |
| 2014/0288301 A1 | 9/2014 | Chimmanamada et al. |
| 2014/0289877 A1 | 9/2014 | Taniguchi et al. |
| 2014/0296186 A1 | 10/2014 | Ying et al. |
| 2014/0302491 A1 | 10/2014 | Nadauld et al. |
| 2014/0302601 A1 | 10/2014 | Reid et al. |
| 2014/0303077 A1 | 10/2014 | Rosen et al. |
| 2014/0308746 A1 | 10/2014 | Rossi et al. |
| 2014/0315753 A1 | 10/2014 | Guye et al. |
| 2014/0328794 A1 | 11/2014 | Rosen et al. |
| 2014/0329315 A1 | 11/2014 | Odorico et al. |
| 2014/0329318 A1 | 11/2014 | Rajagopal et al. |
| 2014/0329321 A1 | 11/2014 | Rajesh et al. |
| 2014/0329704 A1 | 11/2014 | Melton et al. |
| 2014/0349397 A1 | 11/2014 | Thomson et al. |

(56) References Cited

U.S. PATENT DOCUMENTS

| | | |
|---|---|---|
| 2014/0356951 A1 | 12/2014 | Thatava et al. |
| 2014/0363886 A1 | 12/2014 | Pourquie et al. |
| 2014/0370515 A1 | 12/2014 | Ai et al. |
| 2014/0371222 A1 | 12/2014 | Sun et al. |
| 2014/0371294 A1 | 12/2014 | Zhou et al. |
| 2015/0005299 A1 | 1/2015 | Chimmanamada et al. |
| 2015/0017134 A1 | 1/2015 | Guo et al. |
| 2015/0017135 A1 | 1/2015 | Agulnick |
| 2015/0017727 A1 | 1/2015 | Ferber |
| 2015/0023911 A1 | 1/2015 | Schilling et al. |
| 2015/0023934 A1 | 1/2015 | Ionas et al. |
| 2015/0023964 A1 | 1/2015 | Johnson et al. |
| 2015/0024458 A1 | 1/2015 | Chang et al. |
| 2015/0030636 A1 | 1/2015 | Dylla et al. |
| 2015/0030657 A1 | 1/2015 | Ludlow et al. |
| 2015/0050298 A1 | 2/2015 | Fletcher et al. |
| 2015/0051203 A1 | 2/2015 | Chimmanamada et al. |
| 2015/0056647 A1 | 2/2015 | Ruiz et al. |
| 2015/0064784 A1 | 3/2015 | Stern et al. |
| 2015/0086512 A1 | 3/2015 | Malcuit et al. |
| 2015/0087627 A1 | 3/2015 | Ren et al. |
| 2015/0118193 A1 | 4/2015 | Maziarz et al. |
| 2015/0119395 A1 | 4/2015 | Chimmanamada et al. |
| 2015/0119475 A1 | 4/2015 | Lorens et al. |
| 2015/0125507 A1 | 5/2015 | Chen et al. |
| 2015/0125953 A1 | 5/2015 | Hashino et al. |
| 2015/0126451 A1 | 5/2015 | Carlson et al. |
| 2015/0126499 A1 | 5/2015 | Burlison et al. |
| 2015/0132277 A1 | 5/2015 | Schimmel et al. |
| 2015/0132355 A1 | 5/2015 | Carlson et al. |
| 2015/0132846 A1 | 5/2015 | Schulz |
| 2015/0140072 A1 | 5/2015 | Watkins et al. |
| 2015/0147301 A1 | 5/2015 | Semechkin et al. |
| 2015/0159139 A1 | 6/2015 | Rezania et al. |
| 2015/0160246 A1 | 6/2015 | Idelevich et al. |
| 2015/0164784 A1 | 6/2015 | Zimmermann et al. |
| 2015/0165227 A1 | 6/2015 | Deisseroth et al. |
| 2015/0183771 A1 | 7/2015 | Ying et al. |
| 2015/0202235 A1 | 7/2015 | Emig et al. |
| 2015/0203568 A1 | 7/2015 | Rosen et al. |
| 2015/0212065 A1 | 7/2015 | Lorens et al. |
| 2015/0218522 A1 | 8/2015 | Peterson et al. |
| 2015/0225698 A1 | 8/2015 | Vallier et al. |
| 2015/0238530 A1 | 8/2015 | Jewett |
| 2015/0238656 A1 | 8/2015 | Orlando et al. |
| 2015/0240212 A1 | 8/2015 | Peterson et al. |
| 2015/0247124 A1 | 9/2015 | Snoeck et al. |
| 2015/0247194 A1 | 9/2015 | Hipp et al. |
| 2015/0252323 A1 | 9/2015 | Morrison et al. |
| 2015/0252327 A1 | 9/2015 | Rezania |
| 2015/0252349 A1 | 9/2015 | Greene et al. |
| 2015/0258145 A1 | 9/2015 | Crawford et al. |
| 2015/0259396 A1 | 9/2015 | Stavenhagen et al. |
| 2015/0265656 A1 | 9/2015 | Shamblott |
| 2015/0265657 A1 | 9/2015 | Martinson et al. |
| 2015/0266858 A1 | 9/2015 | Sun et al. |
| 2015/0267167 A1 | 9/2015 | Furcht et al. |
| 2015/0275168 A1 | 10/2015 | Oxburgh et al. |
| 2015/0275171 A1 | 10/2015 | Kato et al. |
| 2015/0284689 A1 | 10/2015 | Nigam |
| 2015/0290249 A1 | 10/2015 | Xu |
| 2015/0301025 A1 | 10/2015 | Smith et al. |
| 2015/0301058 A1 | 10/2015 | Schettini et al. |
| 2015/0329619 A1 | 11/2015 | Rosen et al. |
| 2015/0329821 A1 | 11/2015 | Ang et al. |
| 2015/0329829 A1 | 11/2015 | Shen et al. |
| 2015/0344574 A1 | 12/2015 | Koenig et al. |
| 2015/0344575 A1 | 12/2015 | Koenig et al. |
| 2015/0359823 A1 | 12/2015 | Furcht et al. |
| 2015/0361401 A1 | 12/2015 | Han et al. |
| 2015/0366885 A1 | 12/2015 | Ying et al. |
| 2015/0368616 A1 | 12/2015 | Jensen et al. |
| 2015/0368667 A1 | 12/2015 | Evans et al. |
| 2015/0376574 A1 | 12/2015 | Talavera-Adame et al. |
| 2016/0000789 A1 | 1/2016 | Shokat et al. |
| 2016/0000834 A1 | 1/2016 | Kinsey et al. |
| 2016/0002595 A1 | 1/2016 | Keller et al. |
| 2016/0009724 A1 | 1/2016 | Burlison et al. |
| 2016/0010055 A1 | 1/2016 | Parent et al. |
| 2016/0017288 A1 | 1/2016 | Akirav |
| 2016/0017290 A1 | 1/2016 | Efrat et al. |
| 2016/0030359 A1 | 2/2016 | Ma et al. |
| 2016/0030638 A1 | 2/2016 | Ross |
| 2016/0032249 A1 | 2/2016 | Melton et al. |
| 2016/0038544 A1 | 2/2016 | Keller et al. |
| 2016/0040130 A1 | 2/2016 | Rezania |
| 2016/0045498 A1 | 2/2016 | Ernst et al. |
| 2016/0046903 A1 | 2/2016 | Taniguchi et al. |
| 2016/0046941 A1 | 2/2016 | Bennett et al. |
| 2016/0053229 A1 | 2/2016 | Chien et al. |
| 2016/0053318 A1 | 2/2016 | Bonder et al. |
| 2016/0058794 A1 | 3/2016 | Lagasse |
| 2016/0061817 A1 | 3/2016 | Xian |
| 2016/0068580 A1 | 3/2016 | Cho et al. |
| 2016/0069865 A1 | 3/2016 | Cho et al. |
| 2016/0083693 A1 | 3/2016 | Xu et al. |
| 2016/0089371 A1 | 3/2016 | Liu et al. |
| 2016/0096036 A1 | 4/2016 | Deisseroth et al. |
| 2016/0101133 A1 | 4/2016 | Basu et al. |
| 2016/0108363 A1 | 4/2016 | Chien et al. |
| 2016/0115444 A1 | 4/2016 | Studer et al. |
| 2016/0115448 A1 | 4/2016 | Studer et al. |
| 2016/0120911 A1 | 5/2016 | Bloch et al. |
| 2016/0122708 A1 | 5/2016 | Rahmo |
| 2016/0122722 A1 | 5/2016 | Ejiri et al. |
| 2016/0122803 A1 | 5/2016 | Meissner et al. |
| 2016/0130561 A1 | 5/2016 | Sproul et al. |
| 2016/0137986 A1 | 5/2016 | Lee et al. |
| 2016/0152674 A1 | 6/2016 | Carlson et al. |
| 2016/0152687 A1 | 6/2016 | Rosen et al. |
| 2016/0152949 A1 | 6/2016 | Ten Berge et al. |
| 2016/0160182 A1 | 6/2016 | Rezania et al. |
| 2016/0160184 A1 | 6/2016 | Ahlfors et al. |
| 2016/0161486 A1 | 6/2016 | Parenteau et al. |
| 2016/0161488 A1 | 6/2016 | Parenteau et al. |
| 2016/0177270 A1 | 6/2016 | Takebe et al. |
| 2016/0177273 A1 | 6/2016 | Gong et al. |
| 2016/0186259 A1 | 6/2016 | Ofir et al. |
| 2016/0213717 A1 | 7/2016 | Xu et al. |
| 2016/0223555 A1 | 8/2016 | Zaret et al. |
| 2016/0228506 A1 | 8/2016 | Afeyan et al. |
| 2016/0230163 A1 | 8/2016 | Adams et al. |
| 2016/0237401 A1 | 8/2016 | Vallier et al. |
| 2016/0244751 A1 | 8/2016 | Ilagan |
| 2016/0250262 A1 | 9/2016 | Agulnick et al. |
| 2016/0251627 A1 | 9/2016 | Majumdar et al. |
| 2016/0252494 A1 | 9/2016 | Bhatia et al. |
| 2016/0252524 A1 | 9/2016 | Deisseroth et al. |
| 2016/0256499 A1 | 9/2016 | Peltz et al. |
| 2016/0257937 A1 | 9/2016 | Wauthier et al. |
| 2016/0272723 A1 | 9/2016 | Foord et al. |
| 2016/0272944 A1 | 9/2016 | Ding et al. |
| 2016/0274121 A1 | 9/2016 | Wong et al. |
| 2016/0281062 A1 | 9/2016 | Zink et al. |
| 2016/0289642 A1 | 10/2016 | Osafune et al. |
| 2016/0297868 A1 | 10/2016 | Bidwell et al. |
| 2016/0298088 A1 | 10/2016 | Xu et al. |
| 2016/0304823 A1 | 10/2016 | Hirano et al. |
| 2016/0304839 A1 | 10/2016 | Iwata et al. |
| 2016/0313306 A1 | 10/2016 | Ingber et al. |
| 2016/0326491 A1 | 11/2016 | Chambers et al. |
| 2016/0340440 A1 | 11/2016 | Fanslow et al. |
| 2016/0341726 A1 | 11/2016 | Humphreys et al. |
| 2016/0355787 A1 | 12/2016 | D'Amour et al. |
| 2016/0361466 A1 | 12/2016 | Yanagawa et al. |
| 2016/0363584 A1 | 12/2016 | McGeehan et al. |
| 2016/0367695 A1 | 12/2016 | Wilson et al. |
| 2016/0369238 A1 | 12/2016 | McGeehan et al. |
| 2016/0376557 A1 | 12/2016 | Dubart Kupperschmitt et al. |
| 2017/0002091 A1 | 1/2017 | Greene et al. |
| 2017/0002313 A1 | 1/2017 | Doudement et al. |
| 2017/0002327 A1 | 1/2017 | Brolen et al. |
| 2017/0009211 A1 | 1/2017 | Hornstein et al. |
| 2017/0009212 A1 | 1/2017 | Fryer |

(56) References Cited

U.S. PATENT DOCUMENTS

| | | |
|---|---|---|
| 2017/0016886 A1 | 1/2017 | Han et al. |
| 2017/0027994 A1 | 2/2017 | Kotton et al. |
| 2017/0029778 A1 | 2/2017 | Peterson et al. |
| 2017/0029783 A1 | 2/2017 | Ahlfors et al. |
| 2017/0037354 A1 | 2/2017 | Larkin et al. |
| 2017/0044570 A1 | 2/2017 | Weiss et al. |
| 2017/0045497 A1 | 2/2017 | Ruiz et al. |
| 2017/0067014 A1 | 3/2017 | Takebe et al. |
| 2017/0073639 A1 | 3/2017 | Eilertsen et al. |
| 2017/0081398 A1 | 3/2017 | Boone et al. |
| 2017/0087189 A1 | 3/2017 | Evans et al. |
| 2017/0087275 A1 | 3/2017 | Christman et al. |
| 2017/0088635 A1 | 3/2017 | Chang et al. |
| 2017/0089887 A1 | 3/2017 | Souza et al. |

OTHER PUBLICATIONS

De Carlo et al. (2010, Int. J. Mol. Med., vol. 25, pp. 195-202) (Year: 2010).*
Kim et al. (2016, Scientific Reports, vol. 6:35145, pp. 1-13) (Year: 2016).*
Cheng et al. (2011, Tissue Engineering, vol. 17(4), pp. 235-247) (Year: 2011).*

* cited by examiner

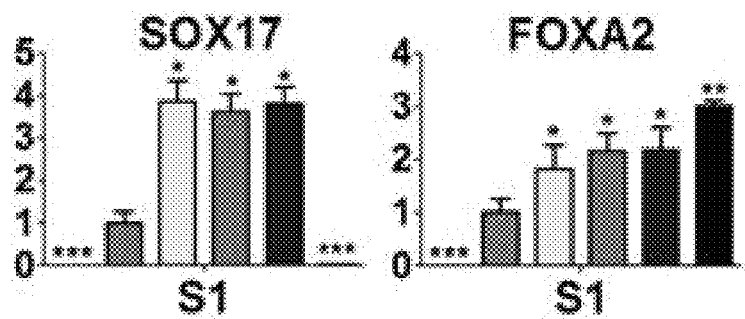
Fig. 2A
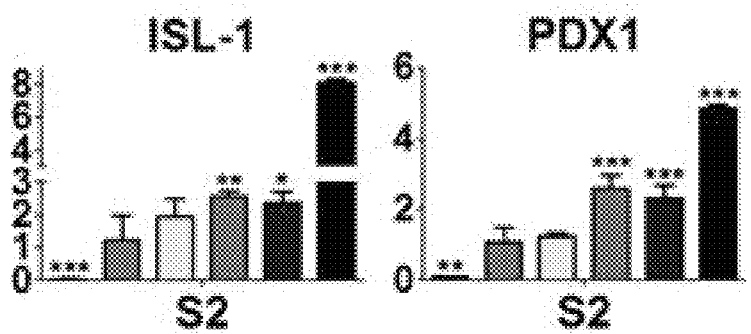
Fig. 2B
Fig. 2C

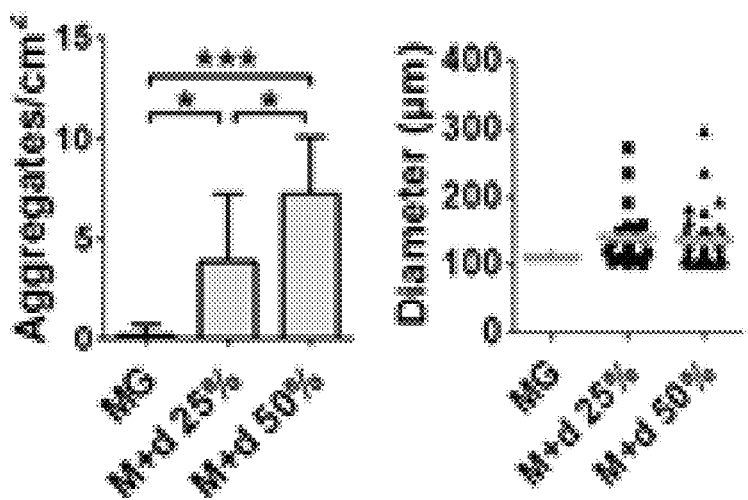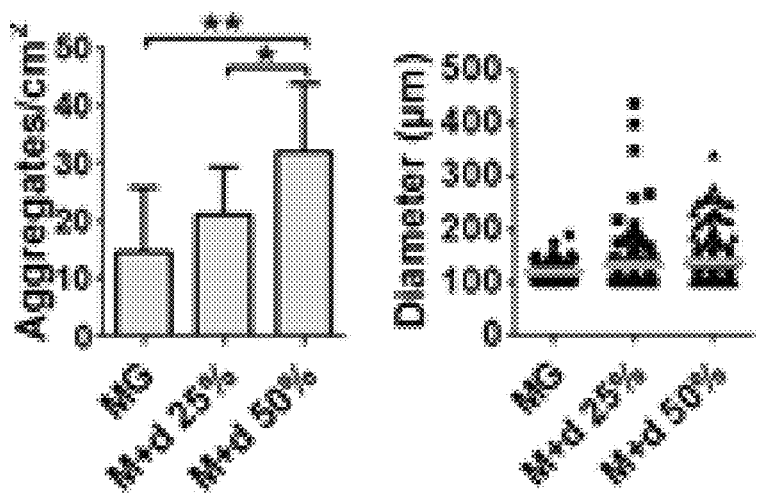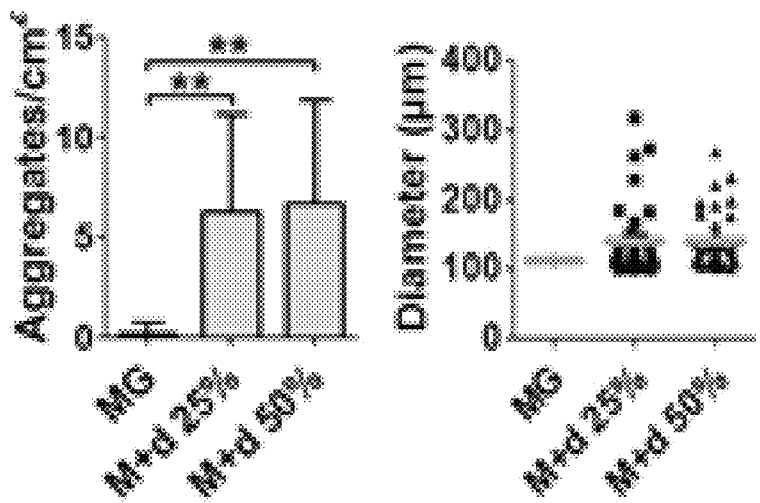
Fig. 3B    Fig. 3C

IMR90 S5 2D

IMR90 S5 Aggregates

H9 S5 2D

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: SOX17 Forward Primer

<400> SEQUENCE: 1
cagcagaatc cagacctgca                                                  20

<210> SEQ ID NO 2
<211> LENGTH: 19
<212> TYPE: DNA
<213> ORGANISM: Artificial Sequence
<220> FEATURE:
<223> OTHER INFORMATION: SOX17 Reverse Primer

<400> SEQUENCE: 2
gtcagcgcct tccacgact                                                   19

<210> SEQ ID NO 3
<211> LENGTH: 24
<212> TYPE: DNA
<213> ORGANISM: Artificial Sequence
<220> FEATURE:
<223> OTHER INFORMATION: SOX17 Probe FAM-Probe-BHQ

<400> SEQUENCE: 3
```

```
acgccgagtt gagcaagatg ctgg                                          24

<210> SEQ ID NO 4
<211> LENGTH: 21
<212> TYPE: DNA
<213> ORGANISM: Artificial Sequence
<220> FEATURE:
<223> OTHER INFORMATION: FOXA2 Forward Primer

<400> SEQUENCE: 4
ccgactggag cagctactat g                                             21

<210> SEQ ID NO 5
<211> LENGTH: 20
<212> TYPE: DNA
<213> ORGANISM: Artificial Sequence
<220> FEATURE:
<223> OTHER INFORMATION: FOXA2 Reverse Primer

<400> SEQUENCE: 5
tacgtgttca tgccgttcat                                               20

<210> SEQ ID NO 6
<211> LENGTH: 23
<212> TYPE: DNA
<213> ORGANISM: Artificial Sequence
<220> FEATURE:
<223> OTHER INFORMATION: FOXA2 Probe FAM-Probe-BHQ

<400> SEQUENCE: 6
cagagcccga gggctactcc tcc                                           23

<210> SEQ ID NO 7
<211> LENGTH: 20
<212> TYPE: DNA
<213> ORGANISM: Artificial Sequence
<220> FEATURE:
<223> OTHER INFORMATION: PDX-1 Forward Primer

<400> SEQUENCE: 7
cctttcccat ggatgaagtc                                               20

<210> SEQ ID NO 8
<211> LENGTH: 18
<212> TYPE: DNA
<213> ORGANISM: Artificial Sequence
<220> FEATURE:
<223> OTHER INFORMATION: PDX-1 Reverse Primer

<400> SEQUENCE: 8
cgtccgcttg ttctcctc                                                 18

<210> SEQ ID NO 9
<211> LENGTH: 21
<212> TYPE: DNA
<213> ORGANISM: Artificial Sequence
<220> FEATURE:
<223> OTHER INFORMATION: PDX-1 Probe FAM-Probe-BHQ

<400> SEQUENCE: 9
aagctcacgc gtggaaaggc c                                             21

<210> SEQ ID NO 10
<211> LENGTH: 18
<212> TYPE: DNA
<213> ORGANISM: Artificial Sequence
```

```
<220> FEATURE:
<223> OTHER INFORMATION: PTF1A Forward Primrer

<400> SEQUENCE: 10
caggcccaga aggtcatc                                                       18

<210> SEQ ID NO 11
<211> LENGTH: 18
<212> TYPE: DNA
<213> ORGANISM: Artificial Sequence
<220> FEATURE:
<223> OTHER INFORMATION: PTF1A Reverse Primer

<400> SEQUENCE: 11
gggagggagg ccataatc                                                       18

<210> SEQ ID NO 12
<211> LENGTH: 19
<212> TYPE: DNA
<213> ORGANISM: Artificial Sequence
<220> FEATURE:
<223> OTHER INFORMATION: PTF1A Probe FAM-Probe-BHQ

<400> SEQUENCE: 12
atctgccatc ggggcaccc                                                      19

<210> SEQ ID NO 13
<211> LENGTH: 17
<212> TYPE: DNA
<213> ORGANISM: Artificial Sequence
<220> FEATURE:
<223> OTHER INFORMATION: Insulin Forward Primer

<400> SEQUENCE: 13
gggaggcaga ggacctg                                                        17

<210> SEQ ID NO 14
<211> LENGTH: 18
<212> TYPE: DNA
<213> ORGANISM: Artificial Sequence
<220> FEATURE:
<223> OTHER INFORMATION: Insulin Reverse Primer

<400> SEQUENCE: 14
ccacaatgcc acgcttct                                                       18

<210> SEQ ID NO 15
<211> LENGTH: 20
<212> TYPE: DNA
<213> ORGANISM: Artificial Sequence
<220> FEATURE:
<223> OTHER INFORMATION: Insulin Probe FAM-Probe-BHQ

<400> SEQUENCE: 15
aggtggggca ggtggagctg                                                     20

<210> SEQ ID NO 16
<211> LENGTH: 20
<212> TYPE: DNA
<213> ORGANISM: Artificial Sequence
<220> FEATURE:
<223> OTHER INFORMATION: Glucagon Forward Primer

<400> SEQUENCE: 16
gctgccaagg aattcattgc                                                     20
```

```
<210> SEQ ID NO 17
<211> LENGTH: 22
<212> TYPE: DNA
<213> ORGANISM: Artificial Sequence
<220> FEATURE:
<223> OTHER INFORMATION: Glucagon Reverse Primer

<400> SEQUENCE: 17
cttcaacaat ggcgacctct tc                                          22

<210> SEQ ID NO 18
<211> LENGTH: 24
<212> TYPE: DNA
<213> ORGANISM: Artificial Sequence
<220> FEATURE:
<223> OTHER INFORMATION: Glucagon Probe FAM-Probe-BHQ

<400> SEQUENCE: 18
tgaaaggccg aggaaggcga gatt                                        24
```

MICROENVIRONMENTS FOR SELF-ASSEMBLY OF ISLET ORGANOIDS FROM STEM CELLS DIFFERENTIATION

CROSS REFERENCE TO RELATED APPLICATIONS

This application is a non-provisional of, and claims benefit of priority from, U.S. Provisional Patent Application No. 62/479,095, filed Mar. 30, 3017, the entirety of which is expressly incorporated herein by reference.

STATEMENT OF GOVERNMENT RIGHTS

This invention was made with government support under CBET1445387 awarded by the National Science Foundation. The government has certain rights in the invention.

BACKGROUND OF THE INVENTION

Each reference cited herein is expressly incorporated herein by reference in its entirety.

Diabetes mellitus is one of the most common chronic diseases worldwide characterized by progressive loss of functional insulin-producing $\beta$-cells, resulting in hyperglycemia associated with diabetic complications. It has been predicted that over 300 million people worldwide will be diagnosed with type I or type II diabetes by the year 2025 (Zimmet, Paul, K. G. M. M. Alberti, and Jonathan Shaw. "Global and societal implications of the diabetes epidemic." Nature 414, no. 6865 (2001): 782-787.). These diseases induce other diseases, such as heart disease and stroke, high blood pressure, kidney disease, and blindness. Type 1 diabetes results from autoimmune destruction of $\beta$-cells, leading to incapable of maintaining normoglycemia in these patients. Although type 2 diabetes is caused by the peripheral resistance to insulin and impaired insulin secretion, the late stages of this disease can induce a significant decrease in $\beta$-cell mass. Therefore, both type 1 and type 2 diabetic patients could benefit from $\beta$-cell replacement therapy. Islet transplantation has proven to be a cure to diabetes. Nevertheless, this treatment is unavailable to vast majority of patients due to the scarcity of human donors and transplant rejection. Thus, new sources of transplantable islets need to be identified.

While islet transplantation is promising, the supply of transplantable islet tissues remains a challenge. Great efforts have been made to generate biologically functional islet-like organoids from human pluripotent stem cells (hPSCs) for diabetes treatment.

Human pluripotent stem cells (hPSCs) have a great potential to become a major cell source to produce biologically functional insulin secreting $\beta$-cells for cell-based therapy. In spite of intense efforts made to enhance hPSC $\beta$-cell differentiation over the past decade, current approaches focus on generating insulin secreting $\beta$-cells, rather than islets or islet organoids. This is due to the fact that niches inducing in vitro self-assembly of islet organoids from hPSCs have NOT to be identified yet.

The pancreas arises from both dorsal and ventral portions of foregut endoderm [Y. Wen, S. Jin, Production of neural stem cells from human pluripotent stem cells, J Biotechnol 188 (2014) 122-9]. The formation of a multipotent pancreatic epithelium after a rapid growth of pancreatic buds from the foregut endoderm leads to the development of both pancreatic exocrine and endocrine structures that work intimately to regulate nutrient metabolism and blood glucose concentration. Distinct endocrine cells, including insulin (INS)-producing $\beta$ cells, glucagon (GCG)-producing $\alpha$ cells, somatostatin (SST)-producing $\delta$ cells, pancreatic polypeptide (PP)-producing PP cells, and ghrelin-producing $\epsilon$ cells, are organized into cell clusters forming the islets of Langerhans that are embedded in the glandular exocrine pancreas and are closely associated with microvasculature and neurovascular environments [S. Jin, H. Yao, P. Krisanarungson, A. Haukas, K. Ye, Porous membrane substrates offer better niches to enhance the Wnt signaling and promote human embryonic stem cell growth and differentiation, Tissue Eng Part A 18(13-14) (2012) 1419-30]. These development processes are highly regulated and controlled by many factors such as morphogens and key transcriptional regulators produced by surrounding embryonic development environments.

Most current knowledge about pancreogenesis during embryo development have been gleaned from studies using rodent models. Nevertheless, a line of evidence suggests significantly different developmental events occurred during human pancreogenesis as compared to those observed in mice [S. Jin, H. Yao, J. L. Weber, Z. K. Melkoumian, K. Ye, A synthetic, xeno-free peptide surface for expansion and directed differentiation of human induced pluripotent stem cells, PLoS One 7(11) (2012) e50880; Y. Stefan, L. Orci, F. Malaisse-Lagae, A. Perrelet, Y. Patel, R. H. Unger, Quantitation of endocrine cell content in the pancreas of nondiabetic and diabetic humans, Diabetes 31(8 Pt 1) (1982) 694-700; H. Ichii, L. Inverardi, A. Pileggi, R. D. Molano, O. Cabrera, A. Caicedo, S. Messinger, Y. Kuroda, P. O. Berggren, C. Ricordi, A novel method for the assessment of cellular composition and beta-cell viability in human islet preparations, Am J Transplant 5(7) (2005) 1635-45; M. Brissova, M. J. Fowler, W. E. Nicholson, A. Chu, B. Hirshberg, D. M. Harlan, A. C. Powers, Assessment of human pancreatic islet architecture and composition by laser scanning confocal microscopy, J Histochem Cytochem 53(9) (2005) 1087-97; T. A. Matsuoka, I. Artner, E. Henderson, A. Means, M. Sander, R. Stein, The MafA transcription factor appears to be responsible for tissue-specific expression of insulin, Proc Natl Acad Sci USA 101(9) (2004) 2930-3]. The distinct cytostructure between human and mouse islets further implies different developmental mechanisms adopted by the two species. In mice, $\beta$ cells form a core of the islets, while such a core structure does not exist in human islets. In human islets, $\beta$, $\alpha$, $\delta$, PP, and $\epsilon$ cells are mixed and connected with blood vessels, nerve fibers, and lymphatic vessels [C. Zhang, T. Moriguchi, M. Kajihara, R. Esaki, A. Harada, H. Shimohata, H. Oishi, M. Hamada, N. Morito, K. Hasegawa, T. Kudo, J. D. Engel, M. Yamamoto, S. Takahashi, MafA is a key regulator of glucose-stimulated insulin secretion, Mol Cell Biol 25(12) (2005) 4969-76; Pagliuca, Felicia W., Jeffrey R. Millman, Mads Gürtler, Michael Segel, Alana Van Dervort, Jennifer Hyoje Ryu, Quinn P. Peterson, Dale Greiner, and Douglas A. Melton. "Generation of functional human pancreatic $\beta$ cells in vitro." Cell 159, no. 2 (2014): 428-439; X. Wang, K. Ye, Three-dimensional differentiation of embryonic stem cells into islet-like insulin-producing clusters, Tissue Eng Part A 15(8) (2009) 1941-52]. Consequently, differentiation protocols developed based on mechanisms elucidated from animal studies might not be sufficient to generating biologically functional $\beta$ cells for cell-base diabetes treatment.

The generation of islet organoids has been attempted in the last decades. In previous work, the feasibility of assembly of islet-like cell clusters from pancreatic differentiated mouse embryonic stem cells (mESCs) within a collagen scaffold was demonstrated [Wang X, Ye K. Three-dimensional differentiation of embryonic stem cells into islet-like insulin-producing clusters. Tissue Eng Part A 15, 1941-1952 (2009)]. mESC-derived cell clusters were produced which consisted of α, β, and δ cells. They exhibited a characteristic mouse islet architecture that has a β cell core surrounded by a and δ cells. The islet-like cell clusters produced ATP-sensitive K$^+$ (KATP) channel dependent insulin secretion upon glucose challenging. However, no PP cells were detected in these cell clusters, suggesting that these cell clusters are distinct to adult islets. Built upon these findings, the generation of islet organoids (consisting all endocrine cells) from human embryonic stem cells (human ESCs, or hESCs) within a biomimetic scaffold was demonstrated [Wang W, Jin S, Ye K. Development of Islet Organoids from H9 Human Embryonic Stem Cells in Biomimetic 3D Scaffolds. Stem Cells Dev, (2016)]. The cytostructural analysis of these organoids revealed a typical architecture of human adult islets. These organoids consisted of α, β, δ, and PP cells. Both β cells and non-β cells were mixed randomly to form organoids that secrete insulin in response to glucose challenges.

A recent study reported by Kim et. al. suggested the therapeutic effects of ESC-derived islet-like organoids in a diabetic mouse model [Kim, Youngjin, Hyeongseok Kim, Ung Hyun Ko, Youjin Oh, Ajin Lim, Jong-Woo Sohn, Jennifer H. Shin, Hail Kim, and Yong-Mahn Han. "Islet-like organoids derived from human pluripotent stem cells efficiently function in the glucose responsiveness in vitro and in vivo." Scientific reports 6 (2016): 35145]. Their animal studies suggested the possibility of suppressing hyperglycemia in Streptozotocin (STZ)-induced diabetic mice after islet-like organoid transplantation. However, the normalization of blood glucose level in these transplanted mice only lasted 40 days. The long-term therapeutic benefits of these cell clusters has not been demonstrated. The analysis of the cytostructure of these islet-like organoids revealed insufficient endocrine cell composition. No α cells and only very few δ cells were detected in these cell clusters. The detection of pancreatic endocrine marker gene expression indicated a low level of expression of Nkx6.1, a mature gene marker of β cells in these islet-like organoids. The expression of MAFB was also detected in these cell clusters, further suggesting their immaturity.

The study reported by Pagliuca et al. represented a success in generating functional human pancreatic β cells from human pluripotent stem cells (HPSCs) in a suspension culture [Pagliuca F W, et al. Generation of functional human pancreatic beta cells in vitro. Cell 159, 428-439 (2014)]. The transplantation of these insulin-secreting cells in diabetic mice led to long-term glycemic control, suggesting potential use of these cells for diabetes therapy [Vegas A J, et al. Long-term glycemic control using polymer-encapsulated human stem cell-derived beta cells in immune-competent mice. Nat Med 22, 306-311 (2016)]. In their study, they discovered that cell clusters were formed after culturing hPSC-derived INS+/NKX6.1+ cells in a suspension culture. The size of these cell clusters was around ~200 μm that is larger than human islets (~100 μm). No PP cells were detected in these cell clusters. Only minor populations of α and δ cells were found in these cell clusters, as compared to adult islets which contains roughly 20% α-cells, 10% δ cells, and <5% PP cells [Stefan Y, Orci L, Malaisse-Lagae F, Perrelet A, Patel Y, Unger R H. Quantitation of endocrine cell content in the pancreas of nondiabetic and diabetic humans. Diabetes 31, 694-700 (1982); Ichii H, et al. A novel method for the assessment of cellular composition and beta-cell viability in human islet preparations. Am J Transplant 5, 1635-1645 (2005); Brissova M, et al. Assessment of human pancreatic islet architecture and composition by laser scanning confocal microscopy. J Histochem Cytochem 53, 1087-1097 (2005)]. The population of both α and δ cells in cell clusters increased after grafting, suggesting the further maturation of these cell clusters in vivo.

The generation of islet-like cell clusters from either human ESCs or iPSCs has been investigated in a number of studies including the use of miR-186 and miR-375 to enhance differentiation of iPSCs into islet-like cell clusters [Wang X, Ye K. Three-dimensional differentiation of embryonic stem cells into islet-like insulin-producing clusters. Tissue Eng Part A 15, 1941-1952 (2009); Jiang J, et al. Generation of insulin-producing islet-like clusters from human embryonic stem cells. Stem Cells 25, 1940-1953 (2007); Tateishi K, He J, Taranova O, Liang G, D'Alessio A C, Zhang Y. Generation of insulin-secreting islet-like clusters from human skin fibroblasts. J Biol Chem 283, 31601-31607 (2008); Shaer A, Azarpira N, Karimi M H. Differentiation of human induced pluripotent stem cells into insulin-like cell clusters with miR-186 and miR-375 by using chemical transfection. Appl Biochem Biotechnol 174, 242-258 (2014); Shaer A, Azarpira N, Vandati A, Karimi M H, Shariati M. Differentiation of human-induced pluripotent stem cells into insulin-producing clusters. Exp Clin Transplant 13, 68-75 (2015); Ionescu-Tirgoviste C, et al. A 3D map of the islet routes throughout the healthy human pancreas. Sci Rep 5, 14634 (2015); Rezania A, et al. Reversal of diabetes with insulin-producing cells derived in vitro from human pluripotent stem cells. Nat Biotechnol 32, 1121-1133 (2014)]. In light of these successes, cytostructure and endocrine cell compositions of these cell clusters are distinct markedly from adult islets. In particular, no PP cells are detected from these cell clusters. Most endocrine cells in these cell clusters express multiple hormones such as INS and GCG, similar to marker gene expression patterns detected in pancreatic endocrine progenitors. Shim, et. al. showed that the INS+/GCG+ cells disappeared after cell cluster grafting in STZ-induced diabetic mice, presumptively due to in vivo maturation of these cell clusters [Shim J H, et al. Pancreatic Islet-Like Three-Dimensional Aggregates Derived From Human Embryonic Stem Cells Ameliorate Hyperglycemia in Streptozotocin-Induced Diabetic Mice. Cell Transplant 24, 2155-2168 (2015)]. The generation of islet-like cell clusters from human umbilical cord mesenchymal stem cells has also been explored [Chao K C, Chao K F, Fu Y S, Liu S H. Islet-like clusters derived from mesenchymal stem cells in Wharton's Jelly of the human umbilical cord for transplantation to control type 1 diabetes. PLoS One 3, e1451 (2008)].

In addition, extensive efforts have made to generate glucose-responsive, insulin-secreting β cells in last two decades [Pagliuca F W, et al. Generation of functional human pancreatic beta cells in vitro. Cell 159, 428-439 (2014); Rezania A, et al. Reversal of diabetes with insulin-producing cells derived in vitro from human pluripotent stem cells. Nat Biotechnol 32, 1121-1133 (2014); Russ H A, et al. Controlled induction of human pancreatic progenitors produces functional beta-like cells in vitro. EMBO J 34, 1759-1772 (2015); Takeuchi H, Nakatsuji N, Suemori H. Endodermal differentiation of human pluripotent stem cells to insulin-producing cells in 3D culture. Sci Rep 4, 4488 (2014); Rajaei B, Shamsara M, Massumi M, Sanati M H. Pancreatic Endoderm-Derived from Diabetic Patient-Specific Induced Pluripotent Stem Cell Generates Glucose-Responsive Insulin-Secreting Cells. J Cell Physiol, (2016);

Fotino N, Fotino C, Pileggi A. Re-engineering islet cell transplantation. *Pharmacol Res* 98, 76-85 (2015); D'Amour K A, et al. Production of pancreatic hormone-expressing endocrine cells from human embryonic stem cells. *Nat Biotechnol* 24, 1392-1401 (2006); Rezania A, et al. Enrichment of human embryonic stem cell-derived NKX6.1-expressing pancreatic progenitor cells accelerates the maturation of insulin-secreting cells in vivo. *Stem Cells* 31, 2432-2442 (2013); Jiang W, et al. In vitro derivation of functional insulin-producing cells from human embryonic stem cells. *Cell Res* 17, 333-344 (2007); Zhu S, et al. Human pancreatic beta-like cells converted from fibroblasts. *Nat Commun* 7, 10080 (2016)]. Growing evidences suggest that islet structure is critical to the maturation of β cells during pancreatic organogenesis [Li Y, Xu C, Ma T. In vitro organogenesis from pluripotent stem cells. *Organogenesis* 10, 159-163 (2014)]. The heterotypic contact between α and β cells in human islets suggests paramount role of α cells to β cells during their maturation and glucose-responsive insulin-secretion [Nair G, Hebrok M. Islet formation in mice and men: lessons for the generation of functional insulin-producing beta-cells from human pluripotent stem cells. *Curr Opin Genet Dev* 32, 171-180 (2015); Halban P A. Cellular sources of new pancreatic beta cells and therapeutic implications for regenerative medicine. *Nat Cell Biol* 6, 1021-1025 (2004); Rorsman P, Braun M. Regulation of insulin secretion in human pancreatic islets. *Annu Rev Physiol* 75, 155-179 (2013)]. The formation of gap junctions during cell-cell coupling has been found crucial to functional mature of β cells [Carvalho C P, et al. Beta cell coupling and connexin expression change during the functional maturation of rat pancreatic islets. *Diabetologia* 53, 1428-1437 (2010); Benninger R K, Piston D W. Cellular communication and heterogeneity in pancreatic islet insulin secretion dynamics. *Trends Endocrinol Metab* 25, 399-406 (2014)]. Accordingly, the composition and relative proportion of islet cells have profound effect in regulating pancreatic endocrine cell maturation and their physiological functions in vivo, which necessitates the formation of islets or islet organoids consisting of all islet cell types.

See, U.S. Pat. Nos. 5,429,938; 5,549,674; 5,646,035; 5,686,289; 5,695,998; 5,747,341; 5,780,299; 5,780,300; 5,800,537; 5,821,121; 5,849,585; 5,861,313; 5,866,414; 5,888,816; 5,902,577; 5,928,942; 6,008,047; 6,020,200; 6,022,863; 6,051,750; 6,060,270; 6,087,157; 6,149,902; 6,197,575; 6,326,201; 6,372,493; 6,398,819; 6,410,320; 6,413,735; 6,455,311; 6,485,723; 6,541,224; 6,552,016; 6,610,535; 6,623,941; 6,759,039; 6,821,484; 6,878,806; 6,900,051; 6,902,881; 6,905,688; 6,908,732; 6,919,433; 6,926,898; 6,946,134; 6,946,293; 6,951,924; 6,962,814; 6,969,519; 7,015,037; 7,026,447; 7,064,185; 7,101,546; 7,112,410; 7,135,336; 7,141,547; 7,164,004; 7,175,841; 7,189,690; 7,196,164; 7,211,434; 7,217,570; 7,217,788; 7,238,660; 7,238,667; 7,244,707; 7,247,477; 7,300,929; 7,301,016; 7,312,241; 7,326,570; 7,351,729; 7,354,763; 7,355,008; 7,368,527; 7,368,531; 7,371,388; 7,371,576; 7,381,800; 7,390,637; 7,396,809; 7,413,897; 7,416,885; 7,425,619; 7,425,620; 7,452,964; 7,468,446; 7,469,185; 7,470,723; 7,482,013; 7,485,297; 7,497,686; 7,498,027; 7,498,168; 7,501,123; 7,507,413; 7,507,414; 7,510,873; 7,521,424; 7,521,540; 7,521,542; 7,534,608; 7,560,276; 7,563,619; 7,569,384; 7,582,292; 7,588,936; 7,592,010; 7,601,525; 7,604,991; 7,615,373; 7,632,497; 7,632,679; 7,648,964; 7,655,674; 7,659,118; 7,670,797; 7,695,965; 7,723,112; 7,745,216; 7,754,483; 7,759,113; 7,771,717; 7,776,592; 7,776,597; 7,781,179; 7,785,599; 7,799,759; 7,799,898; 7,803,377; 7,807,459; 7,807,641; 7,811,819; 7,838,503; 7,838,636; 7,847,079; 7,875,272; 7,883,847; 7,883,892; 7,910,555; 7,914,779; 7,939,322; 7,951,362; 7,960,512; 7,977,306; 7,985,537; 7,993,920; 8,003,774; 8,008,075; 8,012,464; 8,022,178; 8,030,025; 8,044,180; 8,053,456; 8,067,377; 8,071,539; 8,075,881; 8,084,258; 8,106,083; 8,110,400; 8,129,182; 8,133,982; 8,137,662; 8,143,026; 8,147,824; 8,148,149; 8,173,361; 8,183,384; 8,187,593; 8,187,878; 8,192,737; 8,193,318; 8,197,815; 8,198,255; 8,211,439; 8,211,697; 8,211,867; 8,216,574; 8,217,147; 8,221,749; 8,222,253; 8,236,761; 8,247,423; 8,252,280; 8,252,739; 8,252,764; 8,252,915; 8,273,570; 8,278,095; 8,287,859; 8,299,107; 8,299,212; 8,303,972; 8,318,483; 8,318,790; 8,329,467; 8,329,736; 8,334,365; 8,337,829; 8,354,397; 8,357,528; 8,357,690; 8,361,459; 8,377,689; 8,404,242; 8,409,859; 8,410,246; 8,415,153; 8,415,377; 8,445,273; 8,445,645; 8,450,500; 8,460,864; 8,460,929; 8,470,308; 8,470,309; 8,470,599; 8,481,308; 8,486,932; 8,513,189; 8,518,390; 8,524,712; 8,530,627; 8,540,978; 8,551,779; 8,562,969; 8,586,345; 8,603,811; 8,609,406; 8,623,648; 8,642,336; 8,642,339; 8,648,071; 8,652,466; 8,680,067; 8,685,390; 8,685,720; 8,685,730; 8,691,523; 8,697,071; 8,703,121; 8,703,424; 8,703,483; 8,709,402; 8,710,017; 8,716,465; 8,722,034; 8,728,813; 8,735,154; 8,741,643; 8,741,646; 8,742,133; 8,748,171; 8,748,424; 8,753,638; 8,765,390; 8,765,470; 8,772,275; 8,778,899; 8,784,772; 8,784,808; 8,785,184; 8,785,185; 8,785,599; 8,785,658; 8,802,438; 8,815,584; 8,815,587; 8,815,591; 8,822,684; 8,828,433; 8,828,685; 8,828,721; 8,835,168; 8,835,464; 8,836,218; 8,841,123; 8,846,859; 8,852,934; 8,853,162; 8,859,286; 8,877,181; 8,877,497; 8,883,160; 8,883,506; 8,895,048; 8,895,300; 8,906,360; 8,911,690; 8,911,953; 8,916,686; 8,927,548; 8,937,094; 8,940,292; 8,946,156; 8,946,387; 8,951,517; 8,968,730; 8,969,301; 8,969,538; 8,993,517; 9,005,897; 9,005,962; 9,005,964; 9,006,277; 9,012,218; 9,018,005; 9,028,815; 9,029,147; 9,040,694; 9,056,093; 9,062,290; 9,062,346; 9,066,930; 9,067,884; 9,068,169; 9,080,145; 9,085,756; 9,096,832; 9,096,877; 9,101,690; 9,115,191; 9,120,745; 9,125,906; 9,126,953; 9,127,268; 9,133,439; 9,150,833; 9,150,857; 9,151,744; 9,151,760; 9,156,836; 9,157,069; 9,163,216; 9,173,869; 9,175,089; 9,181,301; 9,181,528; 9,186,388; 9,206,162; 9,221,896; 9,234,176; 9,234,178; 9,267,936; 9,267,938; 9,278,159; 9,284,531; 9,289,453; 9,296,809; 9,308,238; 9,315,794; 9,328,340; 9,365,830; 9,365,851; 9,371,516; 9,388,381; 9,388,387; 9,394,522; 9,404,087; 9,404,140; 9,409,995; 9,415,086; 9,434,920; 9,447,378; 9,447,380; 9,453,205; 9,458,430; 9,458,471; 9,476,030; 9,481,894; 9,487,750; 9,489,474; 9,493,845; 9,498,501; 9,499,789; 9,499,793; 9,504,719; 9,506,036; 9,506,062; 9,526,747; 9,527,912; 9,528,090; 9,534,203; 9,539,243; 9,540,613; 9,540,628; 9,546,379; 9,550,838; 9,555,007; 9,579,351; 9,580,688; 9,585,917; 9,585,918; 9,592,256; 9,592,258; 9,593,305; 9,593,306; 9,593,307; 9,605,244; 9,605,265; RE43876; 20010000324; 20020006640; 20020012653; 20020012966; 20020042096; 20020042386; 20020045230; 20020061521; 20020064818; 20020064829; 20020076756; 20020077270; 20020077287; 20020081725; 20020086330; 20020086353; 20020086811; 20020086820; 20020086821; 20020086822; 20020086823; 20020090615; 20020090672; 20020090673; 20020090674; 20020094953; 20020099085; 20020102638; 20020106736; 20020119566; 20020119919; 20020120103; 20020132753; 20020132767; 20020147140; 20020150986; 20020151056; 20020151479; 20020155598; 20020161208; 20020164685; 20020164791; 20020165137; 20020165221; 20020168711; 20020172994; 20020173454; 20030003088; 20030013649; 20030027330; 20030027776; 20030027999; 20030036505;

20030039993; 20030039994; 20030044890; 20030044904; 20030044905; 20030044907; 20030044976; 20030045459; 20030049618; 20030049650; 20030049652; 20030049703; 20030050231; 20030050455; 20030054368; 20030054373; 20030054375; 20030054377; 20030054379; 20030054420; 20030059875; 20030059908; 20030068627; 20030077602; 20030077606; 20030077703; 20030077704; 20030077808; 20030082681; 20030082758; 20030083481; 20030092102; 20030092611; 20030092615; 20030096346; 20030103950; 20030108907; 20030109690; 20030113840; 20030113910; 20030124721; 20030125246; 20030129685; 20030139327; 20030143191; 20030152933; 20030157508; 20030161817; 20030166541; 20030166864; 20030170215; 20030171252; 20030171267; 20030175739; 20030175858; 20030181692; 20030190707; 20030191298; 20030194708; 20030194802; 20030199008; 20030199043; 20030203361; 20030207285; 20030215893; 20030219758; 20030219875; 20030220489; 20030224376; 20030224461; 20030225009; 20030232752; 20030232975; 20030235563; 20030235829; 20030235831; 20040002124; 20040002591; 20040005575; 20040005577; 20040005579; 20040009488; 20040009491; 20040009589; 20040010121; 20040010132; 20040010134; 20040014039; 20040018621; 20040018623; 20040023949; 20040031067; 20040033599; 20040034196; 20040037813; 20040044191; 20040048296; 20040052771; 20040058443; 20040067882; 20040067953; 20040071687; 20040101927; 20040110287; 20040115805; 20040127406; 20040132183; 20040141957; 20040146893; 20040161419; 20040171123; 20040175367; 20040185045; 20040191901; 20040208869; 20040208870; 20040224302; 20040224887; 20040225113; 20040228846; 20040235113; 20040241803; 20040242469; 20040242482; 20040247567; 20040253672; 20040259244; 20040266674; 20050002915; 20050013870; 20050014727; 20050019866; 20050031598; 20050032168; 20050037000; 20050037022; 20050037467; 20050037490; 20050048490; 20050054051; 20050054098; 20050054102; 20050054570; 20050064514; 20050074875; 20050080138; 20050085519; 20050090465; 20050100549; 20050100991; 20050107339; 20050112106; 20050147593; 20050147960; 20050153443; 20050158859; 20050176061; 20050181371; 20050181502; 20050186664; 20050191743; 20050196423; 20050197285; 20050208565; 20050208602; 20050208619; 20050208653; 20050214786; 20050215767; 20050222087; 20050239059; 20050244388; 20050244931; 20050255588; 20050260213; 20050260750; 20050266532; 20050266533; 20050266555; 20050277190; 20060003380; 20060008450; 20060013810; 20060014254; 20060025406; 20060030041; 20060030042; 20060052596; 20060057138; 20060057542; 20060057582; 20060068496; 20060073561; 20060084082; 20060084167; 20060084794; 20060093586; 20060094046; 20060099575; 20060110830; 20060122104; 20060134709; 20060165666; 20060166329; 20060171930; 20060177439; 20060194321; 20060194735; 20060198827; 20060222634; 20060223077; 20060223177; 20060246483; 20060246488; 20060257965; 20060258586; 20060263337; 20060269908; 20060270032; 20060275900; 20060276396; 20060281174; 20060281179; 20060286635; 20070003526; 20070003529; 20070009494; 20070009521; 20070009882; 20070014771; 20070015162; 20070015271; 20070015279; 20070015696; 20070015908; 20070020724; 20070021493; 20070026013; 20070026454; 20070027306; 20070031842; 20070031966; 20070032413; 20070032414; 20070036767; 20070036799; 20070037206; 20070042361; 20070048282; 20070048297; 20070048818; 20070053996; 20070054319; 20070055056; 20070065942; 20070072292; 20070099297; 20070099833; 20070104697; 20070111203; 20070111306; 20070122903; 20070149571; 20070160586; 20070166824; 20070185024; 20070190068; 20070190165; 20070207522; 20070224650; 20070238169; 20070244047; 20070248947; 20070254319; 20070254359; 20070259421; 20070259815; 20070261127; 20070280948; 20070281355; 20070287173; 20070292389; 20070298491; 20080004206; 20080004277; 20080019950; 20080027147; 20080031820; 20080038352; 20080044417; 20080044429; 20080064049; 20080076176; 20080089931; 20080090887; 20080103606; 20080112961; 20080114061; 20080131399; 20080131435; 20080131966; 20080138344; 20080138349; 20080146503; 20080153751; 20080159999; 20080160617; 20080161243; 20080167238; 20080167239; 20080167240; 20080175828; 20080176840; 20080182278; 20080188406; 20080194023; 20080194481; 20080199849; 20080213886; 20080220453; 20080227714; 20080233649; 20080261877; 20080267926; 20080267962; 20080269125; 20080269126; 20080269127; 20080269128; 20080286867; 20080293629; 20080299655; 20090004152; 20090017023; 20090017024; 20090017026; 20090017027; 20090029914; 20090042792; 20090042875; 20090047212; 20090053218; 20090053238; 20090074771; 20090075381; 20090075880; 20090076251; 20090081228; 20090092586; 20090092610; 20090093402; 20090098124; 20090099073; 20090104159; 20090104163; 20090105140; 20090111177; 20090123430; 20090162329; 20090162437; 20090170198; 20090191159; 20090202537; 20090202977; 20090203129; 20090203130; 20090203635; 20090220996; 20090221072; 20090226447; 20090227533; 20090232808; 20090233353; 20090233354; 20090246178; 20090247540; 20090269845; 20090274663; 20090285816; 20090285883; 20090298169; 20090304646; 20090325293; 20100010068; 20100015100; 20100015150; 20100015711; 20100028306; 20100028307; 20100034791; 20100048472; 20100068190; 20100069386; 20100086525; 20100093627; 20100105100; 20100112691; 20100113447; 20100119496; 20100120069; 20100129351; 20100136688; 20100150876; 20100166713; 20100169990; 20100172994; 20100189686; 20100196361; 20100196362; 20100209396; 20100209467; 20100210013; 20100233239; 20100234273; 20100240130; 20100247601; 20100249026; 20100254944; 20100254996; 20100255580; 20100260728; 20100267079; 20100267135; 20100267814; 20100285031; 20100285584; 20100286048; 20100291033; 20100292177; 20100297149; 20100297210; 20100297757; 20100298331; 20100310576; 20110002888; 20110002897; 20110008298; 20110008887; 20110008892; 20110009312; 20110014160; 20110014163; 20110014692; 20110014702; 20110020380; 20110021607; 20110033928; 20110045045; 20110064701; 20110077256; 20110081654; 20110104805; 20110105483; 20110124032; 20110135610; 20110144103; 20110151561; 20110152310; 20110158905; 20110177042; 20110182879; 20110189140; 20110195094; 20110195503; 20110212067; 20110224206; 20110224223; 20110243941; 20110250686; 20110251150; 20110265197; 20110274662; 20110280830; 20110287071; 20110288026; 20110293611; 20110301209; 20110305714; 20110312019; 20110318389; 20110319447; 20120003736; 20120009186; 20120009203; 20120009675; 20120021513; 20120021985; 20120028355; 20120034237; 20120034692; 20120039955; 20120045830; 20120046221; 20120046288; 20120046346; 20120052568; 20120052571; 20120052576; 20120058562; 20120064047; 20120064537; 20120100115; 20120101072; 20120115226; 20120121554; 20120121560; 20120122869; 20120135043; 20120141415; 20120141449; 20120141476; 20120142093; 20120148540; 20120149051; 20120156250; 20120159655; 20120190111; 20120190112; 20120196312; 20120196365; 20120202813; 20120216304; 20120219535; 20120219551; 20120225073; 20120230966; 20120252732; 20120253102; 20120258122; 20120263711; 20120264209; 20120270319; 20120276094; 20120288564; 20120288936; 20120295962;

20120301444; 20120315251; 20120322864; 20120322865; 20130029416; 20130029875; 20130029911; 20130031645; 20130034525; 20130040853; 20130045187; 20130052177; 20130058900; 20130061340; 20130061342; 20130071363; 20130071364; 20130072461; 20130072489; 20130072564; 20130084281; 20130095567; 20130102023; 20130102533; 20130108606; 20130108630; 20130115197; 20130115695; 20130122586; 20130137650; 20130150296; 20130157933; 20130184817; 20130190350; 20130202563; 20130202606; 20130209427; 20130210060; 20130224116; 20130231294; 20130243766; 20130251687; 20130260385; 20130261164; 20130263297; 20130266553; 20130266939; 20130273045; 20130273083; 20130280230; 20130280719; 20130280802; 20130287744; 20130296378; 20130303493; 20130330822; 20130333059; 20130336938; 20130336992; 20130337561; 20130337562; 20130337564; 20130345219; 20130347133; 20140004095; 20140004121; 20140010789; 20140010798; 20140011278; 20140023624; 20140024116; 20140030786; 20140038291; 20140044754; 20140045263; 20140073527; 20140080210; 20140105888; 20140134162; 20140134733; 20140141509; 20140154801; 20140178450; 20140179596; 20140186305; 20140193373; 20140206854; 20140212395; 20140219997; 20140234957; 20140235479; 20140242038; 20140243227; 20140248238; 20140255861; 20140255969; 20140256037; 20140271566; 20140271843; 20140273069; 20140274953; 20140288301; 20140289877; 20140296186; 20140302491; 20140302601; 20140303077; 20140308746; 20140315753; 20140328794; 20140329315; 20140329318; 20140329321; 20140329704; 20140349397; 20140356951; 20140363886; 20140370515; 20140371222; 20140371294; 20150005299; 20150017134; 20150017135; 20150017727; 20150023911; 20150023934; 20150023964; 20150024458; 20150030636; 20150030657; 20150050298; 20150051203; 20150056647; 20150064784; 20150086512; 20150087627; 20150118193; 20150119395; 20150119475; 20150125507; 20150125953; 20150126451; 20150126499; 20150132277; 20150132355; 20150132846; 20150140072; 20150147301; 20150159139; 20150160246; 20150164784; 20150165227; 20150183771; 20150202235; 20150203568; 20150212065; 20150218522; 20150225698; 20150238530; 20150238656; 20150240212; 20150247124; 20150247194; 20150252323; 20150252327; 20150252349; 20150258145; 20150259396; 20150265656; 20150265657; 20150266858; 20150267167; 20150275168; 20150275171; 20150284689; 20150290249; 20150301025; 20150301058; 20150329619; 20150329821; 20150329829; 20150344574; 20150344575; 20150359823; 20150361401; 20150366885; 20150368616; 20150368667; 20150376574; 20160000789; 20160000834; 20160002595; 20160009724; 20160010055; 20160017288; 20160017290; 20160030359; 20160030638; 20160032249; 20160038544; 20160040130; 20160045498; 20160046903; 20160046941; 20160053229; 20160053318; 20160058794; 20160061817; 20160068580; 20160069865; 20160083693; 20160089371; 20160096036; 20160101133; 20160108363; 20160115444; 20160115448; 20160120911; 20160122708; 20160122722; 20160122803; 20160130561; 20160137986; 20160152674; 20160152687; 20160152949; 20160160182; 20160160184; 20160161486; 20160161488; 20160177270; 20160177273; 20160186259; 20160213717; 20160223555; 20160228506; 20160230163; 20160237401; 20160244751; 20160250262; 20160251627; 20160252494; 20160252524; 20160256499; 20160257937; 20160272723; 20160272944; 20160274121; 20160281062; 20160289642; 20160297868; 20160298088; 20160304823; 20160304839; 20160313306; 20160326491; 20160340440; 20160341726; 20160355787; 20160361466; 20160363584; 20160367695; 20160369238; 20160376557; 20170002091; 20170002313; 20170002327; 20170009211; 20170009212; 20170016886; 20170027994; 20170029778; 20170029783; 20170037354; 20170044570; 20170045497; 20170067014; 20170073639; 20170081398; 20170087189; 20170087275; 20170088635; 20170089887, each of which is expressly incorporated herein by reference in its entirety.

Youngjin Kim, Hyeongseok Kim, Ung Hyun Ko, Youjin Oh, Ajin Lim, Jong-Woo Sohn, Jennifer H. Shin, Hail Kim, and Yong-Mahn Han, "Islet-like organoids derived from human pluripotent stem cells efficiently function in the glucose responsiveness in vitro and in vivo", Sci Rep. 2016; 6: 35145, 2016 Oct. 12, doi: 10.1038/srep35145, PMCID: PMC5059670, reports that insulin secretion is elaborately modulated in pancreatic β cells within islets of three-dimensional (3D) structures. Using human pluripotent stem cells (hPSCs) to develop islet-like structures with insulin-producing β cells for the treatment of diabetes is challenging. Pancreatic islet-like clusters derived from hESCs are functionally capable of glucose-responsive insulin secretion as well as therapeutic effects. Pancreatic hormone-expressing endocrine cells (ECs) were differentiated from hESCs using a step-wise protocol. The hESC-derived ECs expressed pancreatic endocrine hormones, such as insulin, somatostatin, and pancreatic polypeptide. Notably, dissociated ECs autonomously aggregated to form islet-like, 3D structures of consistent sizes (100-150 μm in diameter). These EC clusters (ECCs) enhanced insulin secretion in response to glucose stimulus and potassium channel inhibition in vitro. Furthermore, β cell-deficient mice transplanted with ECCs survived for more than 40 d while retaining a normal blood glucose level to some extent. The expression of pancreatic endocrine hormones was observed in tissues transplanted with ECCs. In addition, ECCs could be generated from human induced pluripotent stem cells. These results suggest that hPSC-derived, islet-like clusters may be alternative therapeutic cell sources for treating diabetes.

US 2007/0037281, expressly incorporated herein by reference in its entirety, discusses a method for differentiating stem cells in cells that produce a pancreatic hormone. See, WO02/059278.

See also, Stendahl, John C., Dixon B. Kaufman, and Samuel I. Stupp. "Extracellular matrix in pancreatic islets: relevance to scaffold design and transplantation." Cell transplantation 18, no. 1 (2009): 1-12; Cheng, Jennifer Y C, Michael Raghunath, John Whitelock, and Laura Poole-Warren. "Matrix components and scaffolds for sustained islet function." Tissue Engineering Part B: Reviews 17, no. 4 (2011): 235-247; Stendahl, John C., Dixon B. Kaufman, and Samuel I. Stupp. "Extracellular matrix in pancreatic islets: relevance to scaffold design and transplantation." Cell transplantation 18, no. 1 (2009): 1-12; De Carlo, E., S. Baiguera, M. T. Conconi, S. Vigolo, C. Grandi, S. Lora, C. Martini et al. "Pancreatic acellular matrix supports islet survival and function in a synthetic tubular device: in vitro and in vivo studies." International journal of molecular medicine 25, no. 2 (2010): 195-202; Chen, Wenhui, Yasuhiko Tabata, and Yen Wah Tong. "Fabricating tissue engineering scaffolds for simultaneous cell growth and drug delivery." Current pharmaceutical design 16, no. 21 (2010): 2388-2394; Davis, Nicolynn E., Liese N. Beenken-Rothkopf, Annie Mirsoian, Nikola Kojic, David L. Kaplan, Annelise E. Barron, and Magali J. Fontaine. "Enhanced function of pancreatic islets co-encapsulated with ECM proteins and mesenchymal stromal cells in a silk hydrogel." Biomaterials 33, no. 28 (2012): 6691-6697; Coronel, Maria M., and Cherie L. Stabler. "Engineering a local microenvironment for pancreatic islet replacement." Current opinion in biotechnology 24, no. 5 (2013): 900-908; Yu, Yaling, Ali Alkhawaji, Yuqiang Ding, and Jin Mei. "Decellularized scaffolds in regenerative medicine." Oncotarget 7, no. 36 (2016): 58671; Rana, Deepti, Hala Zreiqat, Nadia Benkirane-Jessel, Seeram Ramakrishna, and Murugan Ramalingam. "Development of decellularized scaffolds for stem cell-driven tissue engineering." Journal of tissue engineering and regenerative medicine 11, no. 4 (2017): 942-965; Badylak, Stephen F., Doris Taylor, and Korkut Uygun. "Whole-organ tissue engineering: decellularization and recellularization of three-dimensional matrix scaffolds." Annual review of biomedical engineering 13 (2011): 27-53; Sabetkish, Shabnam, Abdol-Mohammad Kajbafzadeh, Nastaran Sabetkish, Reza Khorramirouz, Aram Akbarzadeh, Sanam Ladi Seyedian, Parvin Pasalar et al. "Whole-organ tissue engineering: Decellularization and recellularization of three-dimensional matrix liver scaffolds." Journal of Biomedical Materials Research Part A 103, no. 4 (2015): 1498-1508; Fu, Ru-Huei, Yu-Chi Wang, Shih-Ping Liu, Ton-Ru Shih, Hsin-Lien Lin, Yue-Mi Chen, Jiun-Huei Sung et al. "Decellularization and recellularization technologies in tissue engineering." Cell transplantation 23, no. 4-5 (2014): 621-630; Song, Jeremy J., and Harald C. Ott. "Organ engineering based on decellularized matrix scaffolds." Trends in molecular medicine 17, no. 8 (2011): 424-432.

SUMMARY OF THE INVENTION

The present technology focuses on generating functional human islets or islet organoids that can be used as a model to study human pancreogenesis and for use in organ-on-chips for drug screening and diabetes pathophysiological studies [Bhatia S N, Ingber D E. Microfluidic organs-on-chips. *Nat Biotechnol* 32, 760-772 (2014)]. The human induced pluripotent stem cell (iPSC)-derived islet organoids can also be used for patient-specific islet transplantation, offering renewable sources of islet-replacement tissues.

In spite of intense efforts made to produce pancreatic β-cells from human pluripotent stem cell (hPSC) differentiation over the past decade, niches inducing in vitro self-assembly of islet organoids from hPSCs have yet to be identified. A gel solution made by decellularized pancreatic extracellular matrix (dpECM) has been found to significantly promote islet organogenesis and morphogenesis during hPSC endocrine development. Compared to Matrigel-coated substrates, hPSCs differentiated on dpECM coated substrates formed much more aggregates even under 2D cultures. At the end of stepwise differentiation, hPSCs-derived cells exhibit similar cellular composition and architecture to native pancreatic islets. The formation of microvasculatures within assembled islets was also demonstrated. Cells differentiated in the presence of dpECM secrete more insulin in response to glucose level. Remarkably, dpECM facilitates generating more C-peptide+/glucagon− cells rather than C-peptide+/glucagon+ cells. These findings provide the evidence of a tissue instructive role of dpECM in recapitulating functional pancreatic islets during induced hPSC pancreatic development. This work is reported in Bi H, Ye K and Jin S (2016). Engineering tissue substrates for generation of islet-like organoids from human pluripotent stem cell differentiation. Front. Bioeng. Biotechnol. Conference Abstract: 10th World Biomaterials Congress. doi: 10.3389/conf.FBIOE.2016.01.02293.

To generate these islet organoids, a new differentiation protocol was developed by exposing cells to decellularized rat pancreatic extracellular matrix (dpECM) on Matrigel (MG) coated substrates. For the first time, we demonstrated that hPSCs differentiated on dpECM/MG substrates were self-assembled into islet organoids consisting of all four endocrine cell types of islets, i.e. α, β, δ, and PP cells. These organoids expressed higher levels of islet marker genes and are capable of physiological secreting insulin in response to glucose challenge. These findings provide the first evidence of a tissue instructive role of pancreatic ECM in recapitulating functional pancreatic islet in vitro, albeit ECM collected from a mouse β-cell monolayer culture has been found to promote ESC pancreatic differentiation [Narayanan, Karthikeyan, Vivian Y. Lim, Jiayi Shen, Zhen Wei Tan, Divya Rajendran, Shyh-Chyang Luo, Shujun Gao, Andrew C A Wan, and Jackie Y. Ying. "Extracellular matrix-mediated differentiation of human embryonic stem cells: differentiation to insulin-secreting beta cells." Tissue Engineering Part A 20, no. 1-2 (2013): 424-433].

Matrigel® (Corning) is the trade name for a gelatinous protein mixture secreted by Engelbreth-Holm-Swarm (EHS) mouse sarcoma cells produced and marketed by Corning Life Sciences and BD Biosciences. Trevigen, Inc. markets their own version under the trade name Cultrex® BME. Matrigel resembles the complex extracellular environment found in many tissues and is used by cell biologists as a substrate (basement membrane matrix) for culturing cells. Cells cultured on Matrigel demonstrate complex cellular behavior that is otherwise difficult to observe under laboratory conditions. For example, endothelial cells create intricate spiderweb-like networks on Matrigel coated surfaces but not on plastic surfaces. Such networks are highly suggestive of the microvascular capillary systems that suffuse living tissues with blood. Hence, Matrigel allows them to observe the process by which endothelial cells construct such networks that are of great research interest. The ability of Matrigel to stimulate complex cell behavior is a consequence of its heterogeneous composition. The chief components of Matrigel are structural proteins such as laminin, entactin, collagen and heparan sulfate proteoglycans which present cultured cells with the adhesive peptide sequences that they would encounter in their natural environment. Also present are growth factors like TGF-beta and EGF that prevent differentiation and promote proliferation of many cell types. Matrigel contains other proteins in small amounts and its exact composition can vary from lot to lot. Matrigel is also used as an attachment substrate in embryonic stem cell culture. When embryonic stem cells are grown in the absence of feeder cells, extracellular matrix components are needed to maintain the pluripotent, undifferentiated state (self-renewal). One of these matrices that can be used is diluted Matrigel. When used undiluted, Matrigel promotes stem cell growth and differentiation. See, Hughes, C. S., Postovit, L. M., Lajoie, G. A. (2010). "Matrigel: a complex protein mixture required for optimal growth of cell culture". Proteomics. 10 (9): 1886-90. doi:10.1002/pmic.200900758. PMID 20162561, Benton, G., George, J., Kleinman, H. K., Arnaoutova, I. (2009). "Advancing science and technology via 3D culture on basement membrane matrix". Journal of cellular physiology. 221 (1): 18-25. doi:10.1002/jcp.21832. PMID 19492404, Arnaoutova, I., George, J., Kleinman, H. K., and Benton, G. (2009). "The endothelial cell tube formation assay on basement membrane turns 20". Angiogenesis. 12 (3): 267-74. doi:10.1007/s10456-009-9146-4. PMID 19399631, Benton, G., Kleinman, H. K., George, J., Arnaoutova, I. (2011). "Multiple uses of basement membrane-like matrix (BME/Matrigel) in vitro and in vivo with tumor cells". International Journal of Cancer. Journal International Du Cancer. 128 (8): 1751-7. doi:10.1002/ijc.25781. PMID 21344372, Xu, C., Inokuma, M. S., Denham, J., Golds, K., Kundu, P., Gold, J. D., Carpenter, M. K. (2001).

"Feeder-free growth of undifferentiated human embryonic stem cells". Nature Biotechnology. 19 (10): 971-4. doi: 10.1038/nbt1001-971. PMID 11581665.

A decellularized ECM (dECM) preparation procedure according to the present technology distinguishes a large body of work utilizing detergents and denaturing conditions to produce the decellularized extracellular matrix samples. The present technology uses a detergent-free decellularization protocol. Specifically, the dECM samples are prepared using cycles of detergent-free hypotonic/hypertonic washes to decellularize the tissue via an osmotic stress.

Generally, established procedures use intact decellularized extracellular matrix that has maintained its 3D architecture, and potentially the vasculature of the original tissue, as a scaffold to seed stem cells, thereby recellularizing the tissue. In contrast, one embodiment of the present approach lyophilizes the decellularized extracellular matrix and uses it as a powder that is combined with Matrigel to form the scaffold for the stem cells. Subsequently, the dECM component is used as a source of regulatory signals for differentiation, rather than directly as a scaffold for the stem cells.

It is noted that the present technology may be applied to other organs, as the organ specific matrix is the differentiating factor, and therefore different matrices will result in different tissue types. For example, other cell types/tissues/organs that may be produced are:

Exocrine secretory epithelial cells: Salivary gland mucous cell (polysaccharide-rich secretion); Salivary gland number 1 (glycoprotein enzyme-rich secretion); Von Ebner's gland cell in tongue (washes taste buds); Mammary gland cell (milk secretion); Lacrimal gland cell (tear secretion); Ceruminous gland cell in ear (earwax secretion); Eccrine sweat glandering dark cell (glycoprotein secretion); Eccrine sweat gland clear cell (small molecule secretion); Apocrine sweat gland cell (odoriferous secretion, sex-hormone sensitive); Gland of Moll cell in eyelid (specialized sweat gland); Sebaceous gland cell (lipid-rich sebum secretion); Bowman's gland cell in nose (washes olfactory epithelium); Brunner's gland cell in duodenum (enzymes and alkaline mucus); Seminal vesicle cell (secretes seminal fluid components, including fructose for swimming sperm); Prostate gland cell (secretes seminal fluid components); Bulbourethral gland cell (mucus secretion); Bartholin's gland cell (vaginal lubricant secretion); Gland of Littre cell (mucus secretion); Uterus endometrium cell (carbohydrate secretion); Insolated goblet cell of respiratory and digestive tracts (mucus secretion); Stomach lining mucous cell (mucus secretion); Gastric gland zymogenic cell (pepsinogen secretion); Gastric gland oxyntic cell (hydrochloric acid secretion); Pancreatic acinar cell (bicarbonate and digestive enzyme secretion; Paneth cell of small intestine (lysozyme secretion); Type II pneumocyte of lung (surfactant secretion); Club cell of lung; Hormone-secreting cells; Anterior pituitary cells; Somatotropes; Lactotropes; Thyrotropes; Gonadotropes; Corticotropes; Intermediate pituitary cell, secreting melanocyte-stimulating hormone; Magnocellular neurosecretory cells; nonsecreting oxytocin; secreting vasopressin; Gut and respiratory tract cells; secreting serotonin; secreting endorphin; secreting somatostatin; secreting gastrin; secreting secretin; nonsecreting cholecystokinin; secreting insulin; secreting glucagon; nonsecreting bombesin; Thyroid gland cells; Thyroid epithelial cell; Parafollicular cell; Parathyroid gland cells; Parathyroid chief cell; Oxyphil cell; Adrenal gland cells; Chromaffin cells; secreting steroid hormones (mineralocorticoids and gluco corticoids); Leydig cell of testes secreting testosterone; Theca interna cell of ovarian follicle secreting estrogen; Corpus *luteum* cell of ruptured ovarian follicle secreting progesterone; Granulosa lutein cells; Theca lutein cells; Juxtaglomerular cell (renin secretion); Macula *densa* cell of kidney; Peripolar cell of kidney; Mesangial cell of kidney; Pancreatic islets (islets of Langerhans); Alpha cells (secreting glucagon); Beta cells (secreting insulin and amylin); Delta cells (secreting somatostatin); PP cells (gamma cells) (secreting pancreatic polypeptide); Epsilon cells (secreting ghrelin); Derived primarily from ectoderm; Integumentary system; Keratinizing epithelial cells; Epidermal keratinocyte (differentiating epidermal cell); Epidermal basal cell (stem cell); Keratinocyte of fingernails and toenails; Nail bed basal cell (stem cell); Medullary hair shaft cell; Cortical hair shaft cell; Cuticular hair shaft cell; Cuticular hair root sheath cell; Hair root sheath cell of Huxley's layer; Hair root sheath cell of Henle's layer; External hair root sheath cell; Hair matrix cell (stem cell); Wet stratified barrier epithelial cells; Surface epithelial cell of stratified squamous epithelium of cornea, tongue, oral cavity, esophagus, anal canal, distal urethra and vagina; basal cell (stem cell) of epithelia of cornea, tongue, oral cavity, esophagus, anal canal, distal urethra and vagina; Urinary epithelium cell (lining urinary bladder and urinary ducts); Nervous system; There are nerve cells, also known as neurons, present in the human body. They are branched out. These cells make up nervous tissue. A neuron consists of a cell body with a nucleus and cytoplasm, from which long thin hair-like parts arise; Sensory transducer cells; Auditory inner hair cell of organ of *Corti*; Auditory outer hair cell of organ of *Corti*; Basal cell of olfactory epithelium (stem cell for olfactory neurons); Cold-sensitive primary sensory neurons; Heat-sensitive primary sensory neurons; Merkel cell of epidermis (touch sensor); Olfactory receptor neuron; Pain-sensitive primary sensory neurons (various types); Photoreceptor cells of retina in eye; Photoreceptor rod cells; Photoreceptor blue-sensitive cone cell of eye; Photoreceptor green-sensitive cone cell of eye; Photoreceptor red-sensitive cone cell of eye; Proprioceptive primary sensory neurons (various types); Touch-sensitive primary sensory neurons (various types); Type I carotid body cell (blood pH sensor); Type II carotid body cell (blood pH sensor); Type I hair cell of vestibular system of ear (acceleration and gravity); Type II hair cell of vestibular system of ear (acceleration and gravity); Type I taste bud cell; Autonomic neuron cells; Cholinergic neural cell (various types); Adrenergic neural cell (various types); Peptidergic neural cell (various types); Sense organ and peripheral neuron supporting cells; Inner pillar cell of organ of *Corti*; Outer pillar cell of organ of *Corti*; Inner phalangeal cell of organ of *Corti*; Outer phalangeal cell of organ of *Corti*; Border cell of organ of *Corti*; Hensen cell of organ of *Corti*; Vestibular apparatus supporting cell; Taste bud supporting cell; Olfactory epithelium supporting cell; Schwann cell; Satellite glial cell (encapsulating peripheral nerve cell bodies); Enteric glial cell; Central nervous system neurons and glial cells; Neuron cells (large variety of types, still poorly classified); Interneurons; Basket cells; Stellate cells; Golgi cells; Granule cells; Lugaro cells; Unipolar brush cells; Martinotti cells; Chandelier cells; Medium spiny neurons; Cajal-Retzius cells; Double-bouquet cells; Neurogliaform cells; Spinal interneuron; Renshaw cells; Principal cells; Spindle neuron; Pyramidal cells; Place cells; Grid cells; Speed cells; Head direction cells; Betz cells; Stellate cells; Boundary cells; Astrocyte (various types); Oligodendrocyte; Ependymal cells; Tanycytes; Lens cells; Anterior lens epithelial cell; Crystallin-containing lens fiber cell; Derived primarily from mesoderm; Metabolism and storage cells; Adipocytes; White fat cell; Brown fat cell; Liver lipocyte; Barrier function cells (lung, gut, exocrine glands and urogenital tract); Kidney; Kidney parietal cell; Kidney glomerulus podocyte; Kidney proximal tubule brush border cell; Loop of Henle thin segment cell; Kidney distal tubule cell; Kidney collecting duct cell; Principal cells; Intercalated cells; Other; Type I pneumocyte (lining air space of lung cell); Pancreatic duct cell (centroacinar cell); Nonstriated duct cell (of sweat gland, salivary gland, mammary gland, etc.); Principal cell; Intercalated cell; Duct cell (of seminal vesicle, prostate gland, etc.); Intestinal brush border cell (with microvilli); Exocrine gland striated duct cell; Gall bladder epithelial cell; Ductulus efferens nonciliated cell; Epididymal principal cell; Epididymal basal cell; Endothelial cells; Extracellular matrix cells; Ameloblast epithelial cell (tooth enamel secretion); Planum semilunatum epithelial cell of vestibular system of ear (proteoglycan secretion); Organ of *Corti* interdental epithelial cell (secreting tectorial membrane covering hair cells); Loose connective tissue fibroblasts; Corneal fibroblasts (corneal keratocytes); Tendon fibroblasts; Bone marrow reticular tissue fibroblasts; Other nonepithelial fibroblasts; Pericyte; Nucleus pulposus cell of intervertebral disc; Cementoblast/cementocyte (tooth root bonelike ewan cell secretion); Odontoblast/odontocyte (tooth dentin secretion); Hyaline cartilage chondrocyte; Fibrocartilage chondrocyte; Elastic cartilage chondrocyte; Osteoblast/osteocyte; Osteoprogenitor cell (stem cell of osteoblasts); Hyalocyte of vitreous body of eye; Stellate cell of perilymphatic space of ear; Hepatic stellate cell (Ito cell); Pancreatic stelle cell; Contractile cells; Skeletal muscle cell; Red skeletal muscle cell (slow); White skeletal muscle cell (fast); Intermediate skeletal muscle cell; Nuclear bag cell of muscle spindle; Nuclear chain cell of muscle spindle; Satellite cell (stem cell); Heart muscle cells; Ordinary heart muscle cell; Nodal heart muscle cell; Purkinje fiber cell; Smooth muscle cell (various types); Myoepithelial cell of iris; Myoepithelial cell of exocrine glands; Blood and immune system cells; Erythrocyte (red blood cell); Megakaryocyte (platelet precursor); Monocyte (white blood cell); Connective tissue macrophage (various types); Epidermal Langerhans cell; Osteoclast (in bone); Dendritic cell (in lymphoid tissues); Microglial cell (in central nervous system); Neutrophil granulocyte; Eosinophil granulocyte; Basophil granulocyte; Hybridoma cell; Mast cell; Helper T cell; Suppressor T cell; Cytotoxic T cell; Natural killer T cell; B cell; Natural killer cell; Reticulocyte; Stem cells and committed progenitors for the blood and immune system (various types); Germ cells; Oogonium/Oocyte; Spermatid; Spermatocyte; Spermatogonium cell (stem cell for spermatocyte); Spermatozoon; Nurse cell; Ovarian follicle cell; Sertoli cell (in testis); Thymus epithelial cell; Interstitial cells; Interstitial kidney cells; Musculoskeletal system; Musculoskeletal system; Human skeleton; Joints; Ligaments; Muscular system; Tendons; Digestive system; Main article: Digestive system; Mouth; Teeth; Tongue; Salivary glands; Parotid glands; Submandibular glands; Sublingual glands; Pharynx; Oesophagus; Stomach; Small intestine; Duodenum; Jejunum; Ileum; Large intestine; Liver; Gallbladder; Mesentery; Pancreas; Respiratory system; Main article: Respiratory system; Nasal cavity; Pharynx; Larynx; Trachea; Bronchi; Lungs; Diaphragm; Urinary system; Main article: Urinary system; Kidneys; Ureters; Bladder; Urethra; Reproductive organs; Female reproductive system; Main article: Female reproductive system; Internal reproductive organs; Ovaries; Fallopian tubes; Uterus; Vagina; External reproductive organs; Vulva; Clitoris; Placenta; Male reproductive system; Main article: Male reproductive system; Internal reproductive organs; Testes; Epididymis; Vas deferens; Seminal vesicles; Prostate; Bulbourethral glands; External reproductive organs; Penis; Scrotum; Endocrine glands; Main article: Endocrine system; Pituitary gland; Pineal gland; Thyroid gland; Parathyroid glands; Adrenal glands; Pancreas; Cardiovascular system; Main article: Cardiovascular system; See also: List of arteries of the human body and List of veins of the human body; The heart; Arteries; Veins; Capillaries; Lymphatic system; Main article: Lymphatic system; Lymphatic vessel; Lymph node; Bone marrow; Thymus; Spleen; Gut-associated lymphoid tissue; Tonsils; Nervous system; The brain; Cerebrum; Cerebral hemispheres; Diencephalon; The brainstem; Midbrain; Pons; Medulla oblongata; Cerebellum; The spinal cord; The ventricular system; Choroid plexus; Peripheral nervous system; Nerves; Cranial nerves; Spinal nerves; Ganglia; Enteric nervous system; Sensory organs; Main article: Sensory system; Eye; Cornea; Iris; Ciliary body; Lens; Retina; Ear; Outer ear; Earlobe; Eardrum; Middle ear; Ossicles; Inner ear; Cochlea; Vestibule of the ear; Semicircular canals; Olfactory epithelium; Tongue; Taste buds; Integumentary system; Main article: Integumentary system; Mammary glands; Skin; Subcutaneous tissue;

Islet organogenesis is shown to occur if hPSCs receive signals from tissue-specific matrices, such as dpECM. The cellular aggregates formed during hPSC differentiation possess cellular composition and tissue architecture similar to native pancreatic islets. Experimental data illustrated the organoids have a comparative ratio to that of human islet, in which 50-70% of the cells are β-cells, 20-30% are α-cells, ≈10% are δ cells, and <5% are pancreatic polypeptide (PP) cells.

Applications of the islet organogenesis in vitro through stem cell differentiation allow improved understanding of β-cell maturation and islet organogenesis and morphogenesis during hPSC pancreatic differentiation. It also helps provide a better system for generating mature islet organoids for islet transplantation and/or for use in drug screening and pathological studies, leading to a cure to diabetes.

dpECM contains essential factors that provide unique tissue niches necessary for formation of islet organoids from hPSC differentiation. ECM gel was derived from animal pancreas using a new process. dpECM gel provides unique substrates to facilitate hPSC differentiation into pancreatic lineages and then assembling into tissue structures using a stepwise differentiation protocol. This finding offers a new strategy to improve the current in vitro organ development procedures for producing functional islets for diabetes treatment.

Rat pancreas were cut into 3 mm thick slices, and treated repeatedly with deionized water and sodium chloride-ammonia hydroxide solution for four days. After rinse and lyophilization, total DNA content of dpECM was examined. dpECM was milled and reconstituted by pepsin-containing acetic acid and neutralized. One hour before seeding human induced pluripotent stem cells (iPSCs), six-well plates were coated with matrigel (MG) and varied concentrations of dpECM. MG coated plates serve as a control for comparison. To develop iPSCs into islet organoids, a novel stepwise organ development protocol was used. Expression of pancreatic marker genes and proteins were examined by quantitative real-time PCR and flow cytometric analyses at the end of each stage of islet development.

Porcine pancreas may also be used as the source of the dpECM. Presumably, human pancreas may be used. The human pancreas may be from a cadaver, a donor, or from autologous tissue. Matrigel and biomaterials may be mixed with collagen during scaffolding, to improve matrix strength and physiological cues.

Full islet organoids (consisting of four subtypes of pancreatic endocrine cells) from human embryonic stem cells (hESCs) were grown within a biomimetic scaffold, which had an architecture typical of human adult islets, comprising α, β, δ, and PP cells. Both β cells and non-β cells were mixed to form organoids that secrete insulin and C-peptide in response to glucose challenges.

The mechanical strength of collagen scaffolds may be also enhanced by treating or mixing collagen with other chemicals, such as polyethylene (glycol) diacrylate (PEGDA). Typically, this process is performed after the ESC are added to the matrix, so the treatment is preferably compatible with continued growth and maturation of the cells. According to one embodiment, the treatment is provided to increase the stiffness of the collagen matrix to be in the same range as human pancreas, though the target may be higher or lower. Further, the treatment is not limited to a single application, and therefore may be provided to alter the stiffness over time.

Because the treatment with PEGDA is light-activated, this opens the possibility of photolithographic patterning, at least in two dimensions, but also in three dimensions using crossed optical beams and dual-photon absorption techniques. This, for example, may be used to provide textures for the tissue, weak channels for vascularization or duct formation, and the like. Further, an optically-activated linker may be used to spatially link proteins and other factors to the matrix while the cells are maturing, to guide positional and three dimensional development of the neoorgan. It is noted that mechanical/physical patterning of the developing neoorgan is also possible, as is local injection of factors. Further, optical, mechanical, and other physical processes may be used to induce localized cell death or apoptosis, which may also assist the neoorgan in developing an adult-type physiology.

The dpECM procedure enables the removal of approximately 99% of DNA from animal pancreas. At the end of stage I of differentiation, the expression of definitive endoderm marker genes SOX17 and FOXA2 were increased 3.8 and 2 folds, respectively, when the cells were cultured on dpECM plus MG coated surfaces compared to cells cultured on MG-coated surfaces. At stage II of differentiation, the expression of pancreatic progenitor markers ISL-1 and PDX1 mRNA increased 2.5 folds in cells cultured on dpECM and MG coated surfaces. At stage III of differentiation, the pancreatic endoderm markers Nkx6.1 and PDX1 mRNA increased 4.7 and 3 folds in cells cultured on dpECM and MG coated surfaces. Notably, the expression of insulin increased 9 folds in cells cultured on dpECM and MG coated surfaces. Importantly, the gene expression levels of PDX1, Nkx6.1, glucagon, and insulin from iPSC-derived cells are comparable to those in human pancreas. The experimental results indicate that dpECM facilities the differentiation of hPSCs into functional islet organoids. Experimental data obtained from flow cytometry confirmed that more than 60 percent of cells expressed insulin at the end of differentiation using dpECM as additional substrates.

dpECM gel offers an excellent tissue niche for hPSC islet differentiation, providing an understanding on the role of pancreatic tissue-derived dECM in hPSC differentiation.

There are a number of protocols developed in the last two decades for preparing decellularized ECMs from both human and animal tissue samples. Most of these protocols require the use of detergents that are harsh to the preservation of valuable growth factors and tissue niches in decellularized ECMs [Vorotnikova E, et al. Extracellular matrix-derived products modulate endothelial and progenitor cell migration and proliferation in vitro and stimulate regenerative healing in vivo. *Matrix Biol* 29, 690-700 (2010); Faulk D M, et al. The effect of detergents on the basement membrane complex of a biologic scaffold material. *Acta Biomater* 10, 183-193 (2014); Kasimir M T, et al. Comparison of different decellularization procedures of porcine heart valves. *Int J Artif Organs* 26, 421-427 (2003); Poornejad N, et al. Efficient decellularization of whole porcine kidneys improves reseeded cell behavior. *Biomed Mater* 11, 025003 (2016); Poornejad N, et al. The impact of decellularization agents on renal tissue extracellular matrix. *J Biomater Appl* 31, 521-533 (2016).] A detergent-free decellularization protocol is provided.

The ECM prepared using this protocol preserve growth factors and tissue niches that are essential to islet development from hPSCs. To prepare rat dpECMs, rat pancreata were treated with hyper/hypotonic solutions designed to completely remove cells from pancreatic tissues. Pancreatic tissue samples turned white and translucent after washing with hyper/hypotonic solutions. Total DNAs were extracted and examined to assess efficiency of the decellularization. Residual cellular DNA was not detected by electrophoresis in these dpECMs (FIG. 1A).

The biocompatibility of the dpECMs was characterized through a live/dead cell assay. As shown in FIGS. 1C and 1D, cells seeded on dpECM-coated substrates revealed a cell viability similar to those grown on the MG-coated substrates, albeit cells were less attached to dpECM coated substrates (FIG. 1C). Mixing dpECM with MG improved cell attachment (FIG. 1D). Further increase of dpECM in MG appeared to suppress cell attachment within 24 hours after seeding. Nevertheless, cells were able to reach 100% confluence after culturing several days (data not shown). These experimental results suggested that dpECMs support cell growth. The mixing of dpECM with MG seems to improve cell attachment during seeding.

During experiments, it was discovered that dpECM promotes remarkably the formation of cell clusters during iPSC pancreatic differentiation in 2D cultures. The growth factors and tissue niches preserved in dpECM during decellularization appear to offer tissue-inspired niches for pancreatic endocrine development. These effects were systematically characterized, to investigate whether cell clusters formed in the presence of dpECM are actually islet organoids that are physiologically functional.

To determine the instructive effect of dpECM on hPSC pancreatic differentiation, iPSCs were differentiated on MG/dpECM coated dishes using a four stage differentiation protocol as shown in FIG. 2A, i.e. differentiating cells stepwise toward definitive endoderm (DE) (S1), posterior foregut (S2), pancreatic progenitor (S3), and hormone-expressing endocrine cells (S4).

Further investigation measured whether increase in the amount of MG coated on culture plates has a similar effect on iPSC pancreatic differentiation. As shown in FIG. 10, the expression of SOX17 and FOXA2, two DE marker genes, were at almost the same level in cells differentiated on MG or 2×MG (doubling the amount of MG used for coating) coated plates. It is clear that the increase in coating matrix does not contribute to the enhancement of iPSC pancreatic lineage specification. The preferential factors entailed in dpECM promoted the iPSC pancreatic differentiation.

The organoids formed on dpECM coated condition have large variance in size. To determine whether cell clusters formed from iPSCs in the presence of dpECM are islets or islet organoids, cell compositions and architectures of cells collected were characterized at end of S4. The expression of pancreatic endocrine hormones such as c-peptide (C-PEP, a peptide released from the pancreatic β-cells during cleavage of insulin from proinsulin), glucagon (GCG), somatostatin (SST), and pancreatic polypeptide (PPY) in cell clusters were detected using immunostaining. Some insulin-secreting cells co-expressed glucagon, suggesting their low maturity. In contrast, the percentage of C-PEP and GCG polyhormonal cells was reduced in cell clusters formed on MG/dpECM coated plates. Together, these results suggest using dpECM as a culture substrate can improve islet organogenesis and maturation during in vitro differentiation of hPSCs.

To further characterize the iPSCs-derived organoids under MG/dpECM substrates, co-expression of insulin (INS) and NKX6.1 was detected in cells collected at the end of S4 by flow cytometric analysis. These experimental results supported the hypothesis that dpECM encourages self-assembly of cell clusters that are similar to pancreatic endocrine islets. To determine whether these cell clusters are capable of secreting insulin in response to glucose stimulation, glucose-stimulated insulin secretion (GSIS) analysis was carried out, which showed that either with or without the presence of dpECM, the S4 cells did not show glucose-responsive insulin secretion. However, the intracellular insulin could be purged out when depolarized by KCl solution, suggesting these cells had acquired exocytosis capability.

Clearly, these islet organoids developed from iPSCs on MG/dpECM coated substrates were immature. The detection of significant number of multi-hormone expressing endocrine cells in these cell clusters suggested that their cell compositions and structure are very similar to fetal islets.

It becomes clearly lately that the maturation of pancreatic endocrine cells needs extra time after pancreatic endoderm specification [Pagliuca F W, et al. Generation of functional human pancreatic beta cells in vitro. Cell 159, 428-439 (2014); Vegas A J, et al. Long-term glycemic control using polymer-encapsulated human stem cell-derived beta cells in immune-competent mice. Nat Med 22, 306-311 (2016)]. To test whether the extended culture of cells generated at S4 in a pancreatic preferential medium help mature the cell clusters into islets, we designed a five-stage differentiation protocol as shown in FIG. 6A. Cells generated at S4 were divided into two groups. A group of cells were continuously cultured on plates, whereas another group of cells were transferred to an ultra-low culture plates for suspension culture. [Pagliuca F W, et al. Generation of functional human pancreatic beta cells in vitro. Cell 159, 428-439 (2014).] The differentiated cells were first examined by staining with DTZ, which selectively chelates zinc in the insulin-containing secretory granules existed in insulin-producing cells [Wang X, Ye K. Three-dimensional differentiation of embryonic stem cells into islet-like insulin-producing clusters. Tissue Eng Part A 15, 1941-1952 (2009)]. The result showed that cells in suspension culture appeared crimson red, while undifferentiated hPSCs were not stained (FIG. 6B), indicating the existence of insulin-producing cells in extended suspension culture.

Further investigation by GSIS assay demonstrated that the S5 cells under 2D culture did not show glucose-responsiveness in either MG or dpECM groups (FIG. 6C), although more organoids were formed from cells cultured on dpECM coating condition (FIG. S4), and more insulin were secreted from cells grown on dpECM groups (FIG. 6C). In sharp contrast, the amount of insulin secreted from cells grown on dpECM groups increased significantly responding to an increase in glucose concentration (FIG. 6D). As shown in FIG. 6D, aggregation condition at S4 and S5 permits insulin secretion correlated with glucose levels at all the substrate coating condition tested. Cells from MG group secreted insulin at low and high glucose concentrations were 0.77±0.34 µIU/µg DNA and 1.40±0.61 µIU/µg DNA, respectively. In addition, with the stimulus of KCl the depolarized cells released 1.81±0.46 µIU/µg DNA. A more remarkable difference was found in cells from two dpECM groups showing 2.02±0.71 (M+d 25%) and 2.90±0.64 (M+d 50%) fold more insulin secreted when respond from low to high glucose concentrations (FIG. 6D). Impressively, the overall amount of insulin released from dpECM-treated cells was ~2 folds more than that from MG control group, which further validated the previous finding that dpECM enhances insulin expression and maturation (FIG. 2E and FIG. 4C).

Having characterized the unique role of the dpECM played in human iPSC differentiation towards islet tissue development, the dpECM coating and differentiation procedures developed were then investigated to see if they are robust to other hPSC lines. Human ESC line H9 has been widely studied and reported by many research groups [Jin S, Yao H, Weber J L, Melkoumian Z K, Ye K. A synthetic, xeno-free peptide surface for expansion and directed differentiation of human induced pluripotent stem cells. PLoS One 7, e50880 (2012); Wen Y, Jin S. Production of neural stem cells from human pluripotent stem cells. J Biotechnol 188, 122-129 (2014); Jin S, Yao H, Krisanarungson P, Haukas A, Ye K. Porous membrane substrates offer better niches to enhance the Wnt signaling and promote human embryonic stem cell growth and differentiation. Tissue Eng Part A 18, 1419-1430 (2012).] See FIGS. 6F-6G. Thus, H9 cells were induced to differentiate toward endocrine tissue using the same protocol shown in FIG. 6A. ESC-derived cells at the end of five-stage differentiation also demonstrated glucose level responsive insulin secretion (FIG. 6E). Likewise, cells after exposed on dpECM-coated environment and differentiated in 3D condition at later stage of differentiation, are able to produce more insulin compared to MG-alone environment (FIG. 6E). Approximately 2-fold increase in insulin secretion can be detected when cells are stimulated by glucose. Moreover, the same cells after challenged with elevated KCl produced much higher insulin. These experimental results demonstrate that hPSC-derived endocrine in this work are able to not only secrete insulin in response to glucose but also are responsive to a depolarizing concentration of KCl.

As demonstrated by optical sections through the 3D cultured organoids, the core of the islets was almost exclusively composed of C-PEP$^+$ and GCG$^+$ cells were dispersed throughout the organoids. Flow cytometry revealed that 3D culture further increased C-PEP+ cells (FIG. 7A) with sharp decline of the GCG$^+$ population (FIG. 7B) as compared to S4 cells (FIGS. 4H and 4I). dpECM promotes the differentiation and maturation of islet tissue development from both iPSCs and ESCs.

Decellularized pancreatic ECM can serve as a natural niche for hPSC-based pancreatic islet organogenesis and β-cell maturation. We discovered, for the first time, that dpECM niche triggers self-assembly of condensed cellular clusters during hPSC differentiation towards islet tissue even in a 2D culture environment. These cellular clusters are composed of endocrine cells with similar proportions as found in human islets [Cabrera O, Berman D M, Kenyon N S, Ricordi C, Berggren P O, Caicedo A. The unique cyto-architecture of human pancreatic islets has implications for islet cell function. Proc Natl Acad Sci USA 2006, 103(7): 2334-2339]. While the mechanism of action of the role of hPSC-dpECM interaction during the initiation of stem cell differentiation is unclear, we speculate that through cell-matrix binding stem cells receive signals that are delivered to the cellular nucleus, leading to an induction of intrinsic pathway towards islet organogenesis. As such, cells differentiated in the presence of dpECM possessed higher levels of endocrine lineage commitment and capacity of insulin production, even if cell-dpECM interaction was no longer available during later stage of differentiation (S4~S5) (FIGS. 6A-6B). This finding verified, for the first time, the ineluctable role of acellular ECM in recapitulation of pancreatic islets when initiating stem cell differentiation in vitro. We have also shown that early stages of dpECM treatment remarkably enhances GSIS in both iPSC- and ESC-derived endocrine cells by using the five-stage differentiation protocol.

When preparing decellularized ECM, alternating between hyper- and hypotonic solutions allow effective removal of cells from sliced pancreatic tissue by simple osmotic effect. Unlike detergent-based decellularization, the present approach has minimal impact on ECM structure, growth factor removal, and direct protein denature [Hunter J D, Cannon J A. Biomaterials: So Many Choices, So Little Time. What Are the Differences? *Clin Colon Rect Surg* 27, 134-139 (2014)]. The results indicated that dpECM contains less than 1% of the native DNA after decellularization (FIG. 1A), and no large DNA fragments was detected (FIG. 1B). These properties satisfy the criteria of an ideal nonimmunogenic acellular biomaterial: 1) contains less than 50 ng dsDNA per mg ECM dry weight; and 2) less than 200 bp DNA fragment length [Crapo P M, Gilbert T W, Badylak S F. An overview of tissue and whole organ decellularization processes. *Biomaterials* 32, 3233-3243 (2011)]. In addition to the effectiveness of removing cellular contents, the reagents used in this study are easily rinsed off when comparing to the efforts of flushing detergents from decellularized tissues, as small amount of residual detergent can cause apoptosis and inflammation. To assess the in vitro biocompatibility of dpECM, live-dead cell assay was conducted for the cells seeded on MG with or without dpECM coating. Although the dpECM was found not to be toxic to hPSCs, a remarkable decrease of attachment rate was observed (FIG. 8B). A possible explanation is that dpECM contains insufficient adhesion molecules required for undifferentiated hPSCs attachment, such as fibronectin, vitronectin and laminin [Goh S K, et al. Perfusion-decellularized pancreas as a natural 3D scaffold for pancreatic tissue and whole organ engineering. *Biomaterials* 34, 6760-6772 (2013); Hague M A, Nagaoka M, Hexig B, Akaike T. Artificial extracellular matrix for embryonic stem cell cultures: a new frontier of nanobiomaterials. *Science and technology of advanced materials* 11, 014106 (2010)]. However, the reduced attachment rate on dpECM-coat surface did not inhibit the proliferation of hPSCs and cells under all culturing conditions reached 100% confluence at S2 (data not shown).

Recent advancements of biomaterials for stem cell differentiation have highlighted the importance of cell-material communications in promoting differentiation of cells into specific lineages Pang H K, Kim B S. Modulation of stem cell differentiation with biomaterials. *International journal of stem cells* 3, 80-84 (2010)]. Matrigel is a prevailing ECM substrate used for hPSC culture systems, which is an extract from mouse sarcoma-derived basement membrane rich in laminin, collagen IV, and heparan sulfate proteoglycans [Kibbey M C. Maintenance of the EHS sarcoma and Matrigel preparation. *Journal of tissue culture methods* 16, 227-230 (1994)]. Extensive evidences have been documented the supportive role of Matrigel in stem cell survival, attachment, proliferation, and differentiation [Hughes C S, Postovit L M, Lajoie G A. Matrigel: a complex protein mixture required for optimal growth of cell culture. *Proteomics* 10, 1886-1890 (2010)]. However, lack of tissue-specificity is one of the disadvantages of using Matrigel as matrix for pancreatic differentiation, since subtle differences in ECM composition from various types of tissue may significantly change cellular interactions in a lineage-specific manner [Lang R, et al. Three-dimensional culture of hepatocytes on porcine liver tissue-derived extracellular matrix. *Biomaterials* 32, 7042-7052 (2011)]. De Carlo et al. found pancreatic ECM is a favorable substrate for long term in vitro culture of rat islets. These islets cultured on pancreatic ECM showed higher survival rate and better GSIS capability when compared to cells cultured on liver ECM [De Carlo E, et al. Pancreatic acellular matrix supports islet survival and function in a synthetic tubular device: in vitro and in vivo studies. *International journal of molecular medicine* 25, 195-202 (2010)]. It has also been reported that dpECM promotes insulin expression in mouse β-cell line MIN-6 recently [Wu D, et al. 3D Culture of MIN-6 Cells on Decellularized Pancreatic Scaffold: In Vitro and In Vivo Study. *BioMed research international* 2015, 432645 (2015)]. These works parallel findings that dpECM increases the expression of critical transcription factors and marker genes in hPSCs endocrine commitment (FIGS. 2A-2E, which further escalates the yield of monoclonal β-like cells (FIGS. 4F-4J and 5A-5C). Therefore, it is reasonable to conclude that dpECM resembles the native microenvironmental niche, which represents spatially-restricted context that drives cell fate specification in early pancreas development.

In vitro generation of pancreatic organoids from pancreatic progenitors have recently been reported [Greggio C, et al. Artificial three-dimensional niches deconstruct pancreas development in vitro. *Development* 140, 4452-4462 (2013); Broutier L, et al. Culture and establishment of self-renewing human and mouse adult liver and pancreas 3D organoids and their genetic manipulation. *Nature protocols* 11, 1724-1743 (2016).] and vascularized organoids can be formed after transplanting iPSC-derived insulin-secreting cells under kidney capsule [Raikwar S P, Kim E M, Sivitz W I, Allamargot C, Thedens D R, Zavazava N. Human iPS cell-derived insulin producing cells form vascularized organoids under the kidney capsules of diabetic mice. *PLoS One* 10, e0116582 (2015)]. These organoids exhibited robust proliferation and formed regions containing exocrine and endocrine cells. Using the five-stage differentiation protocol, cells differentiated on dpECM-coated dishes showed a dose-dependent capacity of reassociating 3D clusters (FIG. 3A-3C and FIG. 11). In order to minimize the background from mono-layered cells, we used bright field, instead of phase contrast, images for aggregates analysis. Notably, the number and size of clusters increased from S2 to S3 over time, and a turnover was observed from in S4 and S5, probably because of increased cell death caused by including R428 into differentiation medium in S4 (data not shown). It has been reported that R428, an inhibitor of tyrosine kinase receptor AXL, promotes the maturation of stem cell-derived insulin-producing cells [Rezania A, et al. Reversal of diabetes with insulin-producing cells derived in vitro from human pluripotent stem cells. *Nat Biotechnol* 32, 1121-1133 (2014)]. To reduce the cytotoxic effect of R428, we modified its concentration into 0.5 μM, which is 4 times lower than the concentration used in previous study [Rezania A, et al. Reversal of diabetes with insulin-producing cells derived in vitro from human pluripotent stem cells. *Nat Biotechnol* 32, 1121-1133 (2014)]. Interestingly, these self-assembled clusters showed multiple types of endocrine cells with similar proportions to pancreatic islets. These are the first islet organoids formed by self-organizing stem cells with the existence of four major islet cell types, which harbors geometric constraints reciprocal cell-cell interactions. Such unique heterotypic contacts of mixed cell types in human islets play a central role in regulating β-cell function to achieve glucose homeostasis [Cabrera o, Berman D M, Kenyon N S, Ricordi C, Berggren P O, Caicedo A. The unique cytoarchitecture of human pancreatic islets has implications for islet cell function. *Proc Natl Acad Sci USA* 103, 2334-2339 (2006).]: insulin signals glucose uptake by peripheral tissues, whereas glucagon breakdown hepatic glycogen into circulation, somatostatin inhibits both insulin and glucagon secretions, and pancreatic polypeptide inhibits pancreatic exocrine and endocrine secretion [Jain R, Lammert E. Cell-cell interactions in the endocrine pancreas. *Diabetes, obesity & metabolism* 11 Suppl 4, 159-167 (2009)]. The present findings provide a potential model for further study of islet neogenesis and function, as well as a source of tissue for autologous transplants [Greggio C, De Franceschi F, Grapin-Botton A. Concise reviews: In vitro-produced pancreas organogenesis models in three dimensions: self-organization from few stem cells or progenitors. *Stem Cells* 33, 8-14 (2015)].

It should be pointed out that over the latest few years, efforts in controlling hPSCs differentiation into insulin-secreting β-cells have been made and remarkable success has been achieved [Chen S, et al. A small molecule that directs differentiation of human ESCs into the pancreatic lineage. *Nat Chem Biol* 5, 258-265 (2009); D'Amour K A, et al. Production of pancreatic hormone-expressing endocrine cells from human embryonic stem cells. *Nature biotechnology* 24, 1392-1401 (2006); Basford C L, et al. The functional and molecular characterisation of human embryonic stem cell-derived insulin-positive cells compared with adult pancreatic beta cells. *Diabetologia* 55, 358-371 (2012)]. However, these in vitro generated β-like cells behave more like fetal pancreatic cells, which display a high basal insulin secretion at low glucose concentrations [Hrvatin S, et al. Differentiated human stem cells resemble fetal, not adult, beta cells. *Proc Natl Acad Sci USA* 111, 3038-3043 (2014); Bruin J E, et al. Characterization of polyhormonal insulin-producing cells derived in vitro from human embryonic stem cells. *Stem cell research* 12, 194-208 (2014)]. Although certain amount of insulin was detected in 2D cultured cells, insulin secretion in response to glucose stimulation was not observed (FIG. 6C). Missing microenvironmental information may partially result in this immaturation of in vitro differentiated cells. 3D culture is considered a mimicry of the structural and topological organization of native pancreatic tissue [Takeuchi H, Nakatsuji N, Suemori H. Endodermal differentiation of human pluripotent stem cells to insulin-producing cells in 3D culture. *Sci Rep* 4, 4488 (2014)]. In order to achieve 3D culture, cells were dissociated after S3 and re-aggregated in suspension culture for the last two stages without further addition of dpECM. Interestingly, omission of dpECM in late stages did not nullify the enhanced insulin expression in cells cultured on dpECM for the first three stages of differentiation (FIGS. 6D and E), indicating cell-ECM communication during early stage of pancreatic specification from hPSCs is critical for enhancing yield of islet tissue [Russ H A, et al. Controlled induction of human pancreatic progenitors produces functional beta-like cells in vitro. *EMBO J* 34, 1759-1772 (2015)]. Compared with 2D culture, the insulin secretory function in cell aggregates was significantly improved, with more remarkable GSIS found in dpECM-treated cells (FIG. 6D). These results further emphasize the instructive role of dpECM in improving differentiation and maturation efficiency of hPSCs. Moreover, cells differentiated in aggregates secreted approximately 3 times more insulin than in monolayers (FIGS. 6C and D), which recapitulates previous finding that direct 3D contact is fundamental for the coordination of insulin secretion in β-cells [Brereton H C, et al. Homotypic cell contact enhances insulin but not glucagon secretion. *Biochem Bioph Res Co* 344, 995-1000 (2006)]. Importantly, although considerable variation in maturation efficiencies has been observed among different hPSC lines, a similar GSIS efficiency is achieved in both NIH-approved human iPSC and ESC line (FIG. 6E), indicating dpECM promotes the differentiation and maturation of various types of hPSCs. In addition, with effectively induction of monohormonal pancreatic cells, the architecture and cellularity of the organoids generated from dpECM-treated cells remained similar to those of human islets (FIGS. 8A-8B), suggesting dpECM-treatment contributes to the recapitulation and more importantly, late stage development and maturation of islets.

The present technology highlights the capability of dpECM for representing the complex microenvironmental signals that facilitate pancreatic-lineage decision of hPSCs. Utilizing dpECM as an in vitro cell culture substrate, we demonstrated an improved efficiency of differentiating hPSCs to islet organoids. dpECM plays an instructive role in cell fate specification in early islet development, which gives rise to islet organoids with multicellular composition. These findings provide a foundation for future investigations into essential outside-in signals for producing clinically relevant pancreatic tissues.

It is therefore an object to provide a synthetic pancreatic islet organoid, comprising: a pancreas tissue-specific matrix; a collagen support material; about 50-70% pancreatic beta cells; about 20-30% pancreatic alpha cells; about 10% pancreatic delta cells; and about <5% pancreatic polypeptide cells.

The pancreatic beta cells, pancreatic alpha cells, pancreatic delta cells, and pancreatic polypeptide cells may be derived from human pluripotent stem cells. The pancreas tissue specific matrix may be derived from a non-human animal. The pancreas tissue specific matrix may be processed substantially without detergent treatment for cellular removal. The pancreas tissue specific matrix may be processed for cellular removal by cycles of high and low osmotic tension. The pancreas tissue specific matrix may have less than about 1% of the DNA of the tissue from which it is derived.

Another object provides a method of creating a synthetic pancreatic islet, comprising: extracting pancreas tissue-specific matrix from a mammal; coating a growth surface with cell growth factors and the extracted pancreas tissue-specific matrix; culturing pluripotent stem cells on the surface; and inducing the cells to differentiate through at least four stages of differentiation on the surface. The cells may differentiate to produce at least two, at least three, or at least four distinct cell types.

The cell growth factors may comprise Matrigel®. The cell growth factors may comprise laminin, collagen IV, and heparan sulfate proteoglycans.

The cells may comprise pancreatic alpha cells; pancreatic beta cells; pancreatic delta cells; and pancreatic polypeptide cells. The cells comprise: about 50-70% pancreatic beta cells; about 20-30% pancreatic alpha cells; about 10% pancreatic delta cells; and about <5% pancreatic polypeptide cells. The pluripotent stem cells may be human pluripotent stem cells. The mammal may be non-human.

A further object provides a method of creating a synthetic organoid that is vascularized, comprising: extracting tissue-specific matrix from a mammalian organ; coating a growth surface with cell growth factors comprising collagen and mucopolysaccharides, and the extracted tissue-specific matrix; culturing stem cells on the surface; and inducing the cells to differentiate on the surface.

The mammalian organ may be a pancreas, the stems cells may be pluripotent stem cells, and said inducing may comprise inducing the pluripotent stem cells to differentiate through at least four stages of differentiation, further comprising producing insulin and somatostatin from the synthetic organoid.

The inducing of the cells to differentiate may comprise sequentially incubating the cells in: Media in Stage 1 (S1) RPMI 1640 (Corning), B27 (Gibco), 50 ng/ml activin A (PeproTech) and 0.5-1 mM sodium butyrate (NaB, Sigma-Aldrich); Media in Stage 2 (S2) of RPMI 1640, B27, 250 µM ascorbic acid (Vc, Sigma-Aldrich), 50 ng/ml keratinocyte growth factor (KGF, PeproTech), 50 ng/ml Noggin (Pepro-Tech), 1 µM retinoic acid (RA, Sigma-Aldrich), 300 nM (−)-indolactam V (ILV, AdipoGen), and 100 nM LDN193189 (LDN, Sigma-Aldrich); Media in Stage 3 (S3), DME/F12 (HyClone) containing B27, 1 µM RA, 200 nM LDN, 300 nM ILV, 1 µM 3,3',5-Triiodo-L-thyronine sodium salt (T3, Sigma-Aldrich), 10 µM ALK5 inhibitor II (ALKi, Enzo Life Sciences), 10 µg/ml heparin (HP, Sigma-Aldrich), and supplemented glucose to a final concentration of 20 mM; Media in Stage 4 (S4), RPMI 1640, B27, 1 µM T3, 10 µM ALKi, 1 mM N-acetyl cysteine (N-Cys, Sigma-Aldrich), 0.5 µM R428 (SelleckChem), 10 µM trolox (Enzo Life Sciences), 100 nM γ-secretase inhibitor XX (Millipore), 10 µM zinc sulfate (Sigma-Aldrich), 10 mM nicotinamide (Nic, Sigma-Aldrich), 10 µg/ml HP, and 20 mM glucose; and Media in Stage 5 (S5) CMRL supplement containing 10% fetal bovine serum (ATCC), 1 µM T3, 10 µM ALKi, 0.5 µM R428, and 10 mM Nic.

Another object provides a process for generating cells producing insulin in response to glucose, comprising: cultivation and differentiation of pluripotent stem cells on a surface having pancreas tissue specific extracellular matrix and cellular growth factors which together are effective for controlling a differentiation of the cells into at least pancreatic alpha cells, pancreatic beta cells, pancreatic delta cells, and pancreatic polypeptide cells Another object provides a cell isolated from an animal, producing at least one pancreatic hormone, the cell having been generated from a pluripotent stem cell, and differentiated through at least four stages of differentiation in contact with pancreas tissue specific extracellular matrix and cellular growth factors which together are effective for controlling a differentiation of a progenitor of the cell into at least pancreatic alpha cells, pancreatic beta cells, pancreatic delta cells, and pancreatic polypeptide cells.

The generated cells comprise pancreatic alpha cells, pancreatic beta cells, pancreatic delta cells, and pancreatic polypeptide cells.

The generated cells may be used for treating a pancreatic disease, a metabolic syndrome, or a metabolic disease. The generated cells may be used for treating diabetes, hyperglycemia, or impaired glucose tolerance.

The process may further comprise implanting the generated cells into a mammal or human. The process may further comprise testing at least one drug for a modulation of a response of the cells to glucose.

The process may further comprise harvesting polypeptides secreted by the generated cells from a supernatant.

The generated cells may be maintained within an extracorporeal circulation loop of a mammal. The generated cells may be maintained within an extracorporeal circulation loop of a human.

The cell may be autologous. The cell may be a mammalian or human cell. The cell may produce at least insulin in response to glucose. The cell may be provided within an artificial islet of Langerhans. The pluripotent stem cell may be from a mammal or human.

The cell may be provided in a pharmaceutical composition containing at least one pharmaceutical carrier substance.

A pharmaceutical composition is provided containing at least one cell as provided above, and a pharmaceutical carrier substance.

A medical transplant or medical device is provided comprising at least one cell as provided above.

An at least partially synthetic organism is provided, comprising a cell as provided above.

BRIEF DESCRIPTION OF THE DRAWINGS

FIG. 1A shows Gel electrophoresis of DNA isolated from two dpECM replicates. Equal amount of native rat pancreatic tissues was used as control (rPan). FIG. 1B shows DNA quantitation (mean±SD) of dpECM in comparison to native pancreatic tissues, n>3. Values were expressed as mean±SD. *, $p<0.05$. FIG. 1C shows live-and-dead cell staining of iPSCs cultured on MG or dpECM coated dishes for 24 h. Bars, 50 µm. FIG. 1D shows live/dead cell dual-staining of iPSCs cultured on either MG or dpECM coated dishes for 24 h after seeding. Scale bars, 200 µm.

FIGS. 2A-2E shows a schematic summary of the 4-stage, 21-day differentiation protocol and characterization of marker genes during the differentiation. FIG. 2A shows in vitro differentiation protocol of iPSCs to islet tissue. Basal media as well as key molecules used are shown for each stage of differentiation. FIGS. 2B-2E show the profile of marker gene expression of hPSC-derived cells during 51 to S4 of differentiation. Cells were 2D cultured on MG- or MG-/dpECM-coated substrates using indicated concentrations. Expression levels of mRNA were assessed for DE (FIG. 2B), posterior foregut (FIG. 2C), pancreatic progenitor (FIG. 2D), and β-cell markers (FIG. 2E). Gene expression was relative to that in cells grown on MG-coated dishes. Results were from three or more experiments and shown as mean±SD. *, $p<0.05$; , $p<0.01$; *, $p<0.001$, compared to MG group. Cells were 2D cultured on MG or MG/dpECM (M+d) coated plates as described in Methods. The MG-dpECM ratios (w:w) of prepared MG/dpECM mixtures were 4:1, 2:1, and 1:1, respectively.

FIGS. 3A-3C shows microscopic examination of self-assembly of islet-like organoids at the end of Stage 2, 3, and 4 of iPSC differentiation. FIG. 3A show micrographs of cell clusters formed on MG/dpECM coated plates. Black scale bars, 1,000 µm; white scale bars, 200 µm. FIG. 3B shows number of cell clusters formed on MG/dpECM coated plates. Tiled images covering an area of 0.53 cm2 were randomly selected and analyzed by ImageJ software. Data are shown as mean±SD (n=8). *, $p<0.05$; , $p<0.01$; *, $p<0.001$. FIG. 3C show diameters of cell clusters formed on MG/dpECM coated plates. Gray bars indicate average diameter of aggregates.

FIG. 4A shows representative immunofluorescent staining of S4 cells labeled for C-peptide (C-PEP, green) and glucagon (GCG; red). 4,6-diamidino-2-phenylindole (DAPI, blue) was used for counterstaining nuclei. Scale bars, 50 µm. FIG. 4B shows representative immunofluorescent staining of S4 cells labeled for somatostatin (SST, green), pancreatic polypeptide (PPY; red), and DAPI. Scale bars, 50 µm. (FIGS. 4C-4E) Representative flow cytometric results of S4 cells stained for C-PEP and GCG (FIG. 4C), SST (FIG. 4D), and PPY (FIG. 4E). Numbers in quadrants represent the percentage of total counted cells.

(FIG. 4G) somatostatin (SST, green) and pancreatic polypeptide (PPY; red). 4,6-diamidino-2-phenylindole (DAPI, blue) was used for counterstaining cell nuclei. Scale bars, 50 µm. (FIGS. 4H-4I) Representative flow cytometric analysis of C-PEP (FIG. 4H), GCG (FIG. 4I), SST (FIG. 4J), and PPY (FIG. 4K) expressing cells in S4 cells. SSC: side scatter. (FIG. 4L) Representative flow cytometric analysis of S4 cells dual-stained for C-PEP and GCG. Numbers in quadrants represent the percentage of total counted cells.

(FIG. 5A) Flow cytometric analysis of insulin (INS) and Nkx6.1 expression in S4 cells. Numbers in quadrants represent the percentage of total counted cells, illustrating the typical population of both NKX6.1+ and insulin+ cells generated at S4. (FIG. 5B and FIG. 5C) Representative immunofluorescent staining of S4 cells cultured on various conditions. (B) pancreatic and duodenal homeobox 1 (PDX-1, green) and C-peptide (C-PEP, red). (FIG. 5C) MAF bZIP transcription factor A (MAFA, green) and glucagon (GCG, red). 4,6-diamidino-2-phenylindole (DAPI, blue) was used for counterstaining nuclei. Bars, 50 µm.

(FIG. 6A) A five-stage differentiation strategy. After S3, cells were either continuously cultured on MG/dpECM substrates (2D cultures) or transferred into ultra-low attachment plates for suspension cultures (3D culture). (FIG. 6B) DTZ staining of cell clusters at S5. Undifferentiated iPSCs cultured in ultra-low attachment plates for 24 hrs served as a control. Scale bars, 200 µm. Glucose-stimulated insulin secretion (GSIS) analysis was performed by challenging cells differentiated in 2D (FIG. 6C) or 3D (FIG. 6D) conditions with 2 mM and 20 mM glucose for 30 min at each step. The insulin release in response to secretagogue such as 30 mM KCl was also measured. 2 mM glucose was used along with KCl when determining insulin release in response to a secretogogue. Insulin secretion was determined as µIU insulin per µg cellular DNA (n=4). (FIG. 6E) Insulin secretion from ESCs-derived cells at S5 of suspension culture (n=3). Data are shown as mean±SD. *, p<0.05; **, p<0.01.

(FIGS. 6F-H) insulin secretion of IMR90 S5 2D, IMR S5 Aggregates, and H9 SW5 2D, with respect to glucose concentration (2 mM, 20 mM, 30 mM KCl), on MG, M+d 4:1, and M+d 2:1. (FIG. 6I) insulin secretion of IMR90 S5 2D vs. 3D, with respect to glucose concentration (2 mM, 20 mM, 30 mM KCl) and condition (MG, M+d 4:1, and M+d 2:1).

(FIG. 7E) Representative flow cytometric analysis of S5 cells dual-stained for C-PEP and GCG. Numbers in quadrants represent the percentage of total counted cells.

FIG. 13A shows cryosectioned islet organoids stained with H&E. Black scale bars, 50 µm; white scale bars, 10 µm. White arrowheads indicate capillary-like structures. FIG. 13B shows capillary density in S5 organoids as analyzed by Image-Pro Plus (Version 6.0). *, p<0.05. FIGS. 13C and 13D show representative images of cryosectioned islet organoids stained by antibodies against (FIG. 13C) CD31, or (FIG. 13D) C-peptide (CP) and CD31. White arrowheads indicate direct contact between CD31+ cells and CP+ cells. FIG. 13E shows representative flow cytometric analysis of CD31 and NG2 expressing cells in S5 organoids. SSC: side scatter. Numbers in quadrants represent the percentage of total counted cells.

DETAILED DESCRIPTION OF THE PREFERRED EMBODIMENTS

Example 1

Figure 1A:
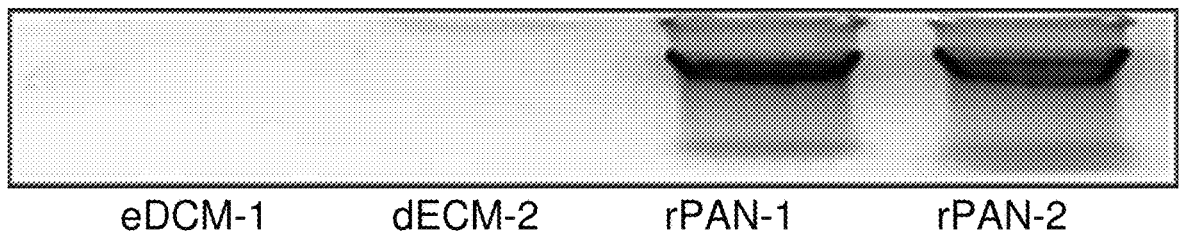
FIGS. 1A-1D shows dpECM preparation.

Rat pancreas were cut into 3 mm thick slices, and treated repeatedly with deionized water and sodium chloride-ammonia hydroxide solution for four days. After rinse and lyophilization, total DNA content of dpECM was examined. dpECM was milled and reconstituted by pepsin-containing acetic acid and neutralized. One hour before seeding human induced pluripotent stem cells (iPSCs), six-well plates were coated with matrigel (MG) and varied concentrations of dpECM. MG coated plates serve as a control for comparison. To differentiate iPSCs into islet organoids, a novel stepwise differentiation protocol developed was used. Expression of pancreatic marker genes and proteins were examined by quantitative real-time PCR and flow cytometric analyses at the end of each stage of differentiation.

The dpECM procedure developed in this study enables the removal of approximately 99% of DNA from animal pancreas. At the end of stage I of differentiation, the expression of definitive endoderm marker genes SOX17 and FOXA2 were increased 3.8 and 2 folds, respectively, when the cells were cultured on dpECM plus MG coated surfaces compared to cells cultured on MG-coated surfaces. At stage II of differentiation, the expression of pancreatic progenitor markers ISL-1 and PDX1 mRNA increased 2.5 folds in cells cultured on dpECM and MG coated surfaces. At stage III of differentiation, the pancreatic endoderm markers Nkx6.1 and PDX1 mRNA increased 4.7 and 3 folds in cells cultured on dpECM and MG coated surfaces. Notably, the expression of insulin increased 9 folds in cells cultured on dpECM and MG coated surfaces. Importantly, the gene expression levels of PDX1, Nkx6.1, glucagon, and insulin from iPSC-derived cells are comparable to those in human pancreas. The experimental results indicate that dpECM facilities the differentiation of hPSCs into functional islet organoids. Experimental data obtained from flow cytometry confirmed that more than 60 percent of cells expressed insulin at the end of differentiation using dpECM as additional substrates.

dpECM gel offers an excellent tissue niche for hPSC islet differentiation.

Materials and Methods

Preparation of Rat dpECM Gel

Rat pancreata were obtained from the Laboratory Animal Resources at the Binghamton University. Briefly, male and female Sprague Dawley rats (Charles River) were euthanized by CO2 asphyxiation according to the American Veterinary Medical Association (AVMA) guidelines. Pancreata were isolated and rinsed with cold PBS twice then stored at −80° C. until use. The frozen pancreata were cut into 1.5 mm sections using a deli-style slicer (Chef's choice 632, Edge Craft Corporation). The slices were rinsed with deionized water for 5 times on a tube rotator (Boekel Industries) at 4° C. with a speed of 20 rpm. Then the tissues were processed 4 cycles with hyper/hypotonic washes: gently shaken in hypertonic solution containing 100 g/l sodium chloride and 0.1% ammonium hydroxide at 4° C. for 12 hours. The materials were then transferred into deionized water and shaken at 4° C. for 12 hours. The resulting tissues were extensively rinsed with deionized water to remove any residue chemicals. The decellularized pancreatic tissues were lyophilized using Freezone freeze dry system (LABCONCO) and comminuted using a Wiley Mini Mill (Thomas Scientific). To solubilize the dpECM powder, 100 mg of lyophilized dpECM powder was digested by 10 mg of pepsin (Sigma) in 5 ml of 0.02 N acetic acid for 48 h at room temperature with continuous stirring. The resultant dpECM solution was aliquoted and stored at −80° C. until use.

Characterization of dpECM

Decellularization efficiency was evaluated by extracting DNA from lyophilized dpECM using a DNeasy Blood and Tissue Kit (QIAGEN) according to manufacturer's instructions. DNA content in dpECM was quantified using Synergy H1 Microplate Reader (BioTek) and also examined by 1% agarose gel electrophoresis.

Cytotoxicity of dpECM was examined using a viability/cytotoxicity kit (Life Technologies), according to manufacturer's instructions. Briefly, 24 h after seeding onto Matrigel-(Corning Life Science) or Matrigel- and dpECM-coated 6-well plate, the cultured iPSCs were rinsed twice with PBS and incubated with 2 μM Calcein A M and 2 μM ethidium homodimer reagents at 37° C. for 10 min. After rinsing again with PBS, the cell viability was evaluated using a Nikon fluorescence microscope.

Cell Culture

Undifferentiated iPSC line IMR90 and hESC line H9 (WiCell Research Institute) were maintained in mTeSR1 medium (Stemcell Technologies). Cells were passaged every 4 days at ratios of 1:3 to 1:5 as reported previously [Nair G, Hebrok M. Islet formation in mice and men: lessons for the generation of functional insulin-producing beta-cells from human pluripotent stem cells. *Curr Opin Genet Dev* 32, 171-180 (2015); Seymour P A, Sander M. Historical perspective: beginnings of the beta-cell: current perspectives in beta-cell development. *Diabetes* 60, 364-376 (2011)]. For induced differentiation into endocrine tissue, cells were dissociated by Accutase (Stemcell Technologies) and seeded onto 80 μg/ml of Matrigel (MG) or MG with various amount of dpECM-coated 6-well plate with a density of $1\times10^6$ cells/well and cultured in mTeSR1 medium. The dpECM concentrations used were: 20 μg/ml indicated as M+d 25%, 40 μg/ml (M+d 50%), or 80 μg/ml (M+d 100%). The ratios (w/w) of dpECM vs MG in the mixed ECM gel (M+d) were 1:4, 1:2, and 1:1. A five-stage differentiation protocol as dictated in (FIGS. 2A and 6A) was adopted to differentiate iPSCs and ESCs into islet organoids at 24 h post seeding. Twenty-four hours after seeding, cells were cultured in varied differentiation media following the timeframe shown in FIG. 2A.

Media in Stage 1 (S1) included RPMI 1640 (Corning), B27 (Gibco), 50 ng/ml activin A (PeproTech) and 1 mM sodium butyrate (NaB, Sigma-Aldrich) for the first 24 h. The NaB was reduced into 0.5 mM from day 2- to day 4 as described elsewhere [Seymour P A, Sander M. Historical perspective: beginnings of the beta-cell: current perspectives in beta-cell development. *Diabetes* 60, 364-376 (2011); Steiner D J, Kim A, Miller K, Hara M. Pancreatic islet plasticity: interspecies comparison of islet architecture and composition. *Islets* 2, 135-145 (2010)].

Media in Stage 2 (S2) consisted of RPMI 1640, B27, 250 μM ascorbic acid (Vc, Sigma-Aldrich), 50 ng/ml keratinocyte growth factor (KGF, PeproTech), 50 ng/ml Noggin (PeproTech), 1 μM retinoic acid (RA, Sigma-Aldrich), 300 nM (−)-indolactam V (ILV, AdipoGen), and 100 nM LDN193189 (LDN, Sigma-Aldrich).

Media in Stage 3 (S3), cells were cultured in DME/F12 (HyClone) containing B27, 1 μM RA, 200 nM LDN, 300 nM ILV, 1 μM 3,3',5-Triiodo-L-thyronine sodium salt (T3, Sigma-Aldrich), 10 μM ALK5 inhibitor II (ALKi, Enzo Life Sciences), 10 μg/ml heparin (HP, Sigma-Aldrich), and supplemented glucose to a final concentration of 20 mM.

Media in Stage 4 (S4), the differentiation media contained RPMI 1640, B27, 1 μM T3, 10 μM ALKi, 1 mM N-acetyl cysteine (N-Cys, Sigma-Aldrich), 0.5 μM R428 (SelleckChem), 10 μM trolox (Enzo Life Sciences), 100 nM γ-secretase inhibitor XX (Millipore), 10 μM zinc sulfate (Sigma-Aldrich), 10 mM nicotinamide (Nic, Sigma-Aldrich), 10 μg/ml HP, and 20 mM glucose. [Otonkoski, Timo, Gillian M. Beattie, Martin I. Mally, Camillo Ricordi, and Alberto Hayek. "Nicotinamide is a potent inducer of endocrine differentiation in cultured human fetal pancreatic cells." Journal of Clinical Investigation 92, no. 3 (1993): 1459.]

Figure 6A:
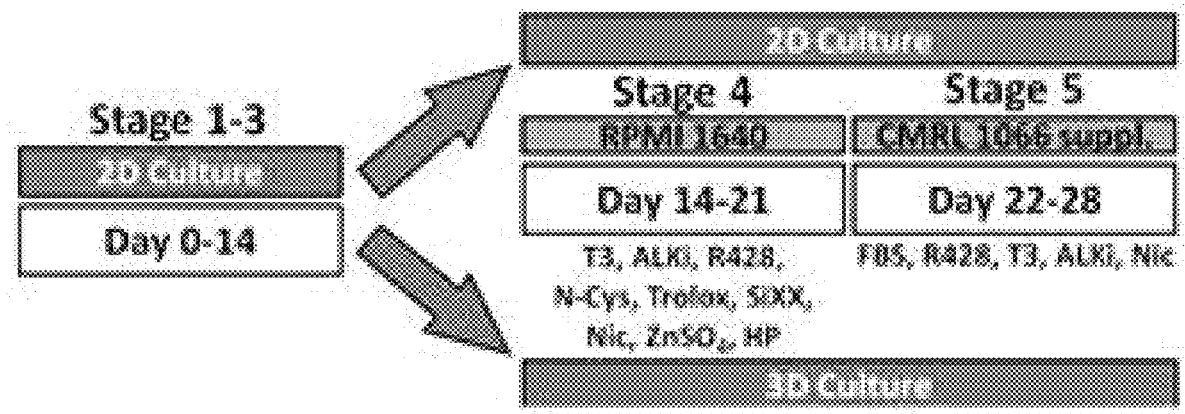
FIGS. 6A-6E show that dpECM promotes Glucose-responsive insulin-secretion of islet organoids matured in 3D cultures.

Media in Stage 5 (S5), the S4 medium was replaced with CMRL supplement containing 10% fetal bovine serum (ATCC), 1 µM T3, 10 µM ALKi, 0.5 µM R428, and 10 mM Nic for 7 days (FIG. 6A).

Multiplex PCR Kit (QIAGEN) using CFX Connect Real-Time PCR system (BIO-RAD). Data were normalized to an internal housekeeping gene (Cyclophilin A) and then calculated as fold change relative to differentiated cells cultured on MG using ΔΔC method. Human pancreatic RNA (Clontech) was used as positive control. For each sample, at least three independent experiments were performed. Primers are listed in Table 1.

TABLE 1

Primers and probes for qRT-PCR

| Genes | Sequences of primers and probes (5' to 3') or Assay IDs from Applied Biosystems |
|---|---|
| SOX17 | Forward: CAGCAGAATCCAGACCTGCA SEQ ID NO. 001<br>Reverse: GTCAGCGCCTTCCACGACT SEQ ID NO. 002<br>Probe: FAM-ACGCCGAGTTGAGCAAGATGCTGG-BHQ SEQ ID NO. 003 |
| FOXA2 | Forward: CCGACTGGAGCAGCTACTATG SEQ ID NO. 004<br>Reverse: TACGTGTTCATGCCGTTCAT SEQ ID NO. 005<br>Probe: FAM-CAGAGCCCGAGGGCTACTCCTCC-BHQ SEQ ID NO. 006 |
| PDX-1 | Forward: CCTTTCCCATGGATGAAGTC SEQ ID NO. 007<br>Reverse: CGTCCGCTTGTTCTCCTC SEQ ID NO. 008<br>Probe: FAM-AAGCTCACGCGTGGAAAGGCC-BHQ SEQ ID NO. 009 |
| ISL-1 | Hs00158126_m1 |
| NKx6.1 | Hs00232355_m1 |
| PTF1A | Forward: CAGGCCCAGAAGGTCATC SEQ ID NO. 010<br>Reverse: GGGAGGGAGGCCATAATC SEQ ID NO. 011<br>Probe: FAM-ATCTGCCATCGGGGCACCC-BHQ SEQ ID NO. 012 |
| Insulin | Forward: GGGAGGCAGAGGACCTG SEQ ID NO. 013<br>Reverse: CCACAATGCCACGCTTCT SEQ ID NO. 014<br>Probe: FAM-AGGTGGGGCAGGTGGAGCTG-BHQ SEQ ID NO. 015 |
| Glucagon | Forward: GCTGCCAAGGAATTCATTGC SEQ ID NO. 016<br>Reverse: CTTCAACAATGGCGACCTCTTC SEQ ID NO. 017<br>Probe: FAM-TGAAAGGCCGAGGAAGGCGAGATT-BHQ SEQ ID NO. 018 |
| MAFA | Hs01651425_s1 |
| Somatostatin | Hs00356144_m1 |
| Pancreatic polypeptide | Hs00237001_m1 |
| Cyclophilin A | 4310883E |

All differentiation media were changed every two days, unless otherwise specified.

For aggregate culture, differentiated cells at the end of stage 3 were dissociated with Dispase (STEMCELL Technologies) and further cultured in 24-well ultra-low attachment plate (Corning) with stage 4 differentiation medium for 7 days and stage 5 differentiation medium for another 7 days in a 24-well ultra-low attachment plate (Corning Life Science).

Quantitative Real-Time Polymerase Chain Reaction (qPCR)

Gene expression was evaluated by TaqMan qRT-PCR analysis as described in previous work [Nair G, Hebrok M. Islet formation in mice and men: lessons for the generation of functional insulin-producing beta-cells from human pluripotent stem cells. *Curr Opin Genet Dev* 32, 171-180 (2015); Seymour P A, Sander M. Historical perspective: beginnings of the beta-cell: current perspectives in beta-cell development. *Diabetes* 60, 364-376 (2011)]. Briefly, total RNA was isolated from cells using an RNeasy Mini Kit (Qiagen) and 200 µg of RNA from each sample was subjected to a Flow Cytometry Cells were treated with Accutase for 7 min to acquire single cell suspension. After washing with PBS, the cells were fixed in 4% paraformaldehyde (PFA) on ice for 15 min, permeablized with 0.25% Triton X-100 in PBS for 15 min, and blocked with 1% BSA in PBS-Tween at room temperature for 30 min. The following primary and secondary antibodies were used for intracellular staining: anti-insulin (Alexa Fluor 647-conjugated, 1:50, Cell Signaling), anti-Nkx6.1 (PE-conjugated, 1:20, BD Biosciences), anti-SOX17 (APC-conjugated, 1:10, R&D Systems), anti-C-peptide (1:20, DSHB at University of Iowa), anti-glucagon (1:80, R&D Systems), anti-somatostatin (1:100, Millipore), anti-pancreatic polypeptide (1:30, R&D SYSTEMS), mouse IgG (Alexa Fluor 647-conjugated, 1:20, BD Biosciences), mouse IgG (PE-conjugated, 1:40, BD Biosciences), goat IgG (APC-conjugated, 1:10, R&D SYSTEMS), goat anti-rat IgG-FITC (1:50, R&D SYSTEMS), donkey anti-mouse IgG-NL557 (1:200, R&D SYSTEMS), goat anti-rabbit-Alexa Fluor 488 (1:2000, Abcam). Flow cytometric analysis was performed on a FACS Aria II flow cytometer (Becton Dickinson) using FlowJo software (Version 10, FlowJo, LLC). Antibodies used in this study are summarized in Table 2.

TABLE 2

Antibodies used in flow cytometry

| Antibodies | Species | Manufacturer | Category | Dilution |
|---|---|---|---|---|
| Insulin | Rabbit | Cell Signaling | Primary antibody | 1:50 |
| Nkx6.1 | Mouse | BD Biosciences | Primary antibody | 1:20 |
| SOX17 | Goat | R&D SYSTEMS | Primary antibody | 1:10 |
| C-peptide | Rat | DSHB at University of Iowa | Primary antibody | 1:20 |
| Mouse IgG | Mouse | BD Biosciences | Isotype control | 1:40 |
| Mouse IgG | Mouse | BD Biosciences | Isotype control | 1:20 |
| Goat IgG | Goat | R&D SYSTEMS | Isotype control | 1:10 |
| Rat IgG | Goat | R&D SYSTEMS | Secondary antibody | 1:50 |
| Mouse IgG | Donkey | R&D SYSTEMS | Secondary antibody | 1:20 |
| Rabbit IgG | Goat | Abcam | Secondary antibody | 1:2000 |

Immunofluorescence Microscopy

Immunofluorescenct staining was carried out as described previously [Nair G, Hebrok M. Islet formation in mice and men: lessons for the generation of functional insulin-producing beta-cells from human pluripotent stem cells. *Curr Opin Genet Dev* 32, 171-180 (2015).]. In brief, cells were rinsed with PBS for three times and fixed in 4% PFA for 15 min on ice. The cells were then permeablized with 0.25% Triton X-100 in PBS and blocked with 1% BSA in PBST. Marker protein expression was labelled by incubating overnight at 4° C. with primary and secondary antibodies, anti-C-peptide (1:20, DSHB at University of Iowa), anti-glucagon (1:50, R&D Systems), anti-PDX1 (1:100, BD Biosciences), anti-MAFA (1:400, Abcam), anti-somatostatin (1:100, Millipore), anti-pancreatic polypeptide (1:50, R&D Systems), goat anti-rat IgG-FITC (1:50, R&D SYSTEMS), donkey anti-mouse IgG-NL557 (1:200, R&D Systems), goat anti-rabbit-Alexa Fluor 488 (1:1000, Abcam), goat anti-mouse-Alexa Fluor 488 (1:1000, Abcam). Nuclei were counterstained with Vectashield Mounting Medium containing 4,6-diamidino-2-phenylindole (Vector Laboratories). Images were captured using Nikon Eclipse Ti microscope. Antibodies used in immunofluorescent staining are listed in Table 3.

TABLE 3

Antibodies used in immunofluorescent staining

| Antibodies | Species | Manufacturer | Category | Dilution |
|---|---|---|---|---|
| C-peptide | Rat | DSHB at University of Iowa | Primary antibody | 1:20 |
| Glucagon | Mouse | R&D Systems | Primary antibody | 1:50 |
| PDX1 | Rabbit | Abcam | Primary antibody | 1:100 |
| MAFA | Rabbit | Abcam | Primary antibody | 1:400 |
| Somatostatin | Rat | Millipore | Primary antibody | 1:100 |
| Pancreatic polypeptide | Mouse | R&D Systems | Primary antibody | 1:50 |
| Rat IgG | Goat | R&D Systems | Secondary antibody | 1:50 |
| Mouse IgG | Donkey | R&D Systems | Secondary antibody | 1:200 |
| Rabbit IgG | Goat | Abcam | Secondary antibody | 1:1000 |
| Mouse IgG | Goat | Abcam | Secondary antibody | 1:1000 |

DTZ Staining

Dithizone (DTZ) (Sigma) was performed by first dissolving 5 mg of DTZ in 1 ml of dimethyl sulfoxide (DMSO), then diluted at 1:5 with PBS. The resultant solution was filtered through 0.2 μm nylon filter. Cellular aggregates were incubated in the DTZ solution at 37° C. for 2 to 3 minutes. Images were captured under an inverted phase contrast microscope.

Insulin Enzyme-Link Immunosorbent Assay (ELISA)

hPSC-derived cells at the end of differentiation (S5) were washed twice with PBS and preincubated in Krebs-Ringer buffer (KRB, Boston BioProducts) containing 120 mM sodium chloride, 5 mM potassium chloride, 2 mM calcium chloride, 1 mM magnesium chloride, 5.5 mM HEPES, and 1 mM D-glucose for 4 h to remove residual insulin. After rinsing twice with KRB, the cells were sequentially incubated with KRB containing 2 mM or 20 mM D-glucose or 30 mM KCl with 2 mM glucose at 37° C. for 30 min, unless otherwise specified. The respective supernatants were collected and human insulin level was measured using a human insulin ELISA kit (ALPCO Diagnostics) according to manufacturer's instructions. Total DNA content from each sample was determined by a DNeasy Blood and Tissue Kit (QIAGEN) and Synergy H1 Microplate Reader (BioTek).

Aggregates Analysis

At indicated time points, 2D cultured cells in 6-well plate were placed onto stage of a Nikon Eclipse Ti microscope and tiled bright field images were taken using 40× objective lens, covering an area of 0.53 cm2. The resulting images were analyzed by ImageJ software (National Institutes of Health, Version 1.50b). Thresholds for each were set as 0 to 200 in black and white mode. Particles whose sizes were between 10000 to 250000 μm2 and circularity between 0.18 to 1.00 were counted. Diameters of aggregates were calculated from identified areas based on the circular forms of aggregates (area=$\pi \times (d/2)^2$) where $\pi$ is circumference, and d is diameter.

Statistical Analysis

Data are presented as means±standard deviation (SD) of at least three independent experiments. Statistical analysis was calculated by Student's t-test, difference between groups were considered significant with p values<0.05.

Preparation of dpECM

Figure 1B:
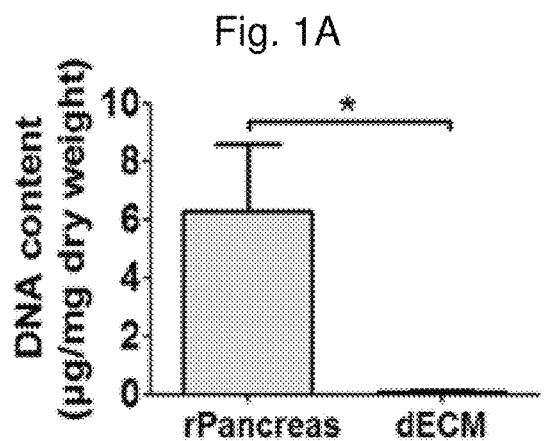
Figure 1C:
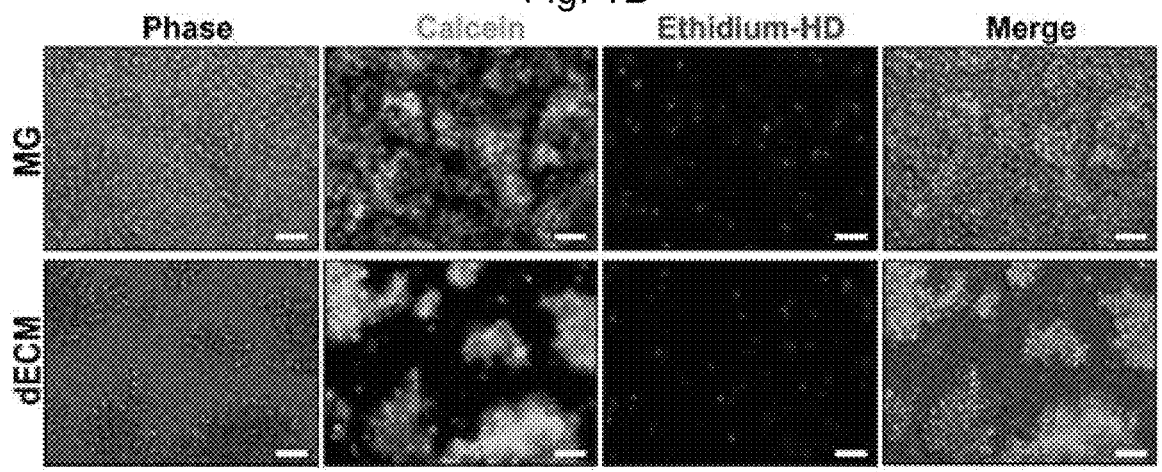
Figure 1D:
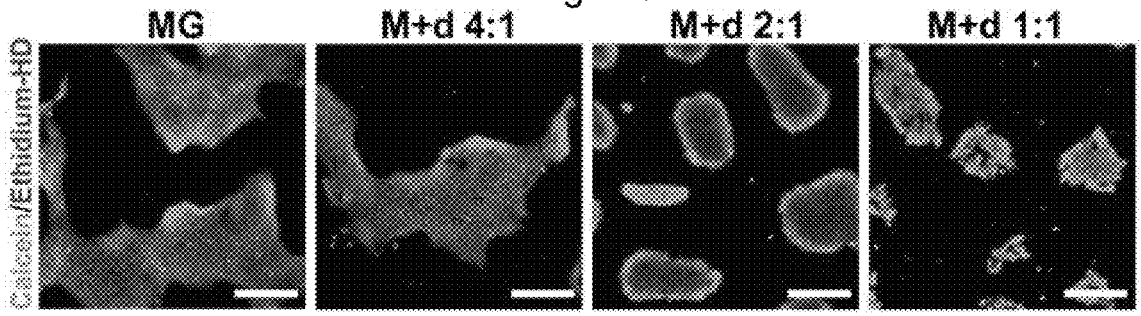

After washing by hyper/hypotonic solutions, the appearance of rat pancreata changed from bright red color to a mostly white and translucent. To assess the efficacy of decellularization, total DNAs were extracted and examined by electrophoresis. The result showed that no residual presence of cellular DNA in dpECM (FIG. 1A). Furthermore, it was confirmed that DNA content decreased from 6.26±2.31 μg/mg dry weight in normal rat pancreas to 0.06±0.05 μg/mg dry weight after decellularization (P<0.01) (FIG. 1B), indicating removal of 96% of the DNA from the tissues. By solubilizing in acetic acid with pepsin, a homogeneous and translucent dpECM gel solution was obtained. The biocompatibility of the dpECM gel was analyzed by live-and-dead cell assay. As shown in FIG. 1C, cells seeded on dpECM-coated surface revealed similar cell viability when compared to MG-coated surface. Notably, although cell culture plates coated with dpECM showed a concentration-dependent reduction in iPSCs attachment within 24 h after seeding (FIG. 8A), the cells cultured on dpECM-coated surface were able to reach 100% confluence during the 28-day differentiation protocol (data not shown). These results suggest that the decellularization process successfully removed pancreatic cellular components, the resulting dpECM solution exhibited excellent biocompatibility to support iPSCs in vitro. FIG. 1D shows live/dead cell dual-staining of iPSCs cultured on either MG or dpECM coated dishes for 24 h after seeding. Scale bars, 200 µm.

The ECM prepared using this protocol preserve growth factors and tissue niches that are essential to islet development from hPSCs. To prepare rat dpECMs, rat pancreata were treated with hyper/hypotonic solutions designed to completely remove cells from pancreatic tissues. Pancreatic tissue samples turned white and translucent after washing with hyper/hypotonic solutions. Total DNAs were extracted and examined to assess efficiency of the decellularization. Residual cellular DNA was not detected by electrophoresis in these dpECMs (FIG. 1A). The DNA content decreased from 6.26±2.31 µg/mg dry weight in normal rat pancreas to 0.06±0.05 µg/mg dry weight after decellularization (p<0.01) (FIG. 1B), suggesting successful removal of 99% of DNAs from the tissues. A homogeneous and translucent dpECM gel solution was obtained by solubilizing the dpECMs in acetic acid in the presence of pepsin.

The biocompatibility of the dpECMs was characterized through a live/dead cell assay. As shown in FIGS. 1C and 1D, cells seeded on dpECM-coated substrates revealed a cell viability similar to those grown on the MG-coated substrates, albeit cells were less attached to dpECM coated substrates (FIG. 1C). Mixing dpECM with MG improved cell attachment (FIG. 1D). Further increase of dpECM in MG appeared to suppress cell attachment within 24 hours after seeding. Nevertheless, cells were able to reach 100% confluence after culturing several days (data not shown). These experimental results suggested that dpECMs support cell growth. The mixing of dpECM with MG seems to improve cell attachment during seeding.

During experiments, it was discovered that dpECM promotes remarkably the formation of cell clusters during iPSC pancreatic differentiation in 2D cultures. The growth factors and tissue niches preserved in dpECM during decellularization appear to offer tissue-inspired niches for pancreatic endocrine development. These effects were systematically characterized, to investigate whether cell clusters formed in the presence of dpECM are actually islet organoids that are physiologically functional.

Figure 2D:
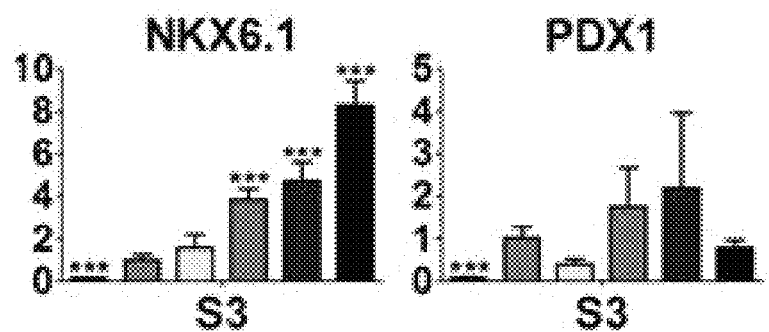

To determine the instructive effect of dpECM on hPSC pancreatic differentiation, iPSCs were differentiated on MG/dpECM coated dishes using a four stage differentiation protocol as shown in FIG. 2A, i.e. differentiating cells stepwise toward definitive endoderm (DE) (S1), posterior foregut (S2), pancreatic progenitor (S3), and hormone-expressing endocrine cells (S4). To interrogate whether the instructive effect of dpECM on iPSC pancreatic differentiation is dose-dependent, culture plates were coated with MG/dpECM mixtures at different ratios (4:1, 2:1, and 1:1). It is clear that the addition of dpECM to MG substrates enhanced directed differentiation of iPSCs toward pancreatic lineages. Key pancreatic endocrine marker genes, including PDX-1, insulin, Ptf1α, Nkx6.1, and MafA, expressed at much higher levels in cells differentiated on MG/dpECM coated plates (FIG. 2B-E), suggesting an instructive effect of dpECMs on iPSC pancreatic lineage specification. It seemed that an increase in dpECM concentration in the MG/dpECM mixture stimulated higher degree of pancreatic lineage specification at Stage 3, a key stage of pancreatic endocrine development. The expression levels of PDX1 and NKX6.1 in cells differentiated on 2:1 mixed MG/dpECM coated plates were much higher than those differentiated on 4:1 mixed MG/dpECM coated plates. Further increase in dpECM concentrations does not appear to enhance iPSC pancreatic differentiation. Accordingly, a 2:1 mixed MG/dpECM matrix was used for the subsequent experiments. The flow cytometric analysis confirmed these observations. While SOX17$^+$ DE cells reached 98% at the end of Stage 1 in all conditions, 84.1% cells expressed a high level of SOX17 when differentiated on MG/dpECM coated plates, whereas only 64.6% cells reached a high level of SOX17 expression in cells differentiated on MG coated plates (FIG. 8B).

Figure 10:
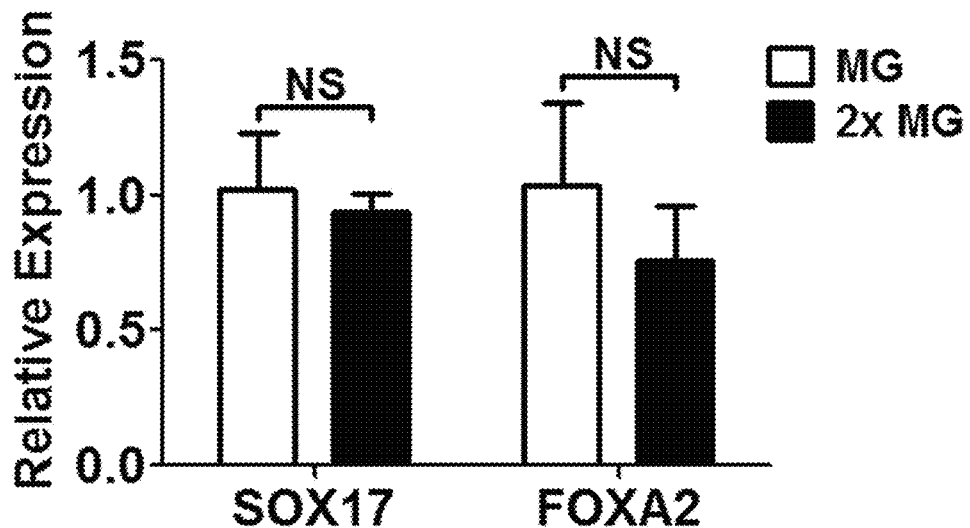
FIG. 10 shows a comparison of iPSC DE differentiation on MG with those on MG/dpECM substrates. TaqMan qPCR analysis of SOX17 and FOXA2 expression in cells at the end of DE stage. Cells cultured on MG-coated (MG) or two-fold increased MG ECM coated substrates (2× MG). Expression levels were normalized to that in cells cultured MG-coated dish. Values are shown as mean±SD (n=3). NS: not statistically significant.

Further investigation measured whether increase in the amount of MG coated on culture plates has a similar effect on iPSC pancreatic differentiation. As shown in FIG. 10, the expression of SOX17 and FOXA2, two DE marker genes, were at almost the same level in cells differentiated on MG or 2×MG (doubling the amount of MG used for coating) coated plates. It is clear that the increase in coating matrix does not contribute to the enhancement of iPSC pancreatic lineage specification. The preferential factors entailed in dpECM promoted the iPSC pancreatic differentiation.

Figure 3A:
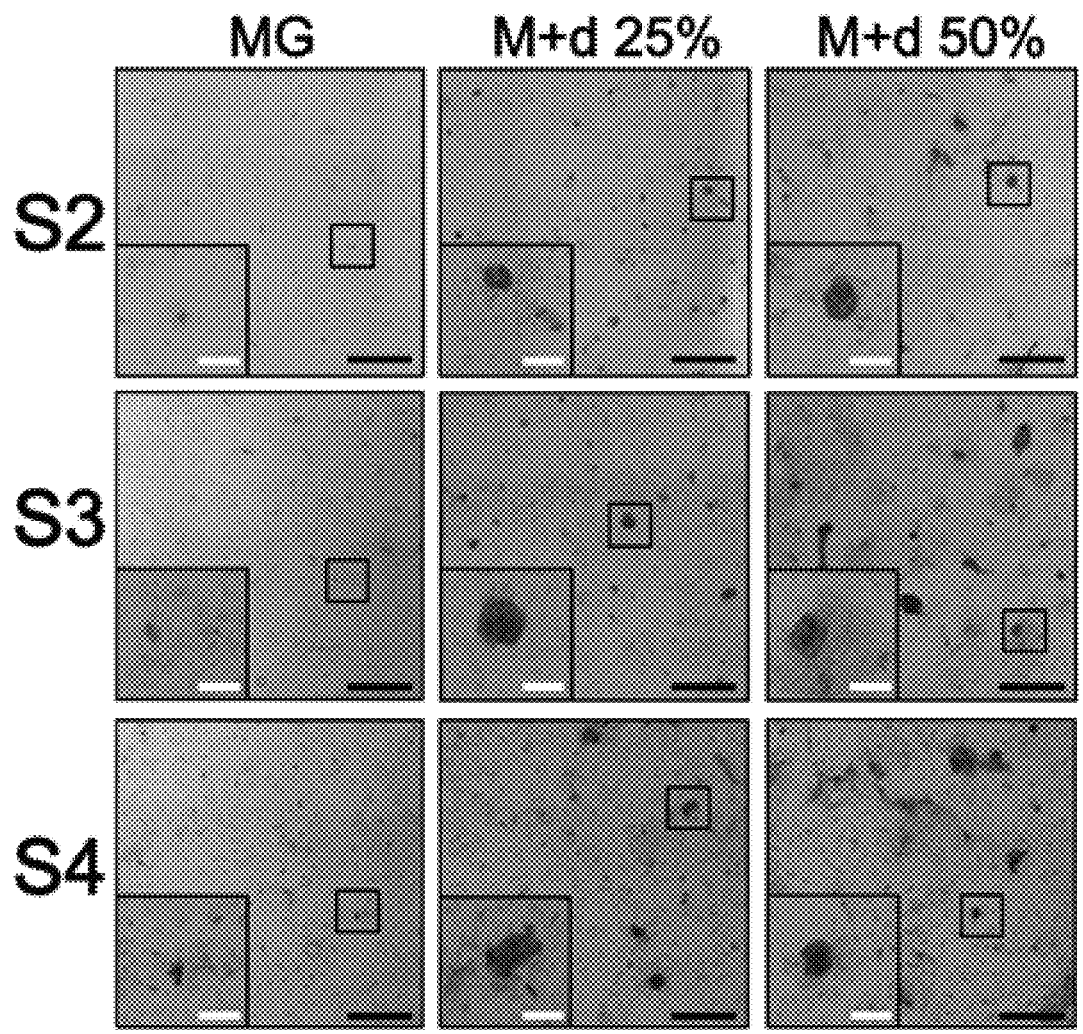

Starting from S2, significant amount of self-assembled clusters were constantly observed to appear in dpECM/MG-coated plates compared with that of MG-coated plates (FIG. 3A). Clusters larger than 100 µm in diameter were considered as organoids and evaluated them by quantitative image analysis. The results showed that higher number of organoids were found on 2:1 mixed MG/dpECM substrates than 4:1 mixed MG/dpECM substrates, while MG only coating failed to generate organoids, albeit smaller condensed colonies ultimately appeared (FIG. 3B). To determine the size distribution of the organoids, the diameter of each identified organoid from S2 to S4 was monitored. The organoids formed on dpECM coated condition have large variance in size ranging from 100 µm to 430 µm, while no aggregate larger than 200 µm was found on MG only coating (FIG. 3C). These experimental data confirm the presence of dpECM induces self-assembly of organoids during pancreatic differentiation. The same phenomenon has been confirmed as well during differentiation process from human ESC line H9 cells (data not shown).

Figure 2E:
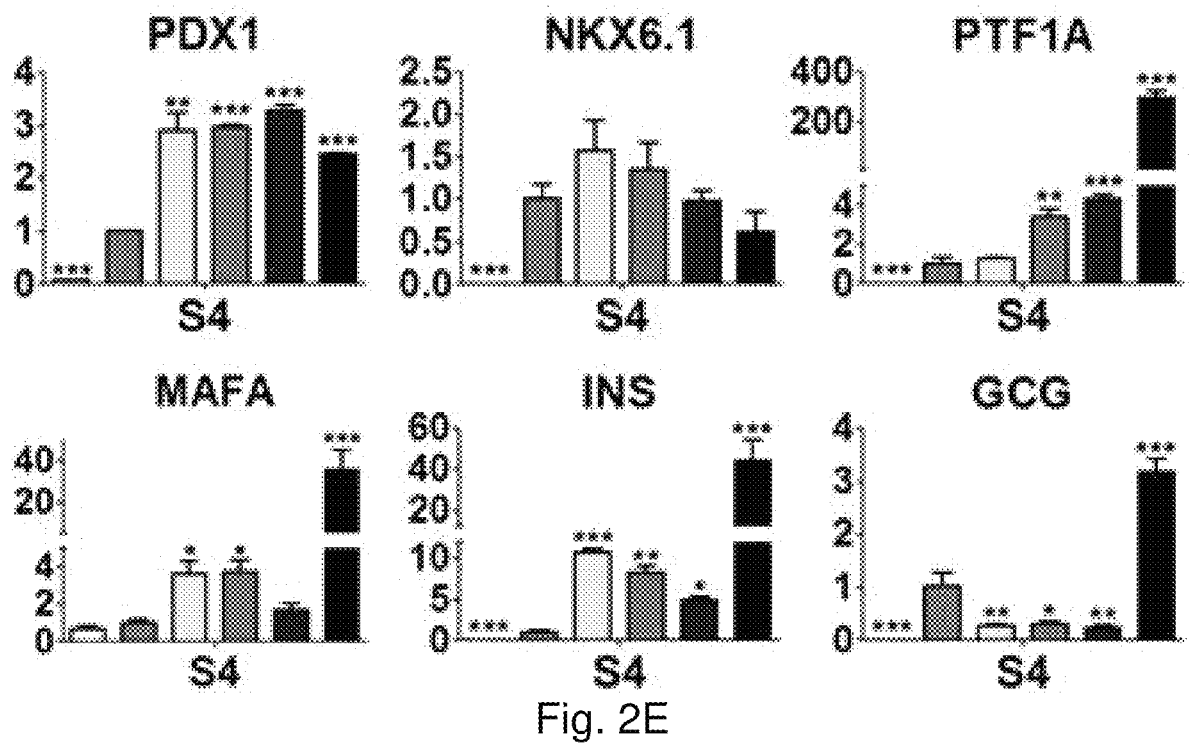

The organoids formed on dpECM coated condition have large variance in size.

dpECM Enhances the Expression of Pancreatic Marker Genes During hPSC Islet Tissue Differentiation FIGS. 2A-2E shows a schematic summary of the 4-stage, 21-day differentiation protocol and characterization of marker genes during the differentiation. FIG. 2A shows in vitro differentiation protocol of iPSCs to islet tissue. Basal media as well as key molecules used are shown for each stage of differentiation. FIGS. 2B-2E show the profile of marker gene expression of hPSC-derived cells during 51 to S4 of differentiation. Cells were 2D cultured on MG- or MG-/dpECM-coated substrates using indicated concentrations. Expression levels of mRNA were assessed for DE (FIG. 2B), posterior foregut (FIG. 2C), pancreatic progenitor (FIG. 2D), and β-cell markers (FIG. 2E). Gene expression was relative to that in cells grown on MG-coated dishes. Results were from three or more experiments and shown as mean±SD. *, $p<0.05$; , $p<0.01$; *, $p<0.001$, compared to MG group. Cells were 2D cultured on MG or MG/dpECM (M+d) coated plates as described in Methods. The MG-dpECM ratios (w:w) of prepared MG/dpECM mixtures were 4:1, 2:1, and 1:1, respectively.

To determine the regulative role of dpECM in pancreatic differentiation, iPSCs cultured on various concentrations of dpECM coating were differentiated by a four-stage differentiation protocol through definitive endoderm (S1), posterior foregut (S2), pancreatic progenitor (S3), and hormone-expressing endocrine cells (S4) (FIG. 2A). Cells grown on dpECM/MG-coated substrates demonstrated higher levels of gene expression for most of the key markers compared with cells cultured on MG-coated substrates (FIGS. 2B-E). Particularly, mRNAs of PDX-1, insulin, Ptf1α, Nkx6.1, and MafA from cells grown in dpECM/MG-coated substrates showed multiple folds' enhancement at each stage of differentiation.

Figure 9:
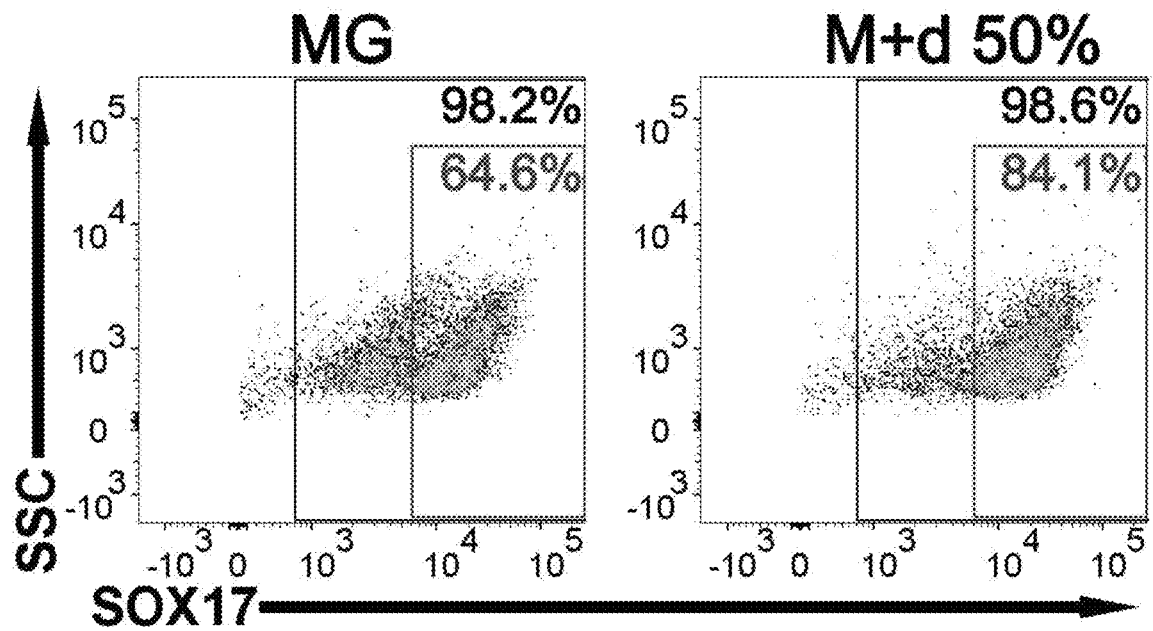
FIG. 9 shows flow cytometry analysis of SOX17 expression in DE stage. SOX17-positive cells were gated using isotype control (Black square). Red square indicates the percentage of cells expressing high level of SOX17.

Differentiation efficiency was also assessed by flow cytometric analysis. Cells cultured on either coating condition tested possessed more than 98% of SOX17+ cells at the end of definitive endoderm (DE) stage (S1) (FIG. 9). There were 84.1% of DE cells possessing higher level of SOX17 expression from cells cultured on dpECM/MG-coated substrates as compared to 64.6% from cells cultured on MG-coated substrates (FIG. 9). This result is consistent with quantitative analysis of gene expression (FIG. 2B).

To rule out the possibility of the increased gene and protein expression in dpECM-containing groups was caused by higher amount of protein coated on culture plates compared with MG group, the expression of DE marker genes was evaluated in cells cultured on MG-coated with the same amount of dpECM/MG proteins as described in Materials and Methods (FIG. 10). Experimental results indicate that cells cultured on increased ECM amount of MG-coated substrates expressed similar levels of both SOX17 and FOXA2 genes compared with cells cultured on regular MG-coated plate. This experimental result suggests that, first of all, the amount of MG coating is sufficient for stem cell attachment, proliferation and differentiation. Further increase in the amount of MG for plate coating has no influence on stem cell attachment and differentiation. Second, the augmentation of efficiency of hPSC-derived endocrine differentiation is indeed contributed by dpECM.

dpECM Triggers the Self-Assembly of Islet-Like Organoids During hPSC Pancreatic Differentiation FIGS. 3A-3C show microscopic examination of self-assembly of islet-like organoids at the end of stage 2, 3, and 4 of iPSC differentiation. Black bars, 1000 µm; white bars, 200 µm. Tiled images covering an area of 0.53 cm$^2$ were randomly selected and analyzed by ImageJ software. Data are shown as mean±SD (n=8). *, p<0.05; , p<0.01; *, p<0.001. FIG. 3A show micrographs of cell clusters formed on MG/dpECM coated plates. Black scale bars, 1,000 µm; white scale bars, 200 µm. FIG. 3B shows number of cell clusters formed on MG/dpECM coated plates. Tiled images covering an area of 0.53 cm2 were randomly selected and analyzed by ImageJ software. Data are shown as mean±SD (n=8). *, p<0.05; , p<0.01; *, p<0.001. FIG. 3C show diameters of cell clusters formed on MG/dpECM coated plates. Gray bars indicate average diameter of aggregates.

It was observed that cells grown on dpECM/MG-coated substrates started forming aggregates from Stage 2 of differentiation and these aggregates grew to the end of the entire differentiation (FIGS. 3A-3C). Significant number of aggregates self-assembled in dpECM/MG-substrates compared with that of MG-coated substrates. Clusters larger than 100 µm in diameter were considered as organoids and then quantitatively evaluated them by quantitative image analysis. The results showed that dpECM triggered e the formation of organoids in a dose-dependent manner, while MG only coating failed to generate organoids, albeit smaller condensed colonies ultimately appeared.

Organoids formed by self-organizing stem cells recapitulate complex cell-cell interactions during de novo generation of 3D islet-like clusters. As such, they harbor geometric constraints and environmental cues that are essential for islet neogenesis [Greggio, Chiara, Filippo De Franceschi, and Anne Grapin-Botton. "Concise Reviews: In Vitro-Produced Pancreas Organogenesis Models in Three Dimensions: Self-Organization From Few Stem Cells or Progenitors." Stem Cells 33, no. 1 (2015): 8-14]. To determine the size distribution of the organoids, the diameter of each identified organoid was monitored from S2 to S4. The organoids formed with large variance in size, and with increasing numbers of large organoids (diameter>200 µm) on dpECM coated condition, confirming that the presence of dpECM induces self-assembly of organoids during pancreatic differentiation.

iPSCs Differentiated on dpECM Exhibit Similar Cellular Composition to Pancreatic Islets The organoids shown in FIGS. 3A-3C were hypothesized to be islet organoids having fetal status. To characterize the identity of these organoids formed on dpECM-coated substrates, the organoids at the end of S4 were investigated regarding expression of islet signature composition through immunofluorescence staining and flow cytometric analyses.

Figures 4A, 4B:
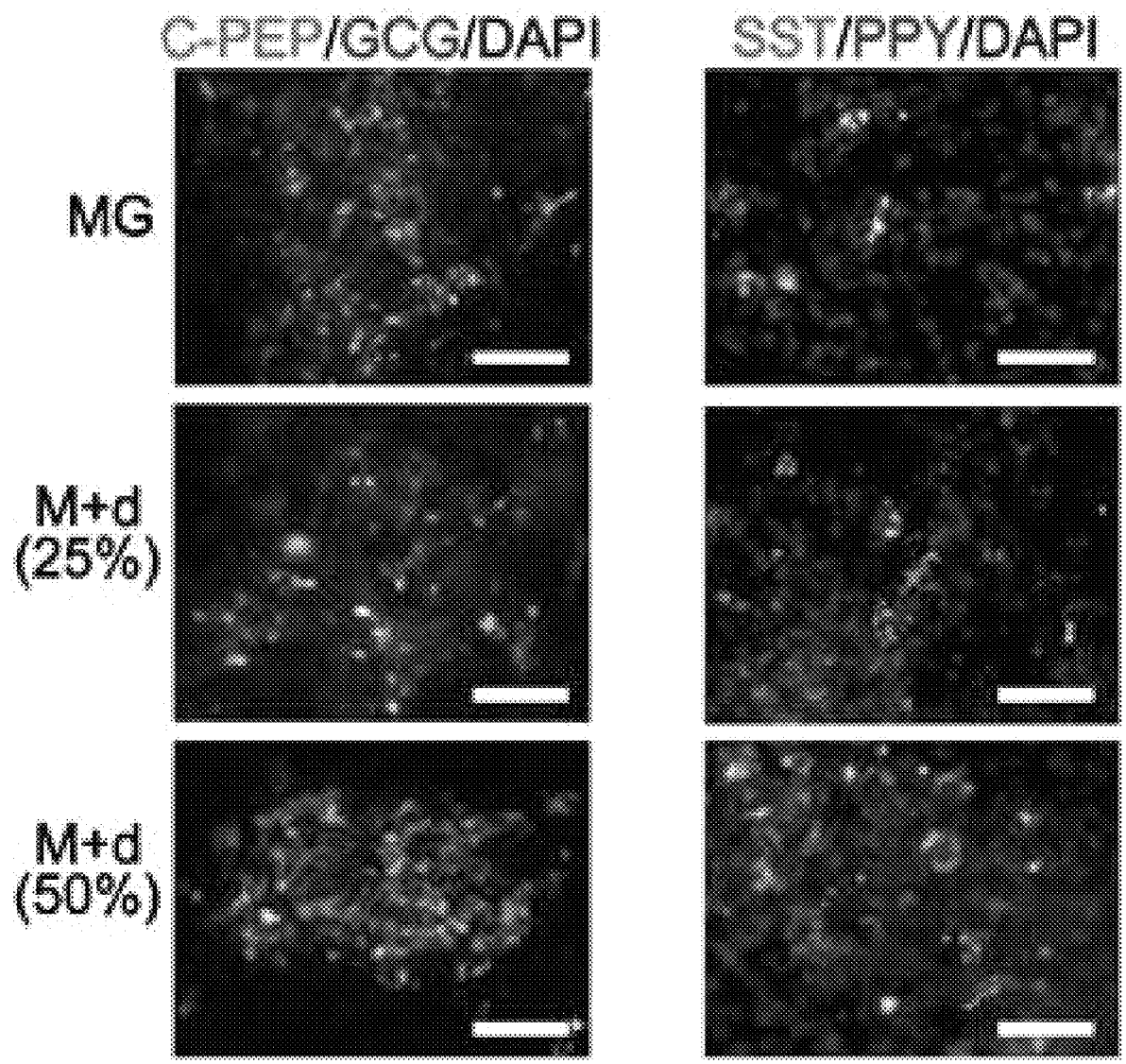
FIGS. 4A-4E show organoids generated from iPSCs grown on dpECM coated substrates showed similar composition to native islets.
Figure 4C:
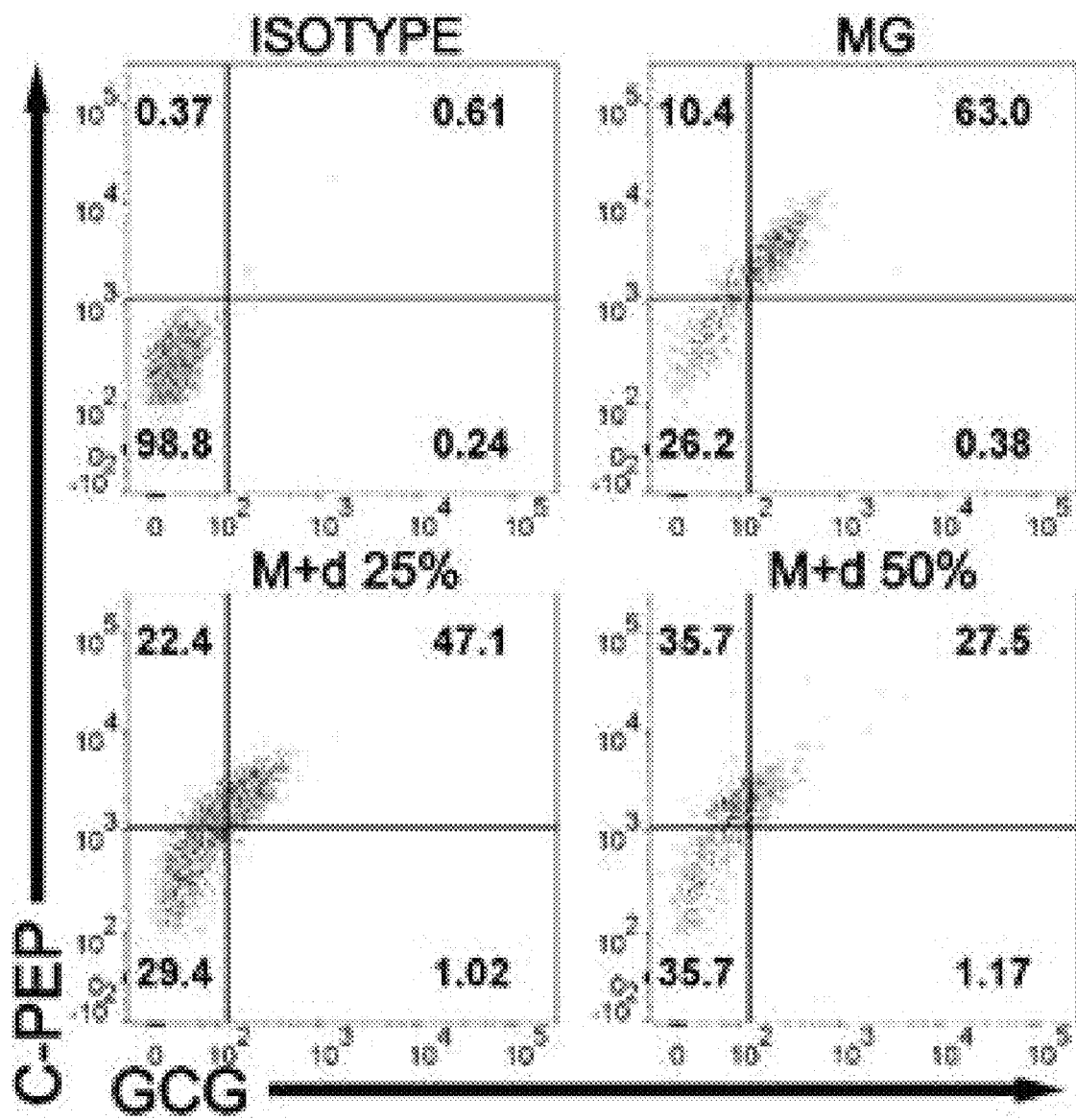
Figure 4D:
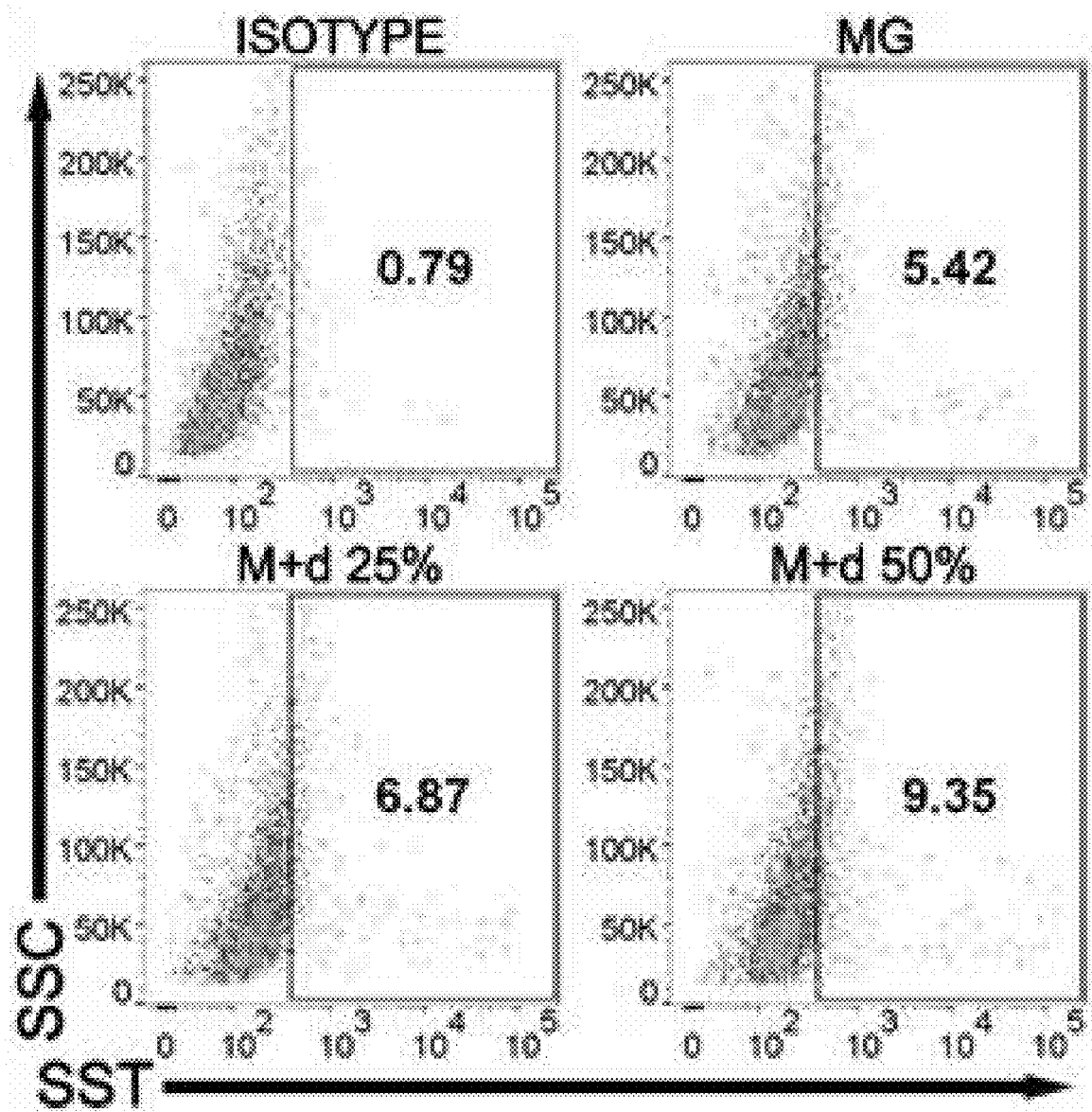
Figure 4E:
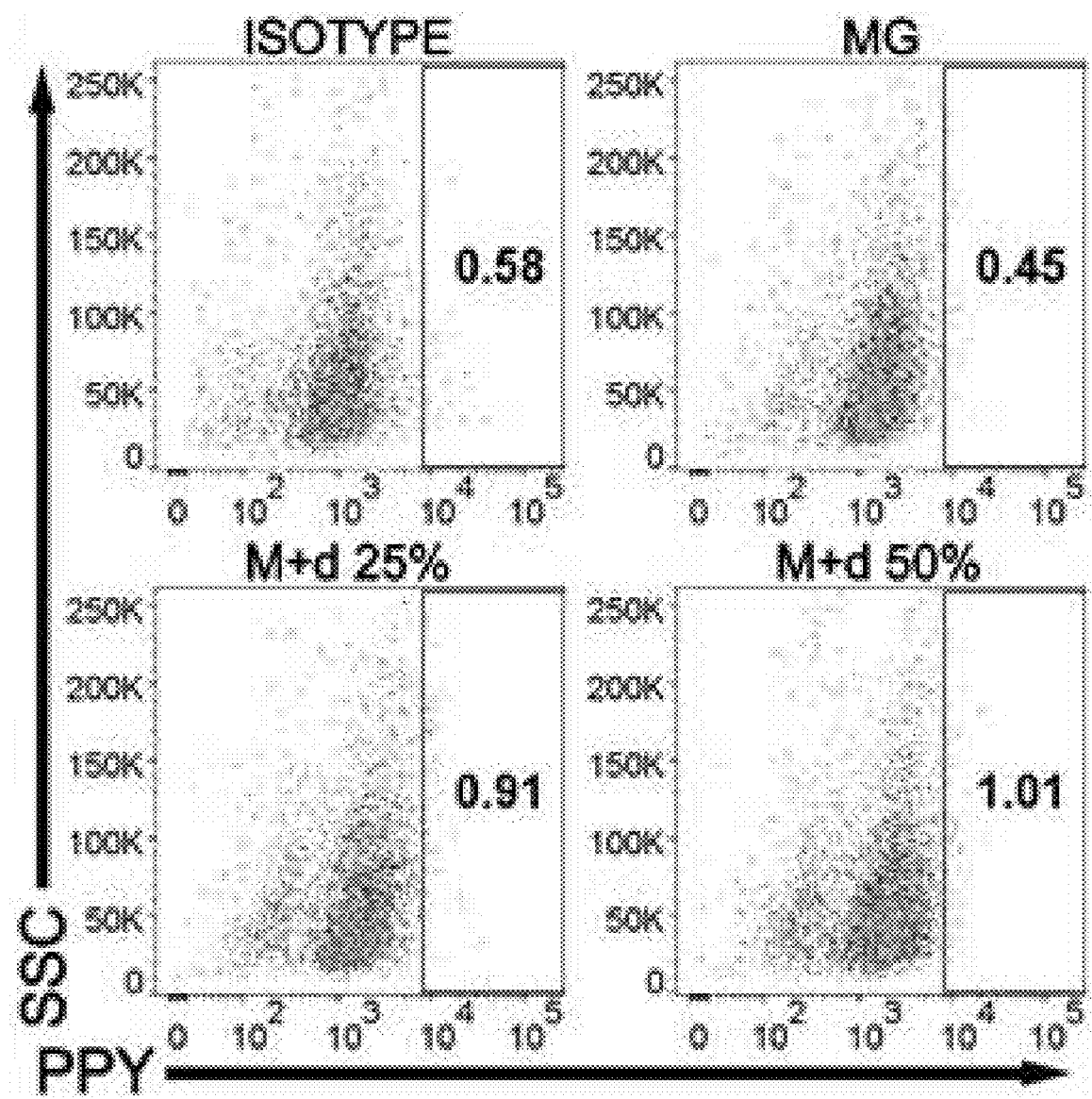

FIGS. 4A-4E show organoids generated from iPSCs grown on dpECM coated substrates showed similar composition to native islets. FIG. 4A shows representative immunofluorescent staining of S4 cells labeled for C-peptide (C-PEP, green) and glucagon (GCG; red). 4,6-diamidino-2-phenylindole (DAPI, blue) was used for counterstaining nuclei. Scale bars, 50 µm. FIG. 4B shows representative immunofluorescent staining of S4 cells labeled for somatostatin (SST, green), pancreatic polypeptide (PPY; red), and DAPI. Scale bars, 50 µm. (FIGS. 4C-4E) Representative flow cytometric results of S4 cells stained for C-PEP and GCG (FIG. 4C), SST (FIG. 4D), and PPY (FIG. 4E). Numbers in quadrants represent the percentage of total counted cells.

FIGS. 4F-4L show cell compositions of S4 cells during iPSC pancreatic differentiation on MG/dpECM coated plates. S4 cells were immunofluorescently labeled for (FIG. 4F) C-peptide (C-PEP, green) and glucagon (GCG; red); (FIG. 4G) somatostatin (SST, green) and pancreatic polypeptide (PPY; red). 4,6-diamidino-2-phenylindole (DAPI, blue) was used for counterstaining cell nuclei. Scale bars, 50 µm. (FIGS. 4H-4I) Representative flow cytometric analysis of C-PEP (FIG. 4H), GCG (FIG. 4I), SST (FIG. 4J), and PPY (FIG. 4K) expressing cells in S4 cells. SSC: side scatter. (FIG. 4L) Representative flow cytometric analysis of S4 cells dual-stained for C-PEP and GCG. Numbers in quadrants represent the percentage of total counted cells.

As revealed by FIG. 4A, more C-peptide (C-PEP)-positive cells are detected from cells grown on dpECM/MG-coated substrates compared to those on MG-coated surface. Interestingly, the C-PEP+ cells identified on high dpECM/MG coating showed a clustered pattern, while they were scattered randomly through the entire cells cultured on MG coating (FIG. 4A). Remarkably, although C-PEP and glucagon (GCG)-dual positive cells were identified in all culture conditions (FIG. 4A), the percentage of polyhormonal cells decreased in a dpECM dose-dependent manner. In contrast, C-PEP+/GCG-cells significantly increased from approximately 10% on MG to 35% on dpECM substrates (FIG. 4C), suggesting dpECM helps maturation of islet tissues during hPSC-derived islet development. Notably, the overall C-PEP+ cell population was higher than 60% (FIG. 4C), indicating an effective development of islet-like organoids.

Similar to INS+ and GCG+ cells, the somatostatin (SST)-positive and pancreatic polypeptide (PPY)-positive population showed a more notable increment on dpECM coating condition, although they constituted a minority in differentiated cells (FIG. 4B). In contrast to the other three cell types, PPY+ cells were hardly detectable on MG coating condition. Flow cytometry analysis enumerated that on dpECM/MG-coated substrates higher proportion of SST+ cells and PPY+ cells, which contributed to 9.35% and 1.01% of the total cell population, respectively, could be achieved (FIGS. 4D and 4E). These data illustrated a comparative ratio to that of human islet, in which 50-70% of the cells are β-cells, 20-30% are α-cells, ≈10% are δ cells, and <5% are PP cells [Shih H P, Wang A, Sander M. Pancreas organogenesis: from lineage determination to morphogenesis. *Annu Rev Cell Dev Biol* 29, 81-105 (2013); Jennings R E, et al. Development of the human pancreas from foregut to endocrine commitment. *Diabetes* 62, 3514-3522 (2013); Rose S D, Swift G H, Peyton M J, Hammer R E, MacDonald RJ. The role of PTF1-P48 in pancreatic acinar gene expression. *J Biol Chem* 276, 44018-44026 (2001).]. Taken together, the hPSCs differentiated on dpECM niches demonstrated similar cellular arrangement to an islet, suggesting dpECM provides necessary microenvironmental context that is required for the development of islet organoids. It implies that dpECM niches permit self-organizing an islet tissue during hPSC differentiation even in a 2D culture condition.

To determine whether cell clusters formed from iPSCs in the presence of dpECM are islets or islet organoids, cell compositions and architectures of cells collected were characterized at end of S4. The expression of pancreatic endocrine hormones such as c-peptide (C-PEP, a peptide released from the pancreatic beta-cells during cleavage of insulin from proinsulin), glucagon (GCG), somatostatin (SST), and pancreatic polypeptide (PPY) in cell clusters were detected using immunostaining.

Figures 4F, 4G:
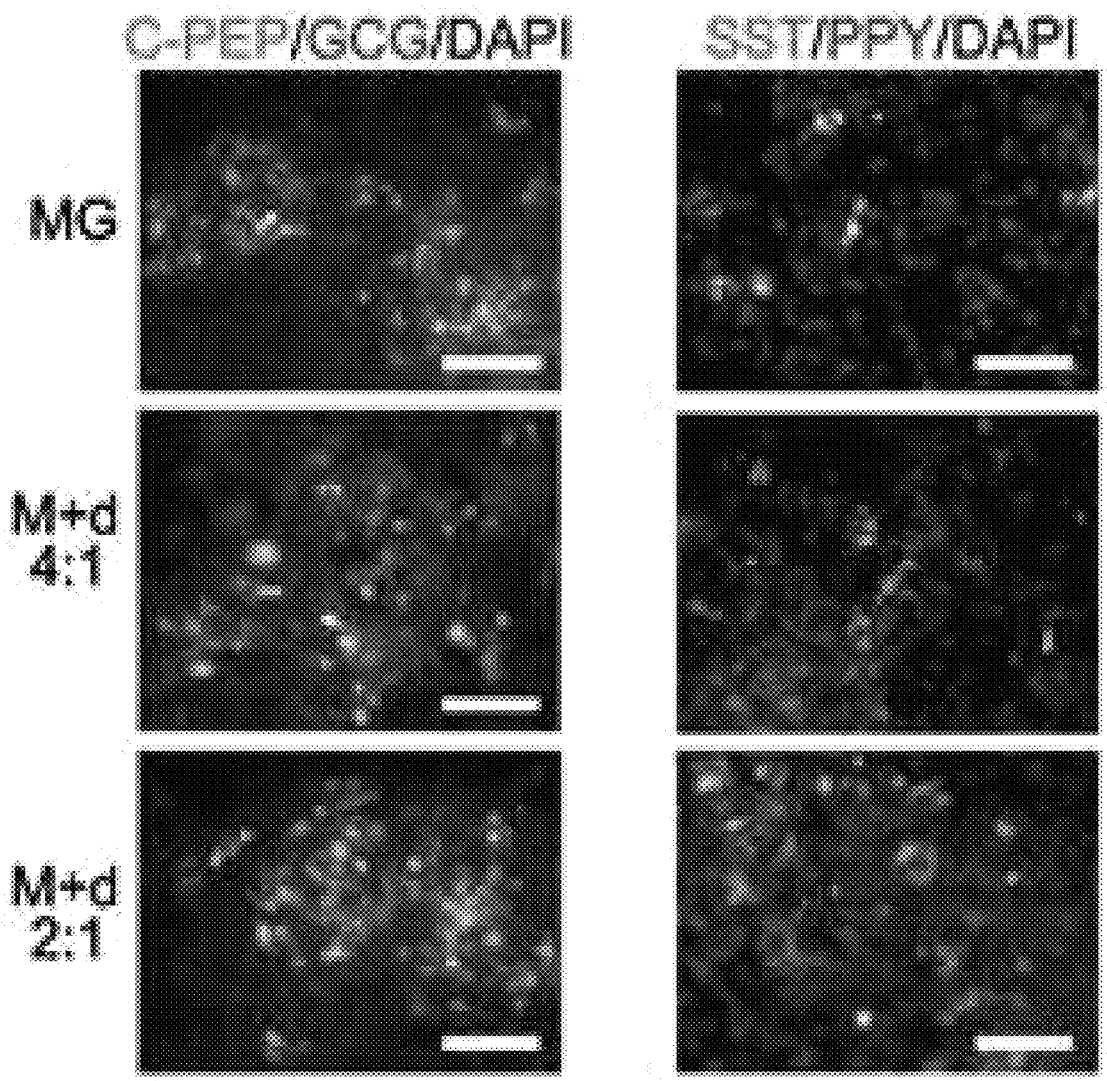
FIGS. 4F-4L show cell compositions of S4 cells during iPSC pancreatic differentiation on MG/dpECM coated plates. S4 cells were immunofluorescently labeled for (FIG. 4F) C-peptide (C-PEP, green) and glucagon (GCG; red)
Figure 4H:
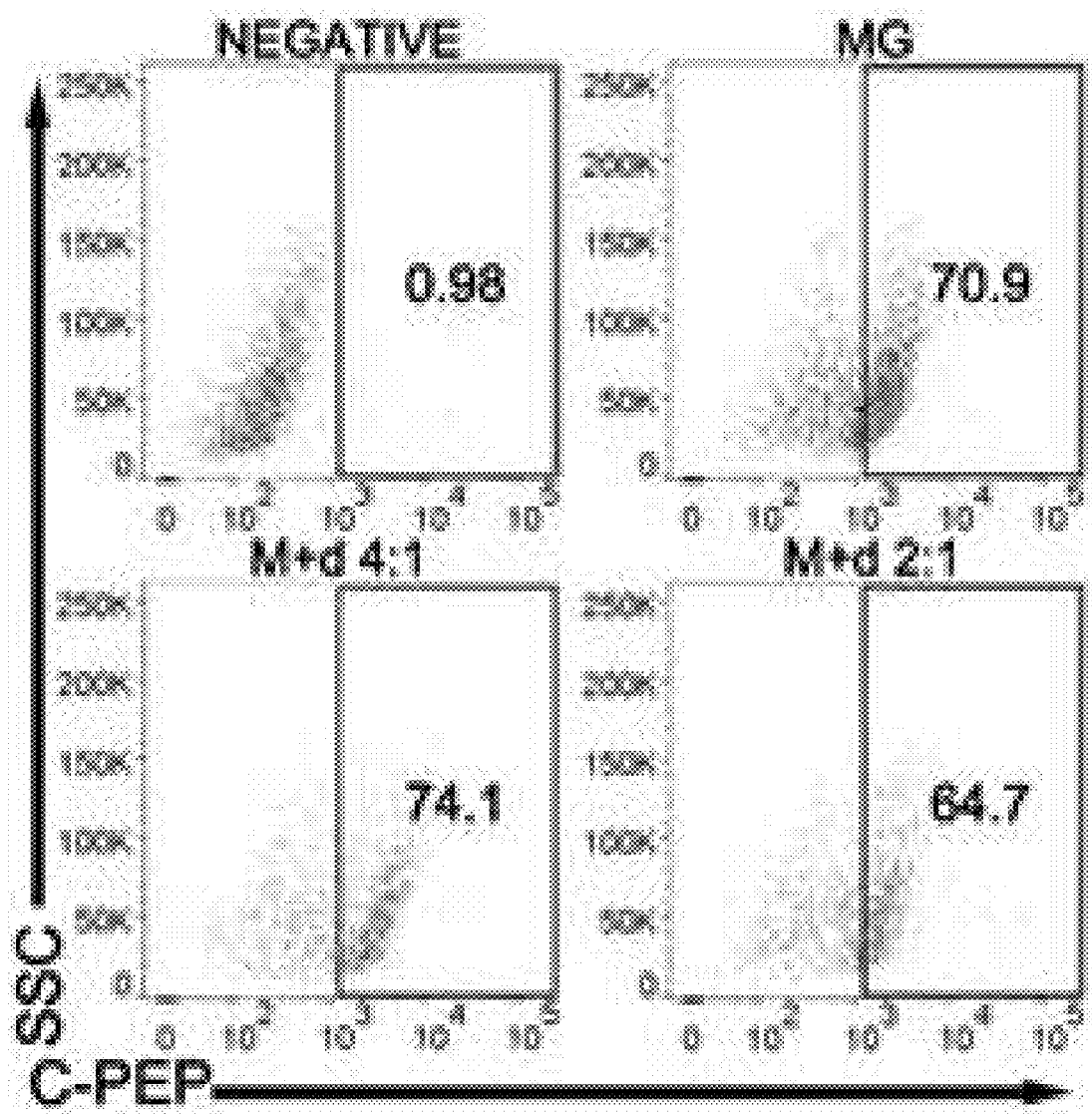
Figure 4I:
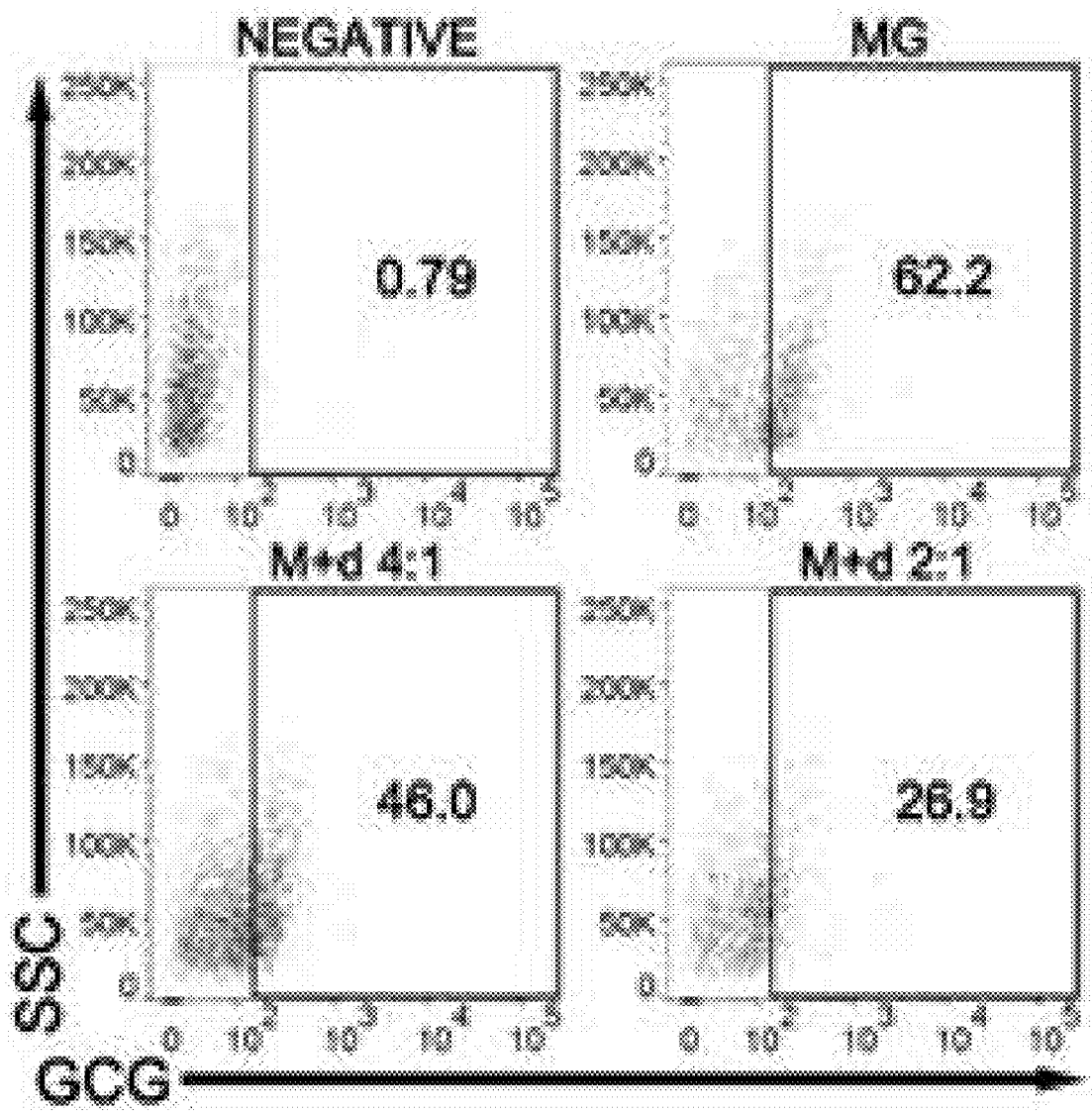
Figure 4J:
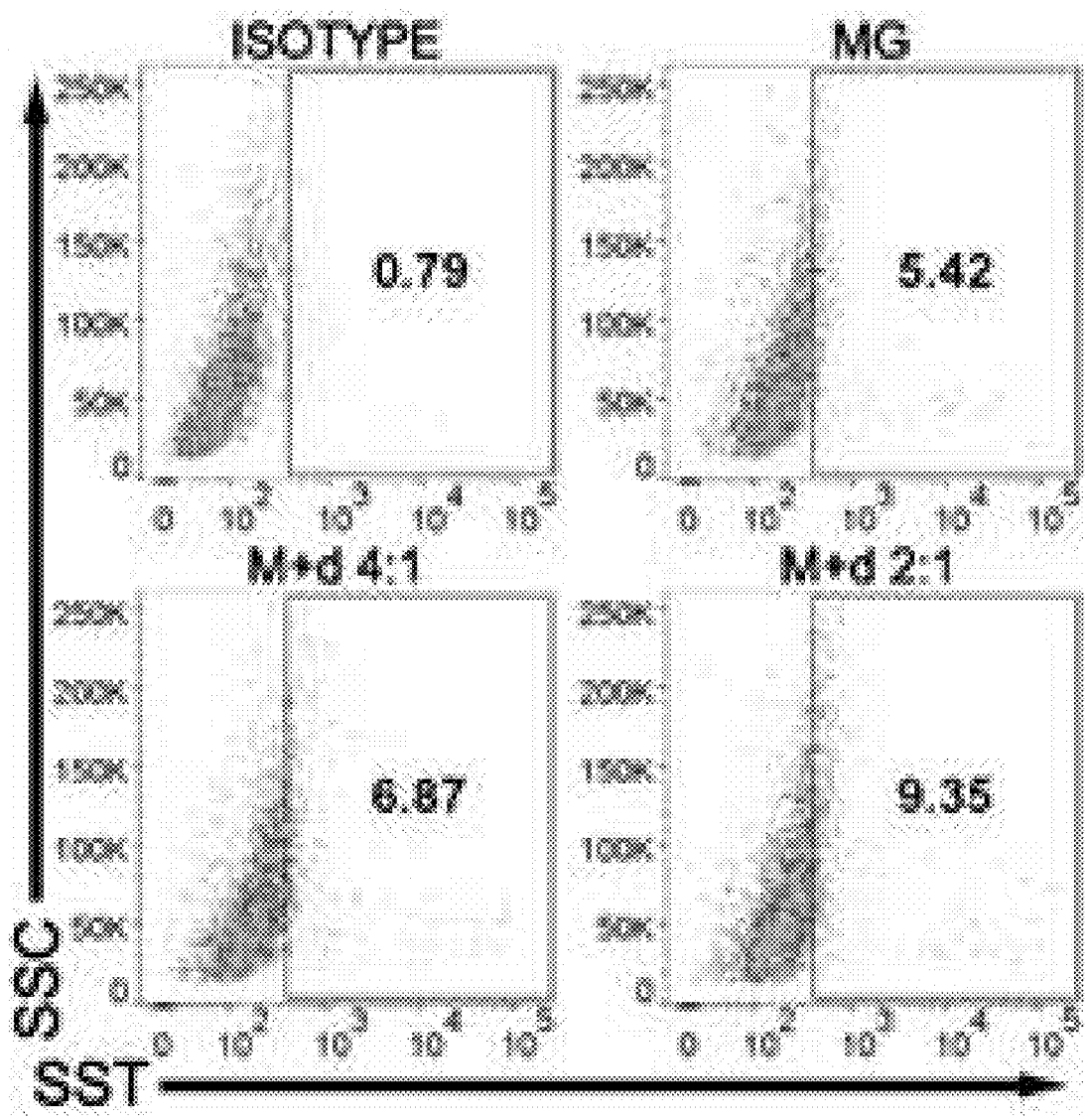
Figure 4K:
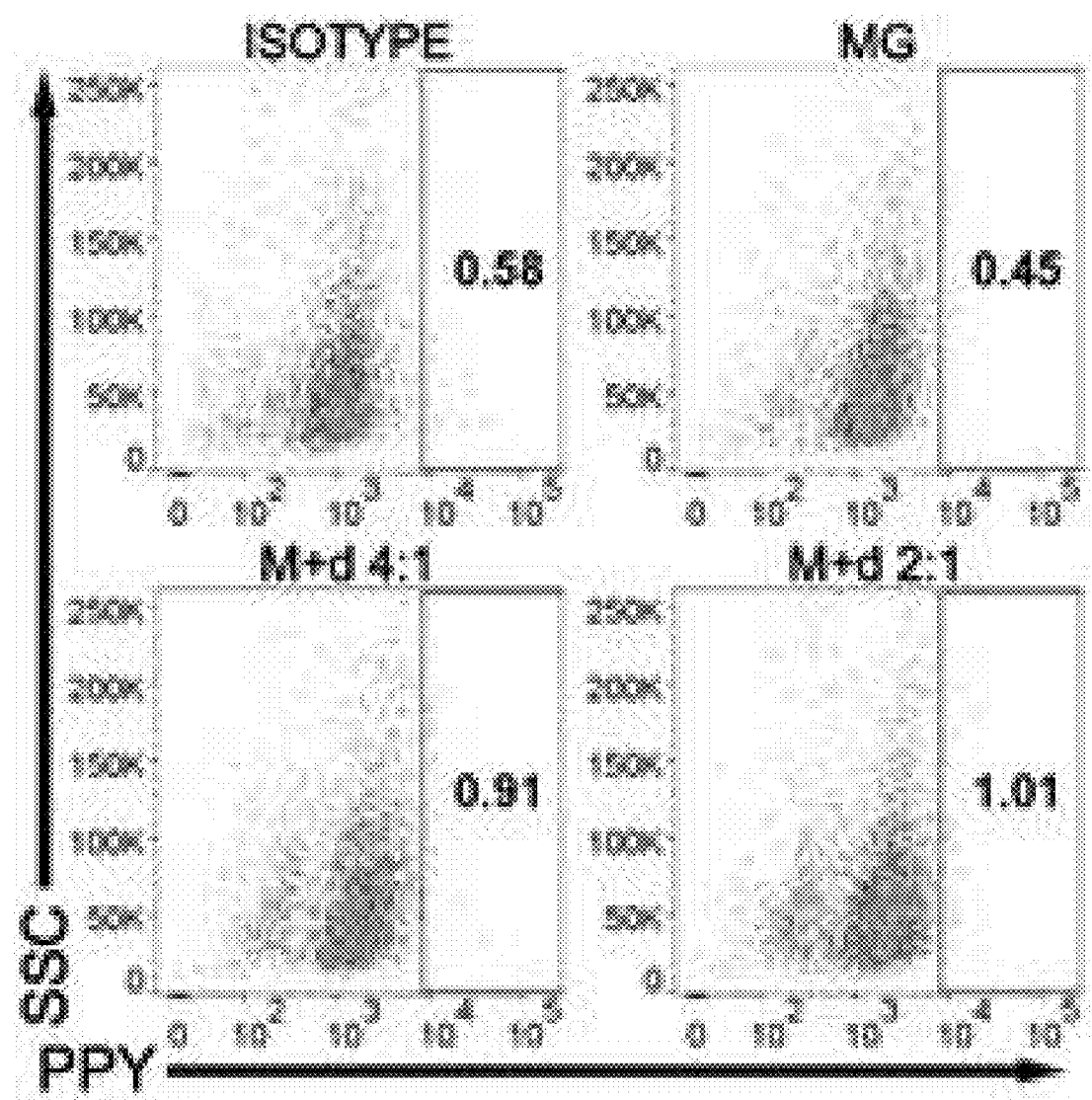

As shown in FIG. 4F-4G, GCG, SST, and PPY were expressed in small subsets of cells that were mixed with insulin-secreting cells. Flow cytometry data showed that more than 60% of S4 cells expressed C-PEP among all differentiation conditions (FIG. 4H), where GCG$^+$ cells decreased significantly from 53.43±12.40% of cells differentiated on MG to 39.91±8.61% and 31.36±6.31% of cells differentiated on 4:1 and 2:1 mixed MG/dpECM substrates, respectively (FIG. 4I). SST$^+$ cells were increased from 4.85±0.81% on MG to 5.81±2.39% on 4:1 mixed MG/dpECM and further upraised to 10.13±1.10% on 2:1 mixed MG/dpECM substrate (FIG. 4J). Similarly, the population of PPY$^+$ cells increased from 0.50±0.07% on MG to 0.72±0.28% and 1.06±0.07% on 4:1 and 2:1 mixed MG/dpECM substrates, respectively (FIG. 4K). These results suggested cells differentiated on 2:1 mixed MG/dpECM substrates showed similar cellular arrangement to islet, which possess comparative cellular proportions to that of human islet, in which 50-70% of the cells are β-cells, 20-30% are α-cells, ≈10% are δ cells, and <5% are PP cells [Stefan Y, Orci L, Malaisse-Lagae F, Perrelet A, Patel Y, Unger R H. Quantitation of endocrine cell content in the pancreas of nondiabetic and diabetic humans. *Diabetes* 31, 694-700 (1982); Ichii H, et al. A novel method for the assessment of cellular composition and beta-cell viability in human islet preparations. *Am J Transplant* 5, 1635-1645 (2005); Brissova M, et al. Assessment of human pancreatic islet architecture and composition by laser scanning confocal microscopy. *J Histochem Cytochem* 53, 1087-1097 (2005)].

Figure 4L:
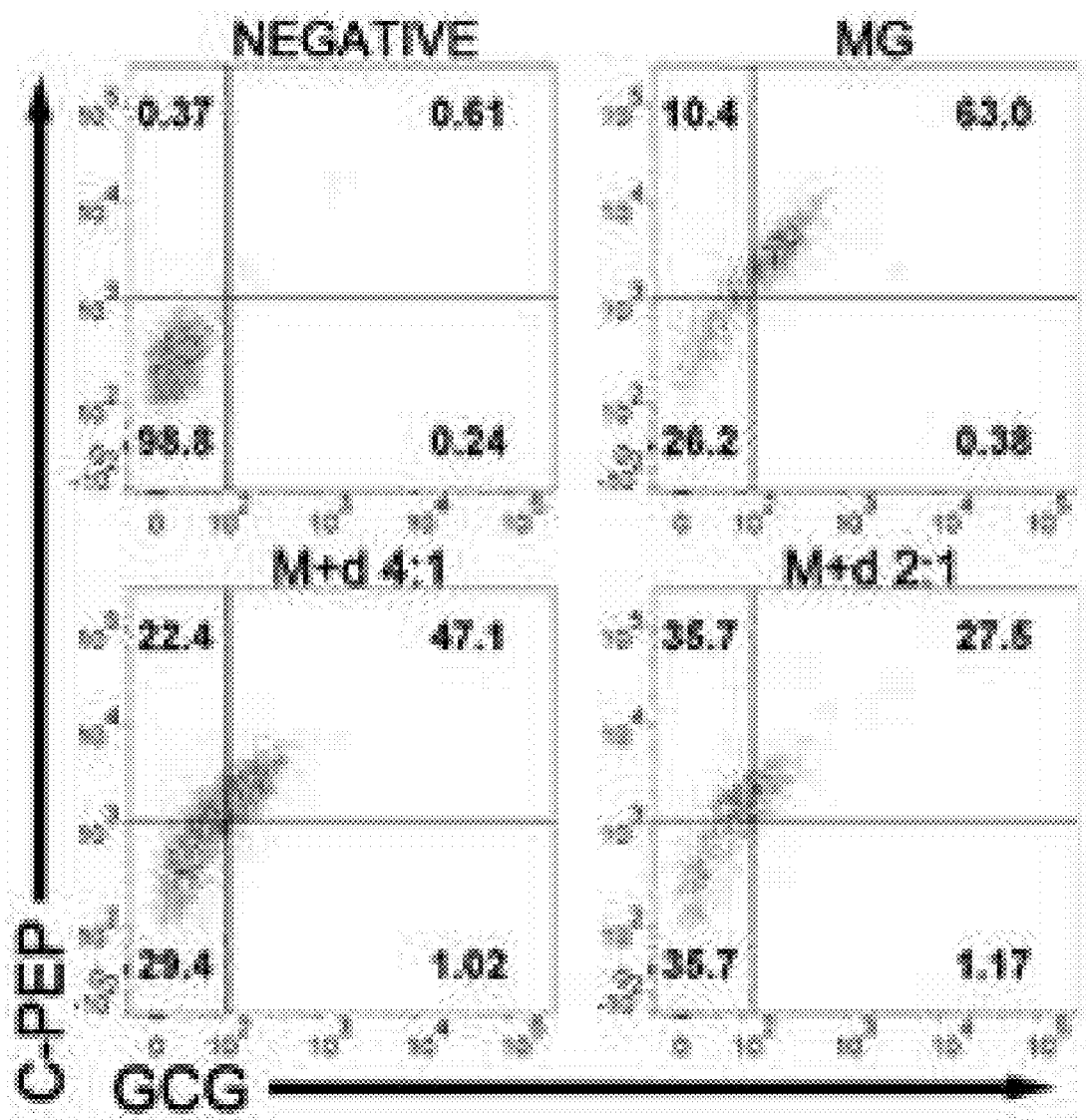

Nevertheless, some insulin-secreting cells co-expressed glucagon as shown in FIG. 4L, 53.80±13.01% of cells differentiated on MG coated plates co-expressed C-PEP and GCG, suggesting their low maturity. In contrast, the percentage of C-PEP and GCG polyhormonal cells was reduced in cell clusters formed on MG/dpECM coated plates: 40.40±9.48% of cells cultured on 4:1 mixed MG/dpECM substrates, whereas only 31.65±5.87% of cells cultured on 2:1 mixed MG/dpECM substrate. Together, these results suggest using dpECM as a culture substrate can improve islet organogenesis and maturation during in vitro differentiation of hPSCs.

To further characterize the iPSCs-derived organoids under MG/dpECM substrates, co-expression of insulin (INS) and NKX6.1 was detected in cells collected at the end of S4 by flow cytometric analysis. About 29.0%, 26.9% and 21.3% of cells co-expressed INS and NKX6.1 in cells differentiated on 2:1 and 4:1 mixed MG/dpECM, and MG substrates, respectively (FIG. 4F). The Insulin-secreting cells were 40.4%, 41.4% and 37.7% in cells differentiated on 2:1 and 4:1 mixed MG/dpECM, and MG substrates, respectively. These experimental results supported the hypothesis that dpECM encourages self-assembly of cell clusters that are similar to pancreatic endocrine islets. The co-staining of cells with antibodies against PDX-1 and C-PEP revealed that almost all of the cells were PDX-1$^+$, while PDX-1$^+$/C-PEP$^+$ cells were mostly found in cells differentiated on MG/dpECM substrates (FIG. 5B).

To determine whether these cell clusters are capable of secreting insulin in response to glucose stimulation, glucose-stimulated insulin secretion (GSIS) analysis was carried out, which showed that either with or without the presence of dpECM, the S4 cells did not show glucose-responsive insulin secretion. However, the intracellular insulin could be purged out when depolarized by KCl solution, suggesting these cells had acquired exocytosis capability (data not shown).

Clearly, these islet-like organoids developed from iPSCs on MG/dpECM coated substrates were immature. The detection of significant number of multi-hormone expressing endocrine cells in these cell clusters suggested that their cell compositions and structure are very similar to fetal islets.

Figure 5A:
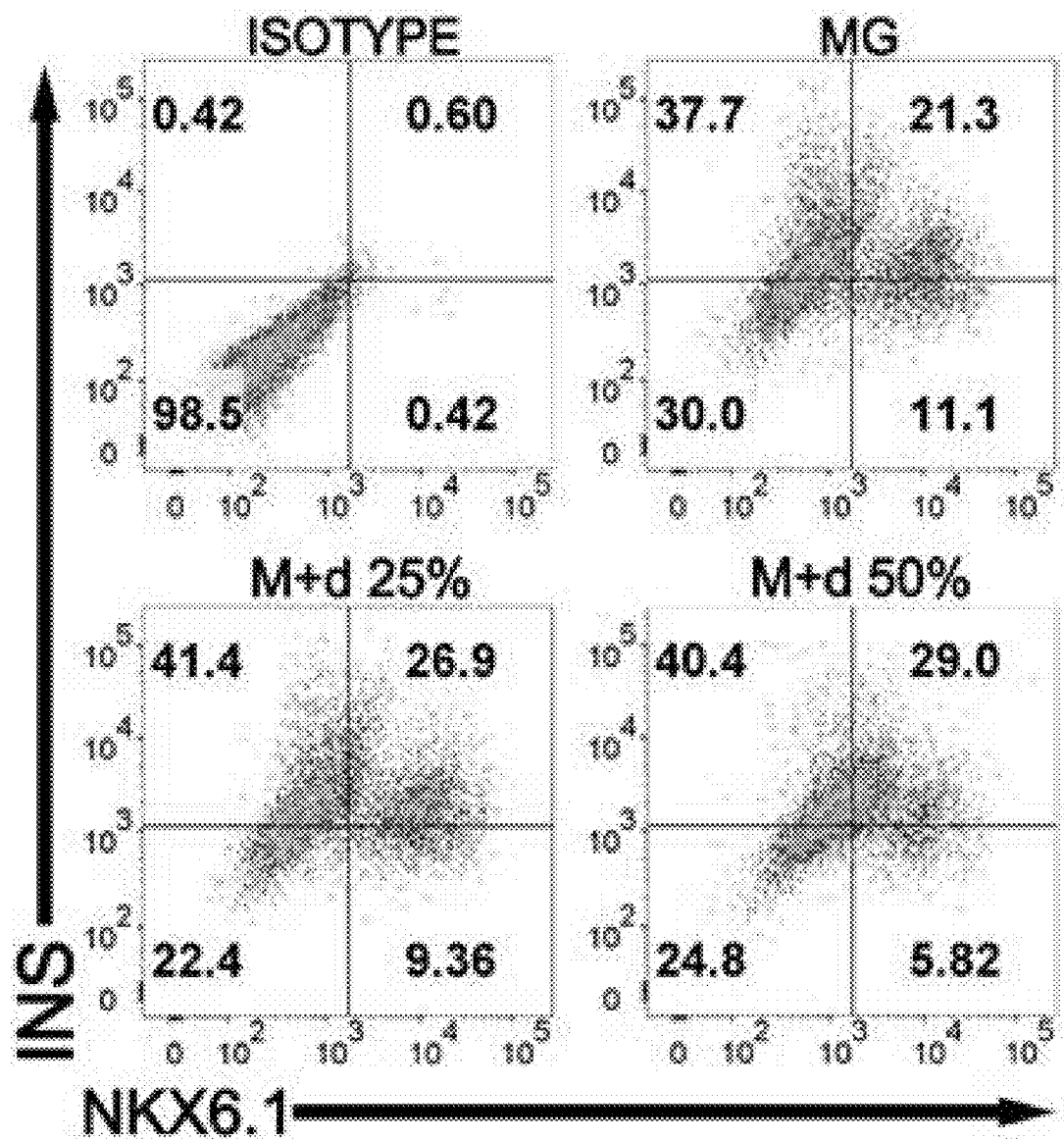
FIGS. 5A-5C show characterization of S4 cells.
Figures 5B, 5C:
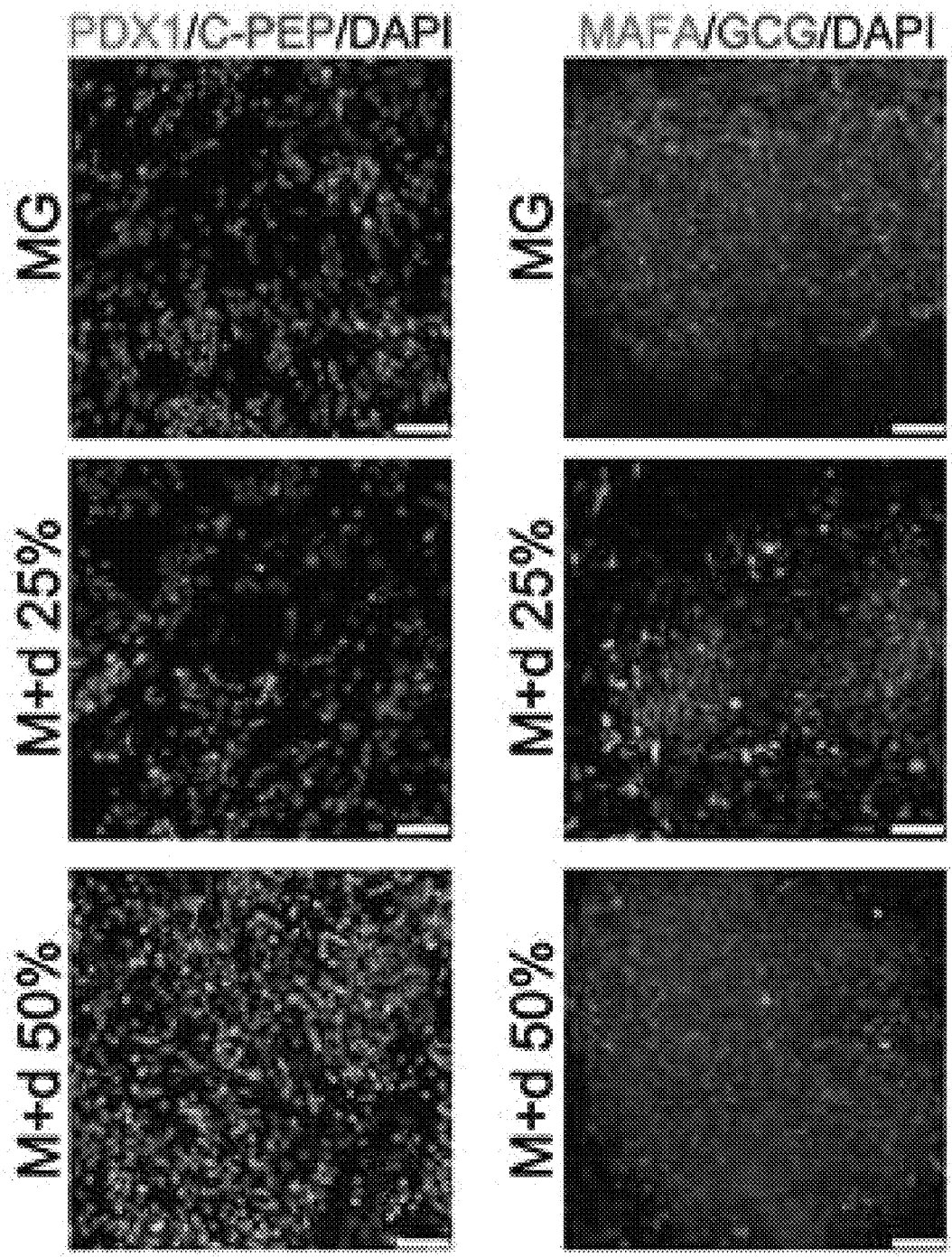
Figure 7A:
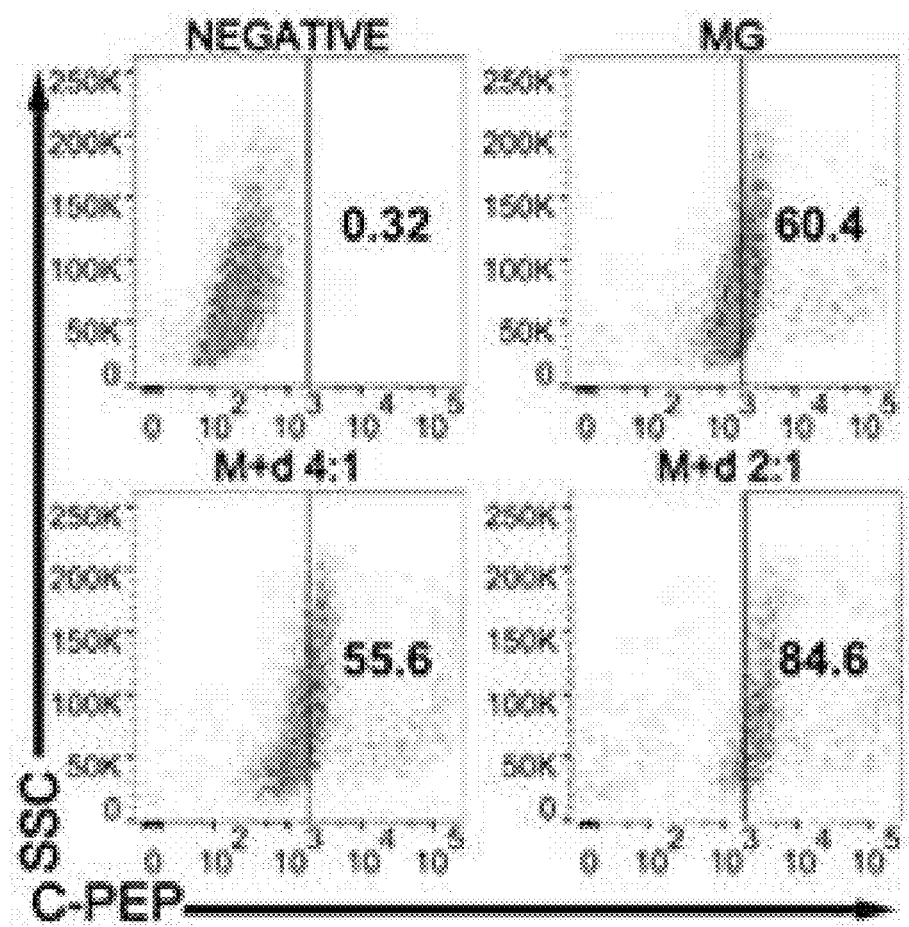
FIG. 7A-7E show representative flow cytometric analysis of cell compositions of islet organoid at Stage 5. Representative flow cytometric analysis of C-PEP (FIG. 7A), GCG (FIG. 7A), SST (FIG. 7C), and PPY (FIG. 7D) expressing cells in S5 aggregates. SSC: side scatter.
Figure 7B:
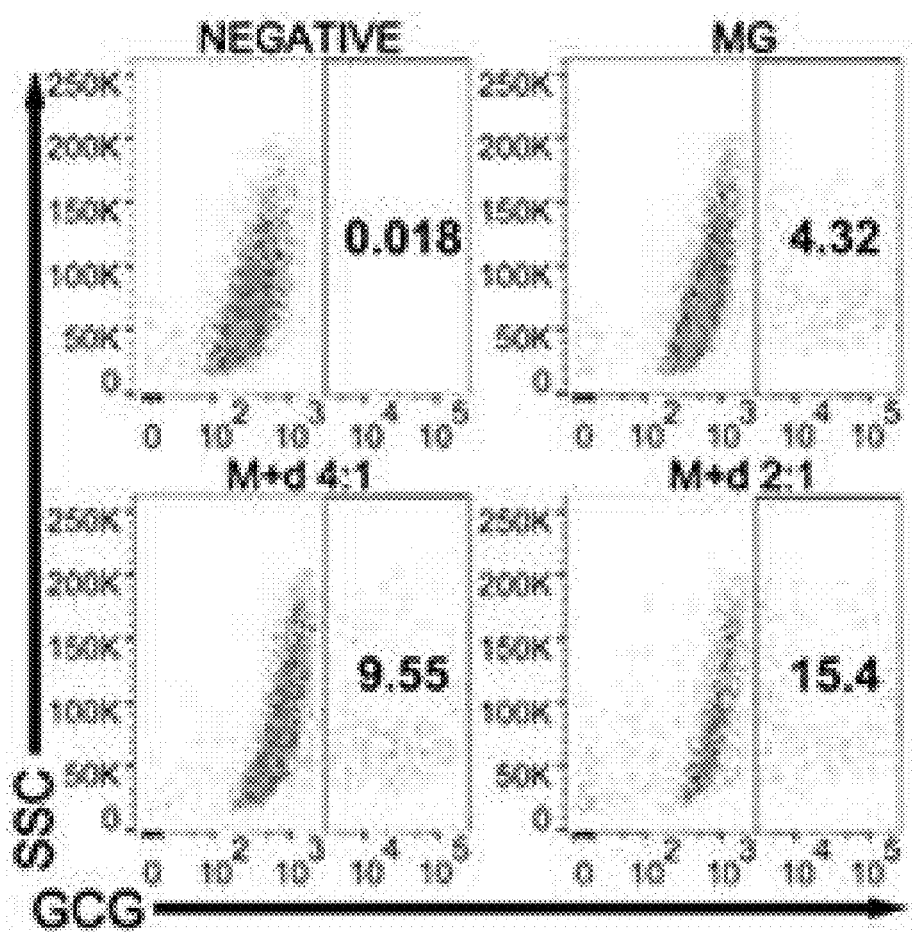
Figure 7C:
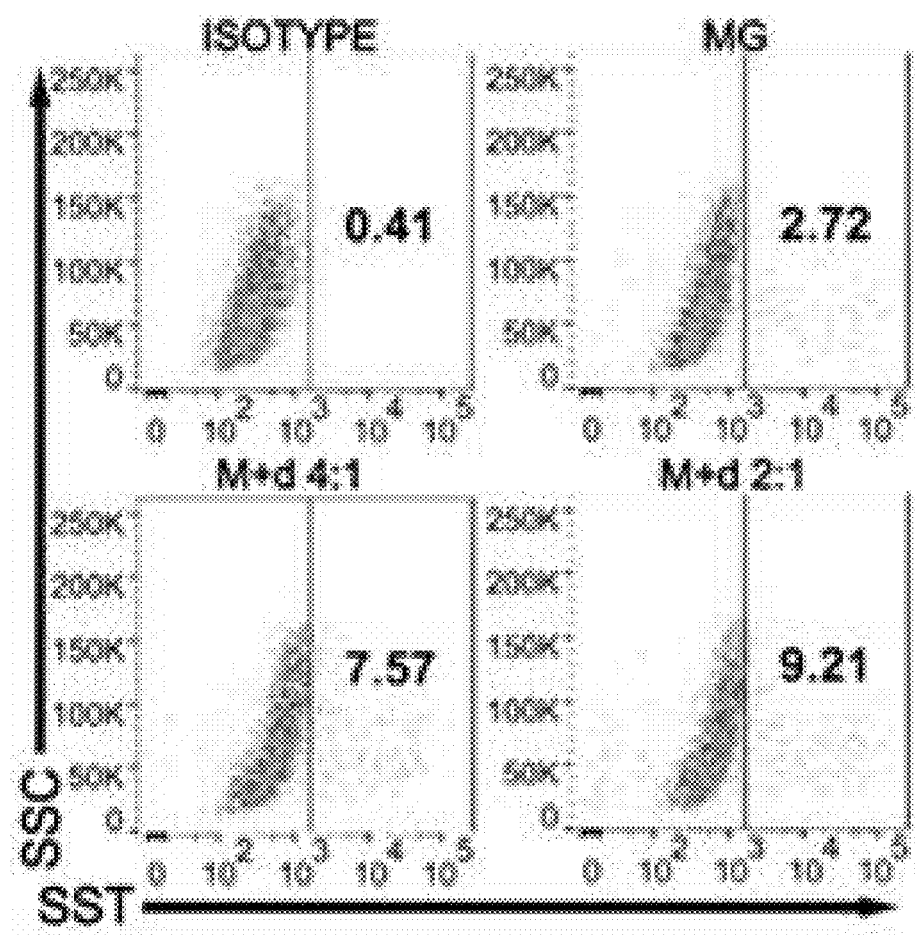
Figure 7D:
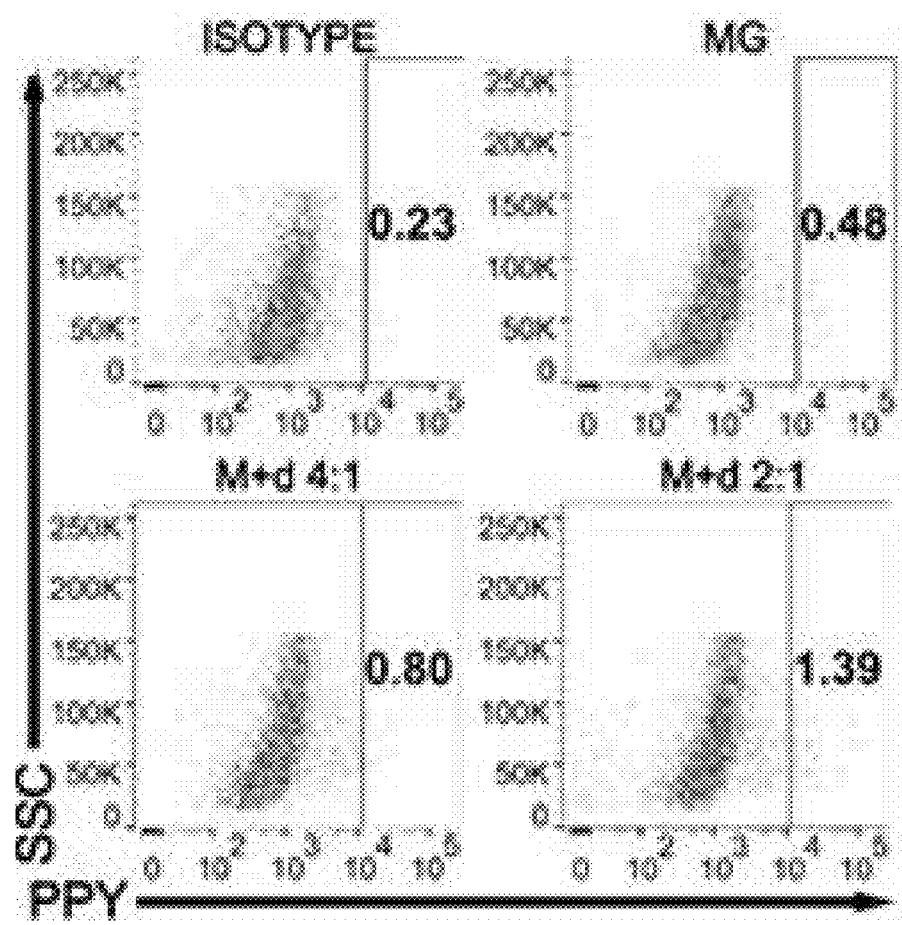
Figure 7E:
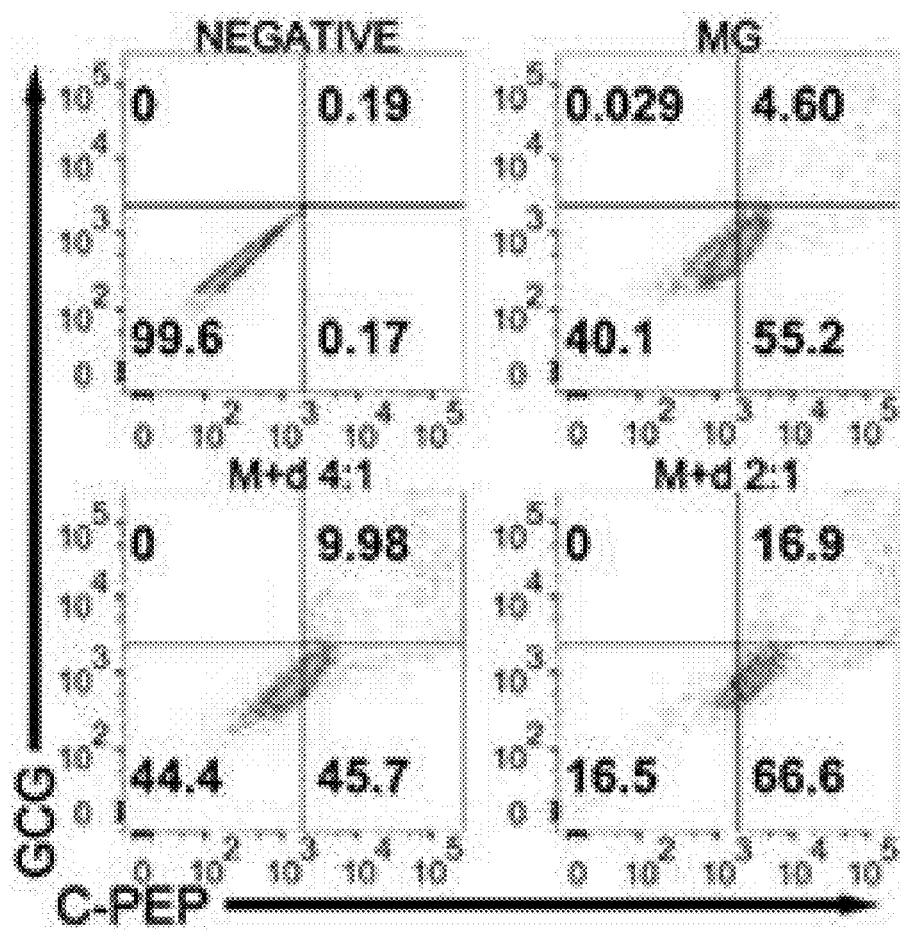

As demonstrated by optical sections through the 3D cultured organoids, the core of the mouse islets was almost exclusively composed of C-PEP$^+$ and GCG$^+$ cells were dispersed throughout the organoids. Flow cytometry revealed that 3D culture further increased C-PEP+ cells (FIG. 7A) with sharp decline of the GCG population (FIG. 7B) as compared to S4 cells (FIGS. 4H and 4I). Cells transferred from 2:1 mixed MG/dpECM substrate produced 9.61±0.56% of SST$^+$ cells (FIG. 7C) and 1.19±0.21% PPY$^+$ cells (FIG. 7D), similar to the populations observed in S4 cells (FIGS. 4E and F) and adult human islets. Moreover, the population of CPEP$^+$/GCG$^+$ polyhormonal cells from 2:1 mixed MG/dpECM substrate decreased significantly in S5 organoids when compared to S4 cells (FIGS. 7E and 4G), indicating further maturation of organoids without losing physiological cellularity of non-β cells at S5. Taken together, these demonstrate for the first time, that dpECM promotes the differentiation and maturation of islet tissue development from both iPSCs and ESCs.

dpECM Facilitates Assembly of Islet Cellularity During hPSC Pancreatic Differentiation FIGS. 5A-5C show characterization of S4 cells. (FIG. 5A) Flow cytometric analysis of insulin (INS) and Nkx6.1 expression in S4 cells. Numbers in quadrants represent the percentage of total counted cells, illustrating the typical population of both NKX6.1+ and insulin+ cells generated at S4. (FIGS. 5B and 5C) Representative immunofluorescent staining of S4 cells cultured on various conditions. (FIG. 5B) pancreatic and duodenal homeobox 1 (PDX-1, green) and C-peptide (C-PEP, red). (FIG. 5C) MAF bZIP transcription factor A (MAFA, green) and glucagon (GCG, red). 4,6-diamidino-2-phenylindole (DAPI, blue) was used for counterstaining nuclei. Bars, 50 μm.

To further characterize the iPSCs-derived organoids and other endocrine cells generated by the unique microenvironment of dpECM, flow cytometry was performed for detecting insulin (INS) and NKX6.1 expression in S4 cells. The results showed that cells cultured on dpECM possessed higher proportion of INS+ cells as well as INS+/NKX6.1+ cells compared to cells cultured on MG− coated substrates (FIG. 5A). This is consistent with the previous finding that dpECM allows generating more C-PEP+/GCG− cells, rather than C-PEP+/GCG+ cells (FIG. 4C). Co-staining of the PDX-1 and C-PEP revealed that almost all of the cells were PDX-1+ under each culture condition, while PDX-1+/C-PEP+ cells were mostly found from cells grown on dpECM-coated niches (FIG. 5B). Furthermore, immunostaining result also confirmed the expression of MAF bZIP transcription factor A (MAFA), a critical functional marker expressed in adult β-cells [Pan F C, Brissova M. Pancreas development in humans. *Curr Opin Endocrinol Diabetes Obes* 21, 77-82 (2014); Kim A, Miller K, Jo J, Kilimnik G, Wojcik P, Hara M. Islet architecture: A comparative study. *Islets* 1, 129-136 (2009).] in S4 cells cultured on dpECM-containing coating condition (FIG. 5C).

Figure 6B:
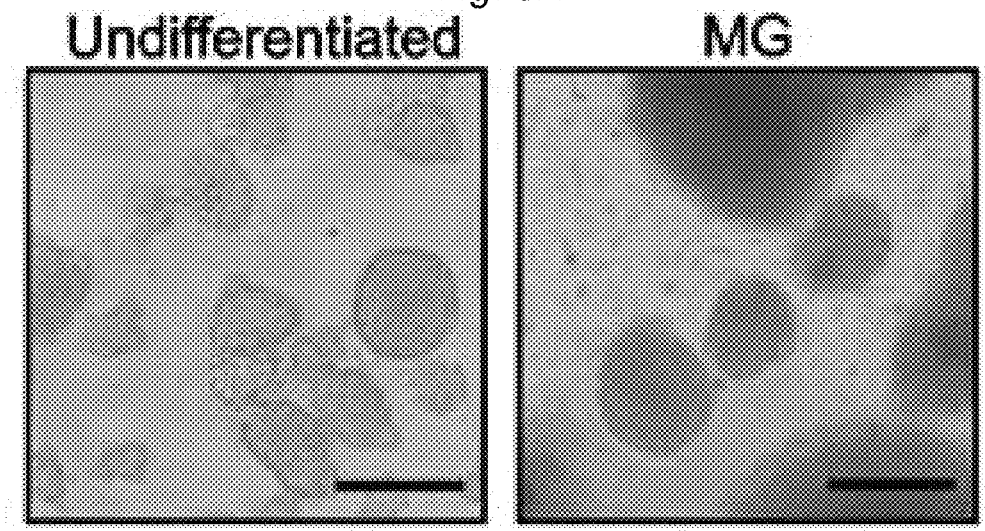
Figure 6B:
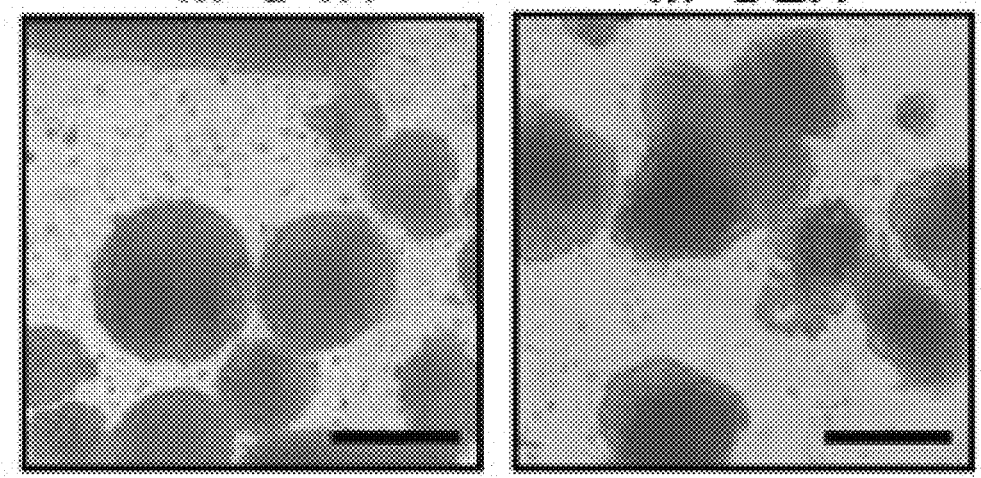

Next, to determine whether the iPSC-derived cells are able to secrete insulin in response to glucose stimulation, glucose-stimulated insulin secretion (GSIS) was carried out analysis. ELISA results unveiled that either with or without the presence of dpECM, the S4 cells did not show glucose-responsiveness. However, the intracellular insulin was purged out when depolarized by KCl solution, suggesting S4 cells had acquired exocytosis capability (data not shown). Notably, there was a dpECM dose-dependent increment in the level of insulin secretion when dpECM was introduced in coating plates, which implicates the promotive role of dpECM in β-cell lineage decision.

dpECM Augments Maturation of Islet Organoids During hPSC Pancreatic Differentiation in 3D Cultures In order to generate functional islet tissues that are glucose responsive insulin-secretion tissues, Stage 5 was introduced into the differentiation protocol based on the strategy reported by other group [Bosco D, et al. Unique arrangement of alpha- and beta-cells in human islets of Langerhans. *Diabetes* 59, 1202-1210 (2010). with slight modifications. 2D culture was compared with suspension-based 3D aggregate culture, the latter was achieved by transferring differentiated cells into ultra-low attachment plates for S4 and S5 differentiation (FIG. 6A). First, the existence of insulin secretion cells in 3D cultured organoids was confirmed by DTZ staining. DTZ selectively chelates zinc in the insulin-containing secretory granules existed in insulin-producing cells [Cabrera O, Berman D M, Kenyon N S, Ricordi C, Berggren P O, Caicedo A. The unique cytoarchitecture of human pancreatic islets has implications for islet cell function. *Proc Natl Acad Sci USA* 103, 2334-2339 (2006).]. Most of the organoids appeared crimson red, while undifferentiated hPSCs were not stained (FIG. 6B).

Figure 6C:
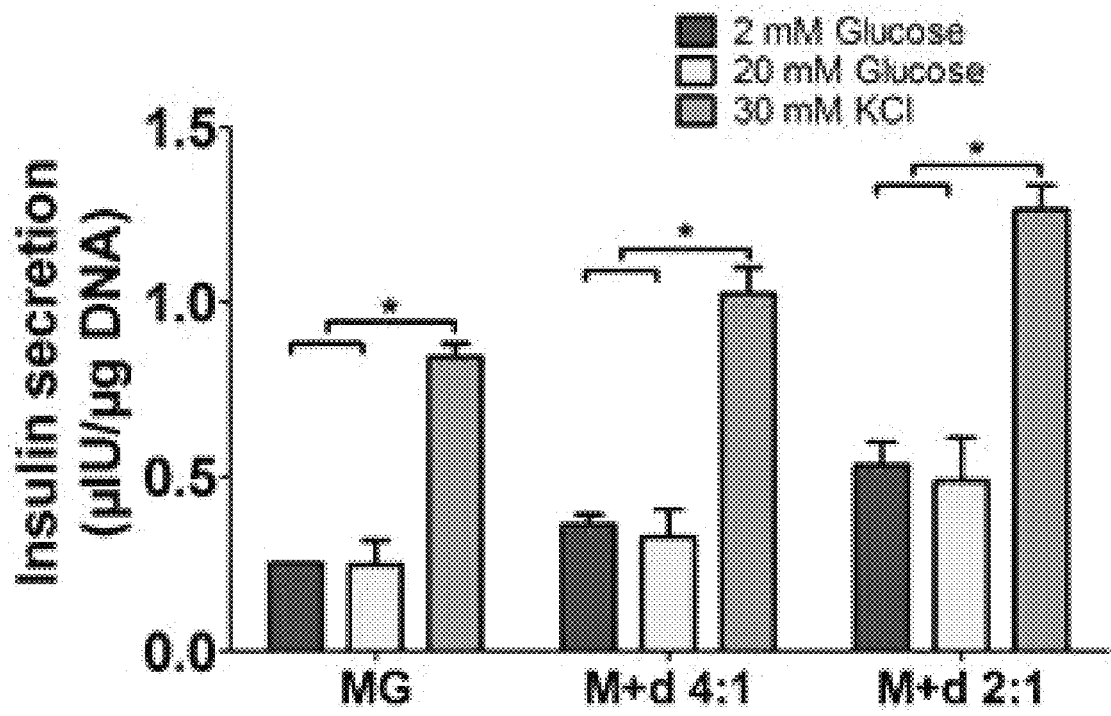
Figure 11:
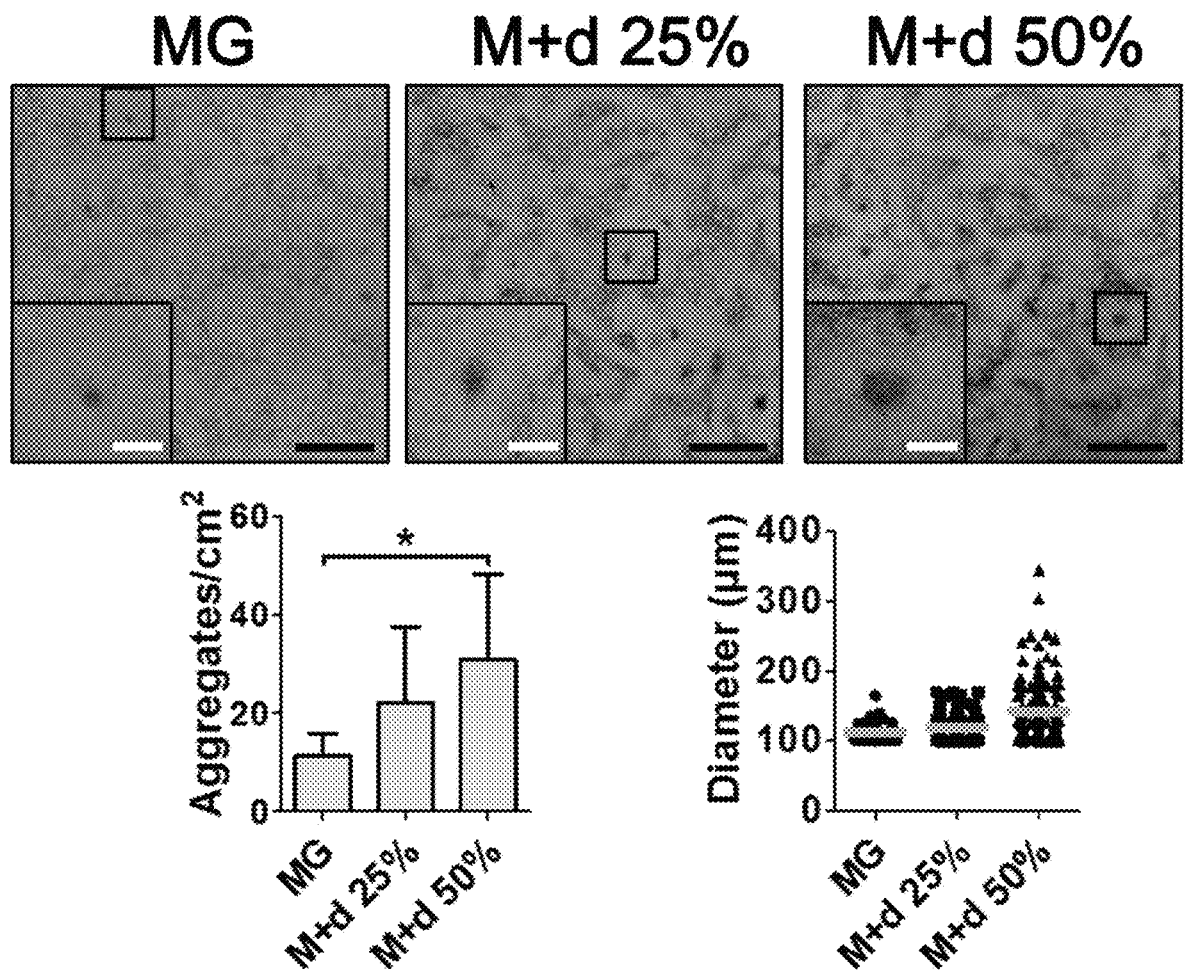
FIG. 11 shows cell clusters observed at day 7 of S5 in 2D cultures. (A) Micrographs of cell clusters formed on MG/dpECM coated plates. Black scale bars, 1,000 µm; white scale bars, 200 µm. Tiled images covering an area of 0.53 cm2 were randomly selected and analyzed by ImageJ software. (B) Number of cell clusters formed on MG/dpECM coated plates. Tiled images covering an area of 0.53 cm2 were randomly selected and analyzed by ImageJ software. Data are shown as mean±SD (n=8). *, p<0.05. (C) Diameters of cell clusters formed on MG/dpECM coated plates. Gray bars indicate average diameter of aggregates.

Further investigation by GSIS assay demonstrated that the S5 cells under 2D culture did not show glucose-responsiveness in either MG or dpECM groups (FIG. 6C), although more organoids were formed from cells cultured on dpECM coating condition (FIG. 11). In sharp contrast, considerable improvement of insulin secretion was found in cell aggregates comparing with 2D cultured cells (FIG. 6D).

Figure 6D:
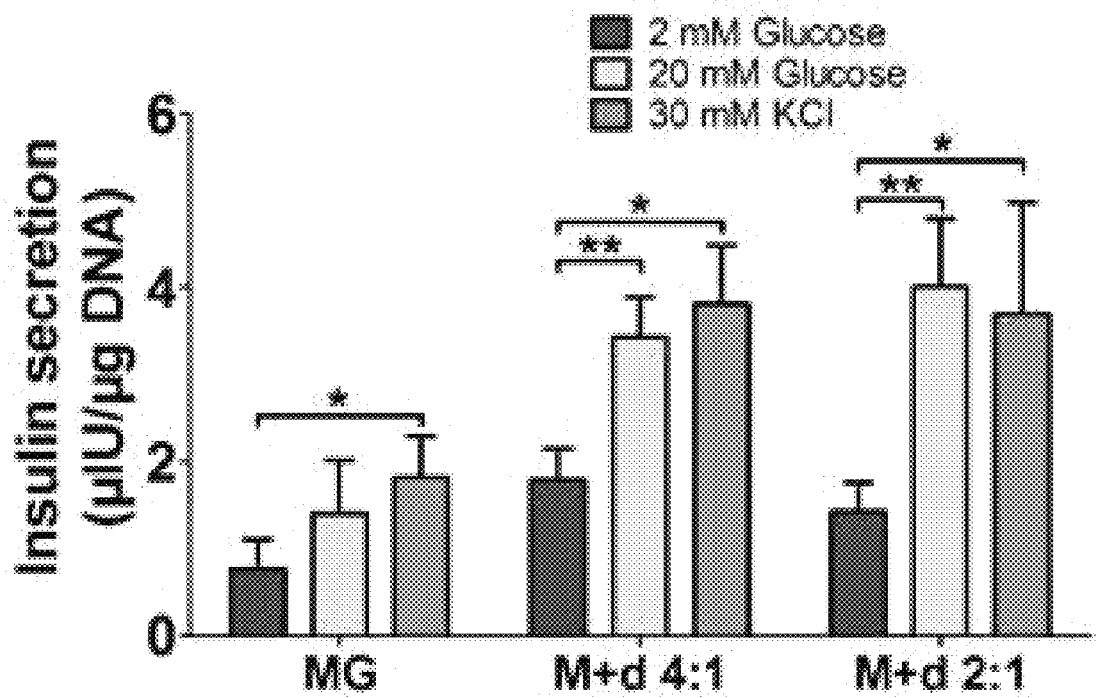

As shown in FIG. 6D, aggregation differentiation condition at S4 and S5 permits insulin secretion correlated with glucose levels at all the substrate coating condition tested. Cells from MG group secreted insulin at low and high concentrations were 0.77±0.34 μIU/μg DNA and 1.40±0.61 μIU/μg DNA, respectively. In addition, with the stimulus of KCl the depolarized cells released 1.81±0.46 μIU/μg DNA. A more remarkable difference was found in cells from two dpECM groups showing 2.02±0.71 (M+d 25%) and 2.90±0.64 (M+d 50%) fold more insulin secreted when respond from low to high glucose concentrations (FIG. 6D). Especially, the overall amount of insulin released from dpECM-treated cells was ~2 times more than that from control group, which further validated previous findings that dpECM enhances insulin expression and maturation (FIG. 2E and FIG. 4C).

Figure 6E:
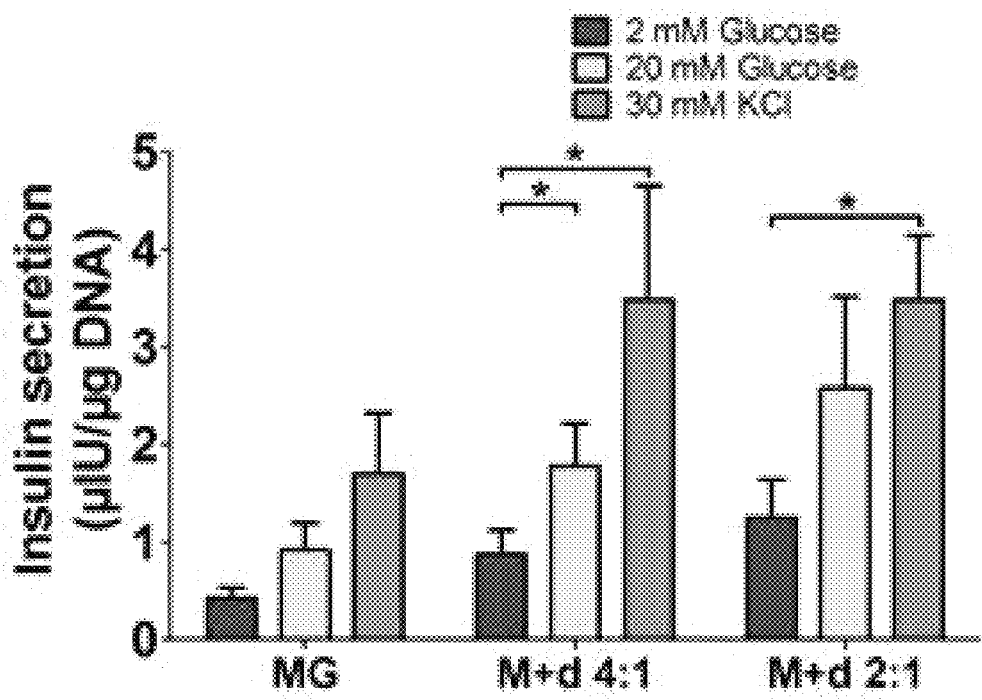
Figure 6F:
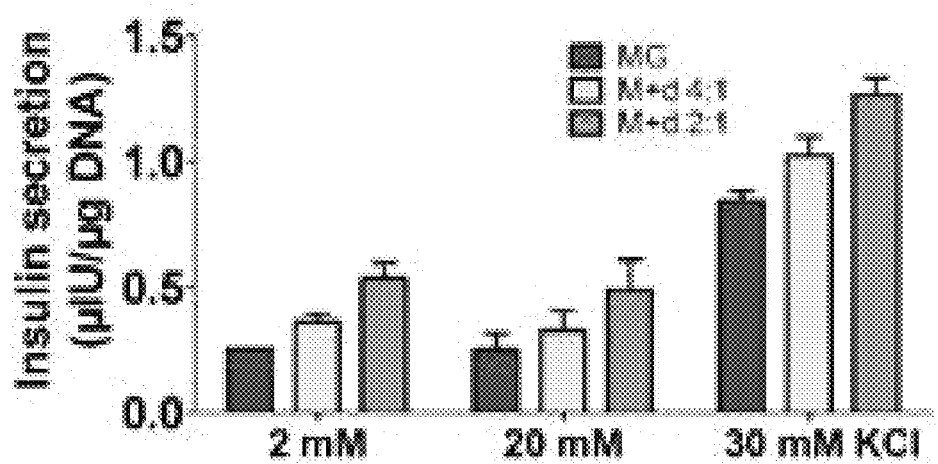
FIGS. 6F-6I. IMR90 and H9 aggregates, 2D vs 3D.
Figure 6G:
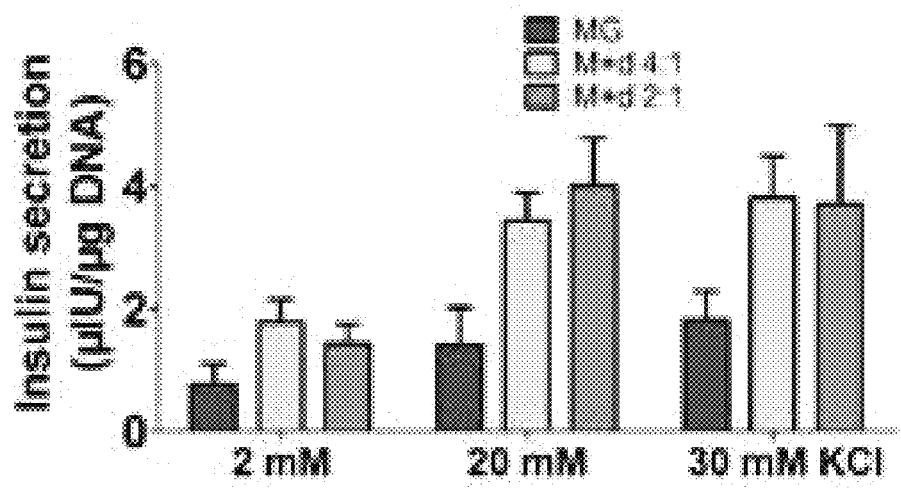
Figure 6H:
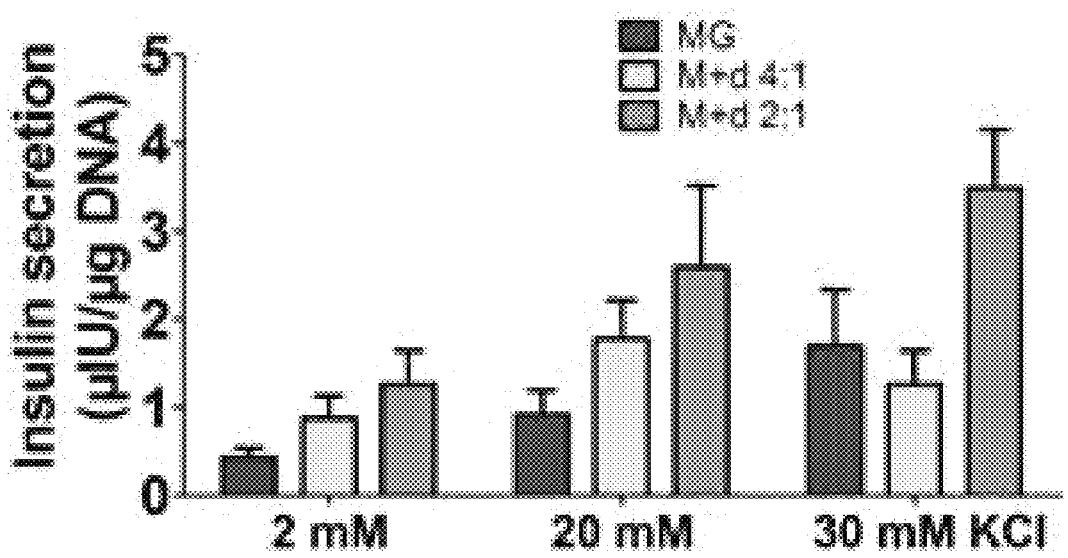
Figure 6I:
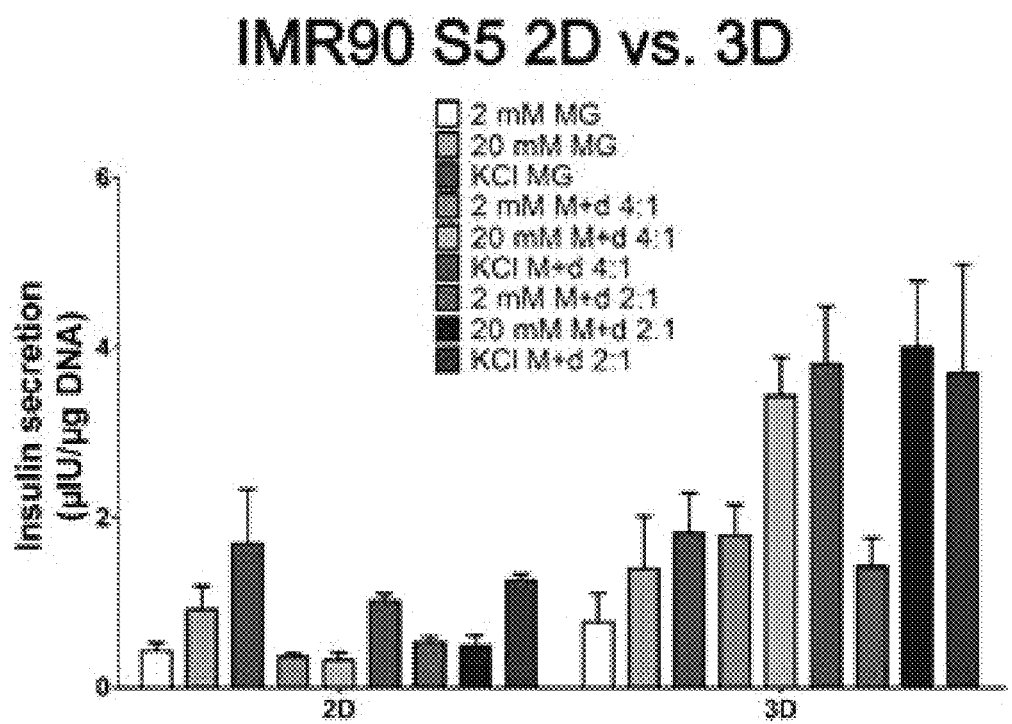

Having characterized the unique role of the dpECM played in human iPSC differentiation towards islet tissue development, the dpECM-coating and differentiation procedures developed in were investigated to see if they are robust to other hPSC lines. hESC line H9 has been widely studied and reported by many research groups including us [Nair G, Hebrok M. Islet formation in mice and men: lessons for the generation of functional insulin-producing beta-cells from human pluripotent stem cells. *Curr Opin Genet Dev* 32, 171-180 (2015); Seymour P A, Sander M. Historical perspective: beginnings of the beta-cell: current perspectives in beta-cell development. *Diabetes* 60, 364-376 (2011); Steiner D J, Kim A, Miller K, Hara M. Pancreatic islet plasticity: interspecies comparison of islet architecture and composition. *Islets* 2, 135-145 (2010)]. Thus, H9 cells were induced into differentiation toward endocrine tissue using the same protocol shown in FIG. 6A. hESC-derived cells at the end of five-stage differentiation also demonstrated sugar level responsive insulin secretion. Likewise, cells after exposed on dpECM-coated environment and differentiated in 3D condition at later stage of differentiation, are able to produce more insulin compared to MG-alone environment (FIG. 6E). Taken together, dpECM promotes the differentiation and maturation of islet tissue development from both human iPSCs and hESCs.

FIGS. 6A-6E show that dpECM promotes insulin secretion in response to glucose level at the end of differentiation in 3D cultures. (FIG. 6A) Schematic outlining differentiation strategy for S5. For S4 and S5, 2D differentiated cells were either continuously differentiated under 2D condition (2D culture) or transferred into an ultra-low attachment plate for aggregate formation (3D culture). (FIG. 6B) DTZ staining of S5 aggregates. Undifferentiated iPSCs cultured in ultra-low attachment plate for 24 hrs were used as a control. (FIGS. 6C and 6D) Higher capacity of insulin secretion from cells grown on dpECM coated substrates during S1-S4 upon glucose challenges. Glucose-stimulated insulin secretion (GSIS) analysis was performed using cells cultured in 2D (FIG. 6C) or 3D (FIG. 6D) at S5 (n=4). Cells were challenged with 2 mM, 20 mM glucose, and 30 mM KCl with 2 mM glucose for 30 min at each step. (FIG. 6E) Insulin secretion from hESCs-derived cells at S5 (n=3). Data are shown as mean±SD. *, p<0.05; **, p<0.01.

Figure 8A:
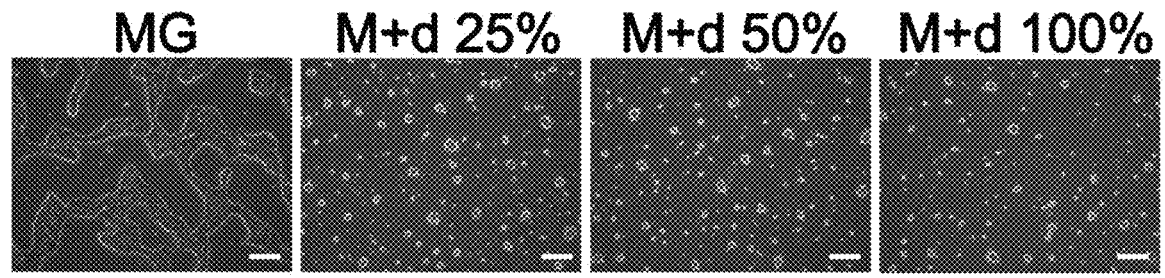
FIG. 8A shows iPSCs (IMR90) cultured on MG- or dpECM-coated substrates. Twenty-four hours after seeding, phase contrast images were captured using a Nikon microscope. Bars, 200 µm.
Figure 8B:
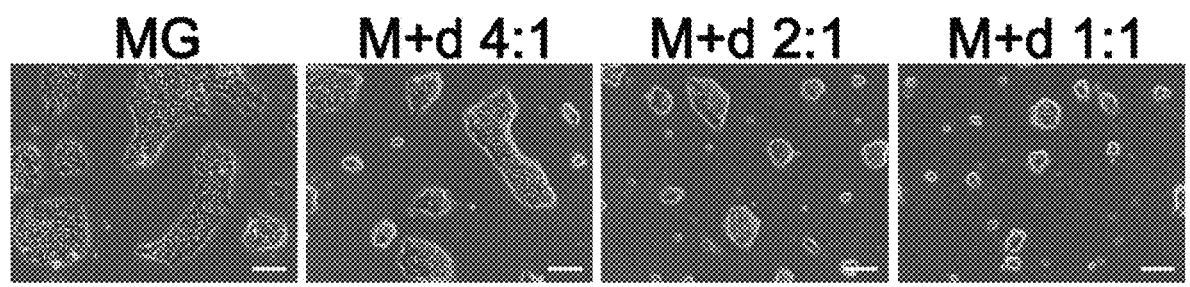
FIG. 8B shows cell clusters formed on MG and MG/dpECM substrates. Phase contrast micrographs taken at 24 h after seeding. Scale bars, 200 µm.

FIG. 8A shows iPSCs (IMR90) cultured on MG- or dpECM-coated substrates. Twenty-four hours after seeding, phase contrast images were captured using a Nikon microscope. Bars, 200 μm.

FIG. 9 shows flow cytometry analysis of SOX17 expression in DE stage. SOX17-positive cells were gated using isotype control (Black square). Red square indicates the percentage of cells expressing high level of SOX17.

FIG. 10 shows TaqMan qPCR analysis of SOX17 and FOXA2 expression in cells at the end of DE stage. Cells cultured on MG-coated (MG) or two-fold increased MG ECM coated substrates (2×MG). Expression levels were normalized to that in cells cultured MG-coated dish. Values are shown as mean±SD (n=3). NS: not statistically significant.

Figure 13A:
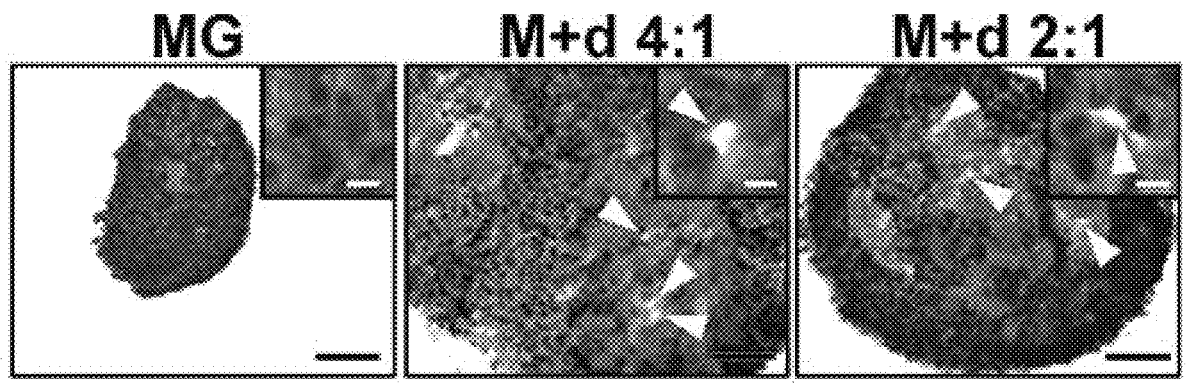
FIGS. 13A-13E show Vasculogenesis of islet organoid at S5.
Figure 13B:
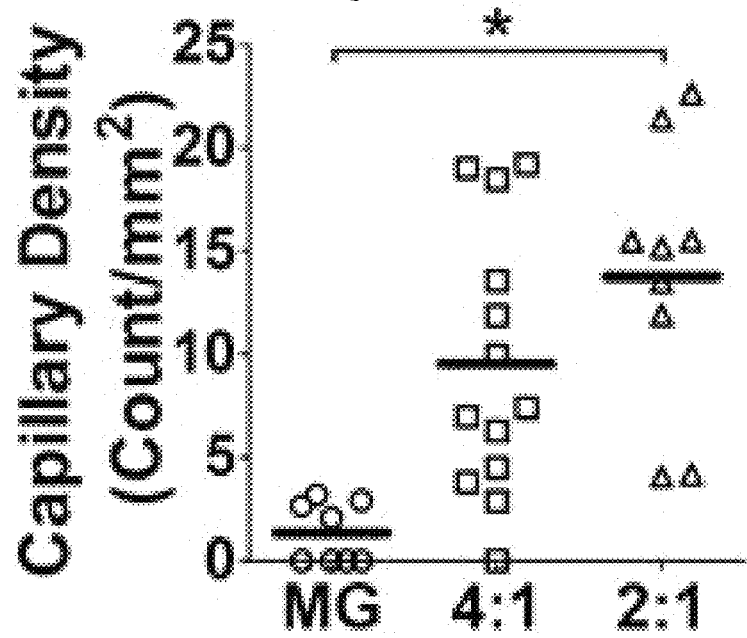
Figure 13C:
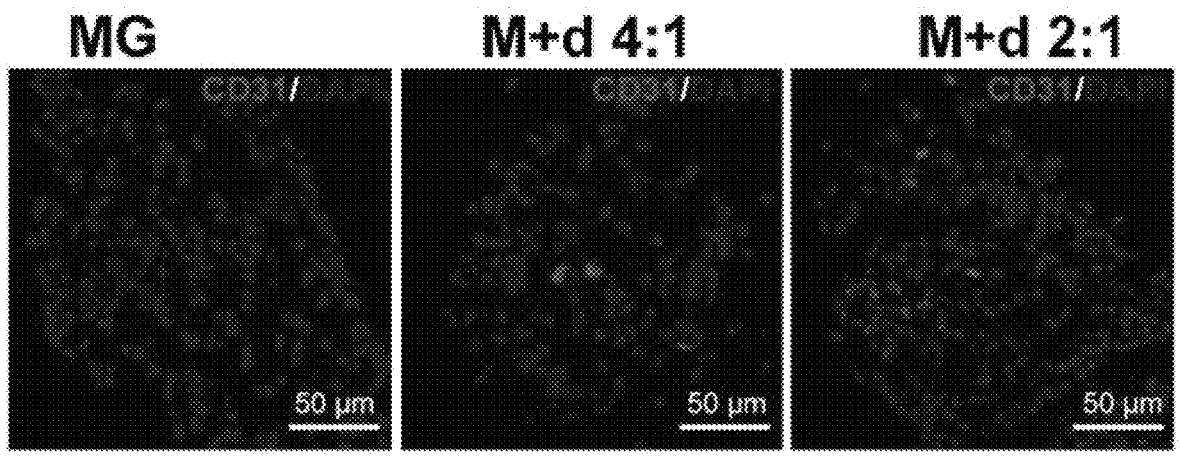
Figure 13D:
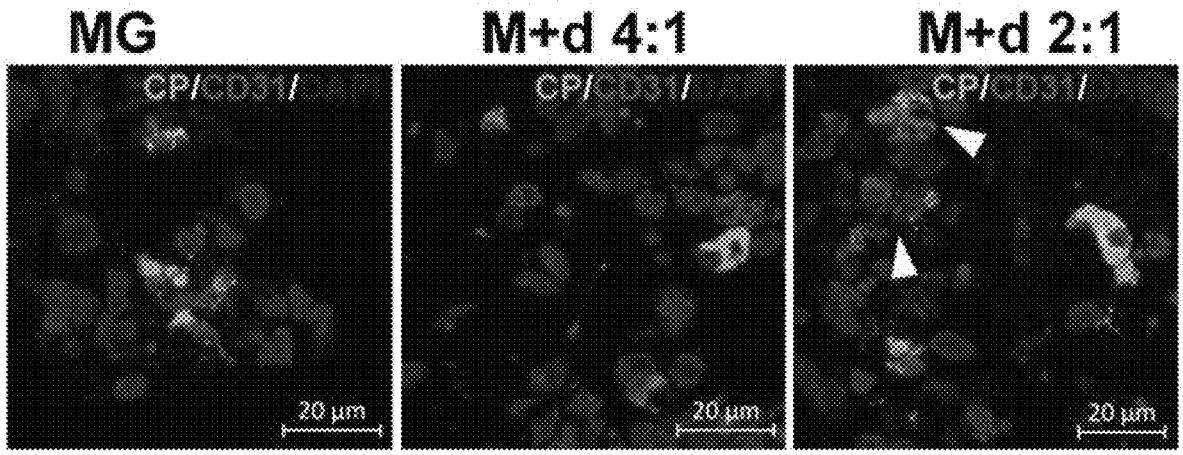
Figure 13E:
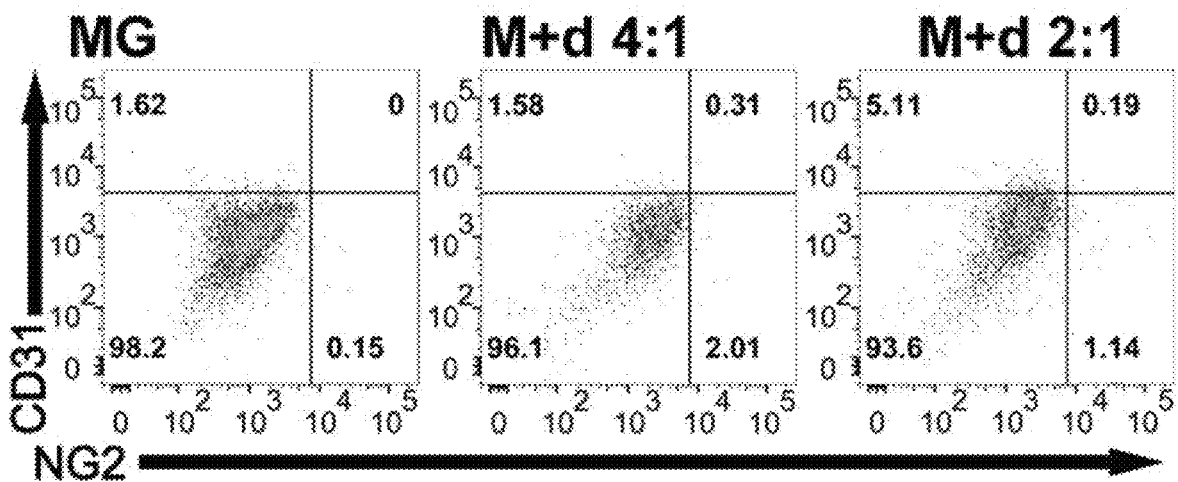

FIG. 11 shows microscopic examination of cellular aggregates at day 7 of S5 under 2D culture. Black bars, 1000 μm; white bars, 200 μm. Tiled images covering an area of 0.53 cm2 were randomly selected and analyzed by ImageJ software. Data are shown as mean±SD (n=8). *, p<0.05.

dpECM Promotes Intra-Organoid Vascularity in the Combination of 2D and 3D Culture The important role of vascularization in differentiation and development of pancreas have been reported recently [Brissova M, Shostak A, Shiota M, Wiebe P O, Poffenberger G, Kantz J, et al. Pancreatic islet production of vascular endothelial growth factor-A is essential for islet vascularization, revascularization, and function. Diabetes 2006, 55(11): 2974-2985; Ballian N, Brunicardi F C. Islet vasculature as a regulator of endocrine pancreas function. World J Surg 2007, 31(4): 705-714.]. During the process to characterize the ILOs generated in this work, lumen structures in dpECM-treated S5 samples were observed. Therefore, the effect of dpECM treatment on vascularization during islet organoid formation was investigated. The intra-organoid vasculature in S5 cells was investigated by H&E staining (FIG. 13A). Many lumens were observed in dpECM treated groups. Morphometric analysis of organoids from M+d 4:1 group showed 7-fold higher capillary density compared to MG group, and the density further increased to 10-fold in M+d 2:1 group (FIG. 13B). Furthermore, there was an increased number of CD31+ endothelial cells (ECs) in dpECM-treated organoids (FIG. 13C). Interestingly, some CD31+ cells located closely to CP+ cells (FIG. 13D, arrowheads), suggesting a physical interaction that is beneficial for the production and secretion of insulin. The flow cytometry results showed that M+d 2:1 group contained 4.43±1.23% of CD31+ cells, which is significantly higher than 1.40±0.09% in MG group (p<0.05) (FIG. 13E). Notably, pericyte marker neuron-glial antigen 2 (NG2) was also detectable in M+d 4:1 and M+d 2:1 treated organoids (2.20±0.16% and 1.42±0.12%, respectively) as compared to an imperceptible population in MG group (0.47±0.43%). These experimental results reveal that dpECM also induces vasculogenesis in addition to islet organogenesis during iPSC islet lineage progression.

While microcirculation is a critical requirement for survival and proper function of transplanted grafts, a successful prevascularization of organoid may reduce posttransplantation-mediated ischemia, thus improve the outcome [Brissova M, Powers AC. Revascularization of transplanted islets: can it be improved? Diabetes 2008, 57(9): 2269-2271]. A significant amount of capillaries formed in dpECM-treated organoids were observed (FIGS. 13A and 13B), which is accordance with the previously reported inductive role of decellularized ECM in vascularization [Moore M C, Pandolfi V, McFetridge P S. Novel human-derived extracellular matrix induces in vitro and in vivo vascularization and inhibits fibrosis. Biomaterials 2015, 49: 37-46; Fercana G R, Yerneni S, Billaud M, Hill J C, VanRyzin P, Richards T D, et al. Perivascular extracellular matrix hydrogels mimic native matrix microarchitecture and promote angiogenesis via basic fibroblast growth factor. Biomaterials 2017, 123: 142-154]. dpECM treatment during hPSC pancreatic differentiation generated not only CD31+ endothelial cells, but also NG2+ pericytes (FIG. 13E), which are involved in supporting EC migration and morphogenesis during the early stages of neovascularization [Fukushi J, Makagiansar I T, Stallcup W B. NG2 proteoglycan promotes endothelial cell motility and angiogenesis via engagement of galectin-3 and alpha3beta1 integrin. Molecular biology of the cell 2004, 15(8): 3580-3590]. Intraislet ECs, apart from their conductive role in angiogenesis, also interact with β-cells and enhance insulin production and secretion [Johansson A, Lau J, Sandberg M, Borg L A, Magnusson P U, Carlsson P O. Endothelial cell signalling supports pancreatic beta cell function in the rat. Diabetologia 2009, 52(11): 2385-2394.] by providing growth factors, basement membrane components, or direct-contact signaling [Penko D, Rojas-Canales D, Mohanasundaram D, Peiris H S, Sun W Y, Drogemuller C J, et al. Endothelial progenitor cells enhance islet engraftment, influence beta-cell function, and modulate islet connexin 36 expression. Cell Transplant 2015, 24(1): 37-48]. In the in vitro generated organoids, our data indicate that dpECM treatment leads to increased number of ECs along with β-cells (FIGS. 13C-13E), which may partially contribute to the improved insulin production and secretory capacity of β-cells in dpECM groups.

Taken together, the capability of dpECM for representing the complex microenvironmental signals that facilitate pancreatic-lineage decision of hPSCs. Utilizing dpECM as an in vitro cell culture substrate, demonstrate an approach for generating islets from hPSCs. dpECM plays an instructive role in cell fate specification in early islet development, which gives rise to vascularized islet-like organoid with multicellular composition.

CONCLUSION

Taken together, the present technology provides an efficient and effective approach to create niches that permit self-assembly of islet organoids during stem cell differentiation. These organoids showed similar cellular composition to native pancreatic islets. The organoids consist of β-cells, α-cells, δ cells, and PP cells. They express islet signature markers insulin, PDX-1, C-peptide, MafA, glucagon, somatostatin, and pancreatic polypeptide. Furthermore, these cells secrete more insulin in response to glucose level compared to a traditional matrix substrate (Matrigel). Remarkably, the dpECM developed in this study facilitates generating more C-peptide+/glucagon− cells rather than C-peptide+/glucagon+ cells. These findings provide the first evidence of a promotive role of the materials developed in recapitulating functional pancreatic islets during induced hPSC differentiation.

The microenvironments that allow self-organization of islet organoids have not been previously elucidated. The technology improves understanding of β-cell maturation and islet organogenesis during hPSC pancreatic differentiation. It also provides an improved system for generating mature islet organoids for islet transplantation and/or for use in drug screening and pathological studies, leading to a cure to diabetes.

Example 2

The feasibility of generating islet-like clusters from mouse embryonic stem cells (mESCs) within a collagen scaffold is demonstrated above. These cell clusters consisted of α, β, and δ cells and exhibited a characteristic mouse islet architecture that has a β cell core surrounded by α and δ cells. The clusters were capable of KATP channel dependent insulin secretion upon glucose challenge. No PP cells were detected in these cell clusters, distinct from adult islets.

Building upon this mESC work, full islet organoids (consisting of four subtypes of pancreatic endocrine cells) from human embryonic stem cells (hESCs) were developed within a biomimetic scaffold. The cytostructural analysis of these organoids revealed a typical architecture of human adult islets, comprising α, β, δ, and PP cells. Both β cells and non-β cells were mixed to form organoids that secrete insulin and C-peptide in response to glucose challenges. The insulin secretory granules were detected in these organoids, indicating the degree of maturation.

When working on human embryonic stem cells (hESCs), collagen scaffolds become weaker and partially collapse after 10-15 days of differentiation. Efforts to overcome this issue included mixing collagen with Matrigel during scaffolding. The incorporation of Matrigel in biomimetic collagen scaffolds improved not only mechanical strength, but also hESC definitive endoderm (DE) differentiation, as indicated by elevated expression of DE markers such as Sox17, Foxa2, and CXCR4.

The mechanical strength of collagen scaffolds was also enhanced by treating or mixing collagen with other chemicals such as polyethylene (glycol) diacrylate (PEGDA) to enhance their mechanical properties during crosslinking. By selecting different molecular weight and adjusting the ratio of PEGDA during treatment, the stiffness of the collagen scaffolds may be adjusted to be close to that of human pancreas.

Figure 12A:
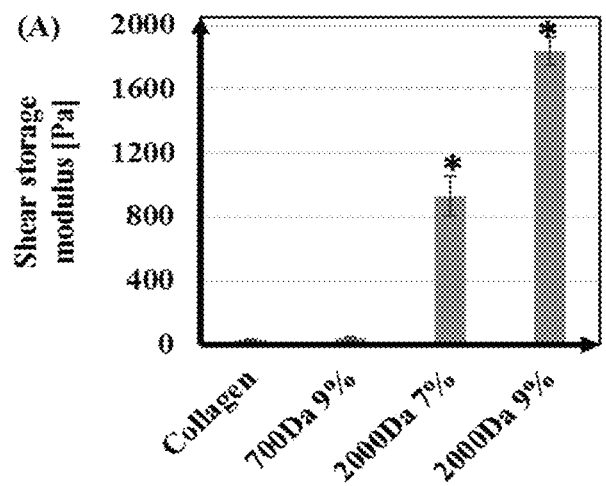
FIGS. 12A-12C show fine tuning of mechanical properties of collagen scaffolds by treating with different molecular weights of PEGDA. The shear storage modulus (FIG. 12A), the shear loss modulus (FIG. 12BB), and the Young's modulus (FIG. 12CC) of the PEGDA treated collagen scaffolds were determined using a rheometer. All experiments were performed in triplicate. Error bars indicate standard deviation. *, p<0.02.
Figure 12B:
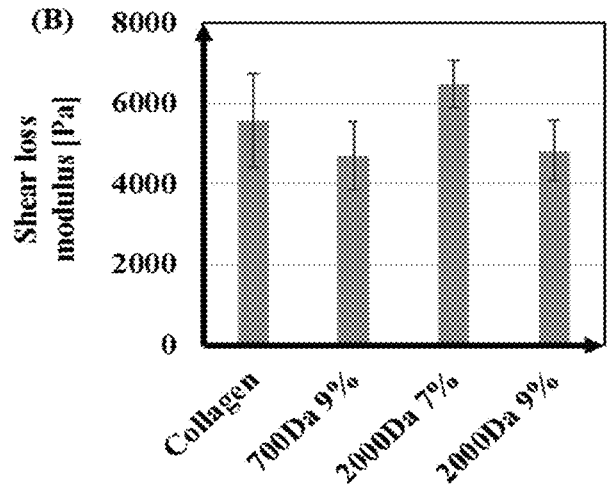
Figure 12C:
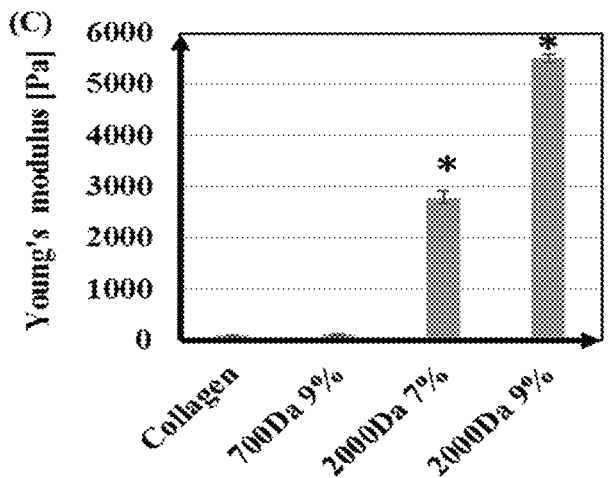

These scaffolds are believed to be superior for islet development due to their improved mechanical properties. The collagen scaffolds are penetrated with-PEGDA to enhance the stiffness and mechanical stability of the scaffolds for islet organoid developed from iPSCs. PEGDA is a polymer approved by FDA for various clinical applications. The stiffness of the collagen scaffolds is finely tuned by treating with different molecular weights of PEGDA, as demonstrated in FIGS. 12A-12C, which shows fine tuning of mechanical properties of collagen scaffolds by treating with different molecular weights of PEGDA. The shear storage modulus (FIG. 12A), the shear loss modulus (FIG. 12B), and the Young's modulus (FIG. 12C) of the PEGDA treated collagen scaffolds were determined using a rheometer. All experiments were performed in triplicate. Error bars indicate standard deviation. *, p<0.02.

A stiffness of 7% 2 kDa PEGDA treated collagen scaffolds is 2.79 kPa, whereas the stiffness of human pancreases is in a range from 1.15 to 2.09 kPa[71]. Accordingly, these scaffolds offer better mechanical cues needed for islet development from iPSCs.

To treat the collagen scaffolds with PEGDA, the cell-laden scaffolds prepared as described above were immersed in a 7% 2 KDa PEGDA solution in the presence of a photoinitiator 2-Hydroxy-4'-(2-hydroxyethoxy)-2-methyl-propiophenone (Sigma-Aldrich) at 0.3 or 0.15 w/v % for 45 min, followed by incubating in a 5% CO2 incubator at 37° C. for 24 hr. The scaffolds are rinsed with PBS twice and placed in a culture medium under a long wavelength UV lamp (6 Watt, 365 nm) for 6 min to crosslink collagen-PEGDA networks. After crosslinking, the scaffolds are ready for islet development as described above.

While it has been reported that a low-intensity long wavelength UV and a relatively short exposure time (365 nm, between 2~20 min) does not alter gene expression profiles of human MSCs, its effect on iPSCs remains unknown. Accordingly, other photoinitiators and light sources for crosslinking may be used, for example eosin Y photosensitizer enables PEGDA crosslinking under a visible light, which is more biocompatible to stem cells. Several iPSC lines including IMR90 and DF4 (WiCell) may be used.

REFERENCES

Each of which is expressly incorporated herein by reference in its entirety:

Agmon, Gillie, and Karen L. Christman. "Controlling stem cell behavior with decellularized extracellular matrix scaffolds." Current Opinion in Solid State and Materials Science 20, no. 4:193-201 (2016).

Alfonso, Andrea L., Jung Lee, E. Alice, M. S. Hitscherich, and M. S. Ma. "Decellularized Pancreatic Tissue." Journal of Health Disparities Research and Practice 9, no. 5:60 (2016).

An D, Ji Y, Chiu A, Lu Y C, Song W, Zhai L, Qi L, Luo D and Ma M. Developing robust, hydrogel-based, nanofiber-enabled encapsulation devices (NEEDs) for cell therapies. Biomaterials; 37:40-8 (2015).

Badylak, Stephen F., Doris Taylor, and Korkut Uygun. "Whole-organ tissue engineering: decellularization and recellularization of three-dimensional matrix scaffolds." Annual review of biomedical engineering 13:27-53 (2011).

Bahney C S, Lujan T J, Hsu C W, Bottlang M, West J L and Johnstone B. Visible light photoinitiation of mesenchymal stem cell-laden bioresponsive hydrogels. Eur Cell Mater.; 22:43-55 (2011).

Ballian N, Brunicardi F C. Islet vasculature as a regulator of endocrine pancreas function. *World J Surg* 2007, 31(4): 705-714.

Barabaschi G D, Manoharan V, Li Q and Bertassoni L E. Engineering Pre-vascularized Scaffolds for Bone Regeneration. Adv Exp Med Biol.; 881:79-94 (2015).

Basford C L, et al. The functional and molecular characterisation of human embryonic stem cell-derived insulin-positive cells compared with adult pancreatic beta cells. *Diabetologia* 55, 358-371 (2012).

Benninger R K, Piston D W. Cellular communication and heterogeneity in pancreatic islet insulin secretion dynamics. *Trends Endocrinol Metab* 25, 399-406 (2014).

Bersini S and Moretti M. 3D functional and perfusable microvascular networks for organotypic microfluidic models. J Mater Sci Mater Med.; 26:180 (2015).

Bhatia S N, Ingber D E. Microfluidic organs-on-chips. *Nat Biotechnol* 32, 760-772 (2014).

Bi H, Ming L, Cheng R, Luo H, Zhang Y, Jin Y. Liver extracellular matrix promotes BM-MSCs hepatic differentiation and reversal of liver fibrosis through activation of integrin pathway. *J Tissue Eng Regen Med* 2016.

Bi H, Ye K and Jin S (2016). Engineering tissue substrates for generation of islet-like organoids from human pluripotent stem cell differentiation. Front. Bioeng. Biotechnol. Conference Abstract: 10th World Biomaterials Congress, Montréal, Canada, 17 May-22 May 2016. doi: 10.3389/conf.FBIOE.2016.01.02293 (Published Online: 30 Mar. 2016). www.frontiersin.org/10.3389/conf.F-BIOE.2016.01.02293/2893/10th_World_Biomaterials_Cong ress/all_events/event_abstract.

Bogorad M I and Searson P C. Real-time imaging and quantitative analysis of doxorubicin transport in a perfusable microvessel platform. Integr Biol (Camb).; 8:976-84 (2016).

Bogorad M I, DeStefano J, Karlsson J, Wong A D, Gerecht S and Searson P C. Review: in vitro microvessel models. Lab Chip; 15:4242-55 (2015).

Bosco D, et al. Unique arrangement of alpha- and beta-cells in human islets of Langerhans. *Diabetes* 59, 1202-1210 (2010).

Brereton H C, et al. Homotypic cell contact enhances insulin but not glucagon secretion. *Biochem Bioph Res Co* 344, 995-1000 (2006).

Brissova M and Powers A C. Revascularization of transplanted islets: can it be improved? Diabetes; 57:2269-71 (2008).

Brissova M, Aamodt K, Brahmachary P, Prasad N, Hong J Y, Dai C, Mellati M, Shostak A, Poffenberger G, Aramandla R, Levy S E and Powers A C. Islet microenvironment, modulated by vascular endothelial growth factor-A signaling, promotes beta cell regeneration. Cell Metab.; 19:498-511 (2014).

Brissova M, Shostak A, Fligner C L, Revetta F L, Washington M K, Powers A C and Hull R L. Human Islets Have Fewer Blood Vessels than Mouse Islets and the Density of Islet Vascular Structures Is Increased in Type 2 Diabetes. J Histochem Cytochem.; 63:637-45 (2015).

Brissova M, Shostak A, Shiota M, Wiebe P O, Poffenberger G, Kantz J, Chen Z, Carr C, Jerome W G, Chen J, Baldwin H S, Nicholson W, Bader D M, Jetton T, Gannon M and Powers A C. Pancreatic islet production of vascular endothelial growth factor—a is essential for islet vascularization, revascularization, and function. Diabetes; 55:2974-85 (2006).

Brissova, M., M. J. Fowler, W. E. Nicholson, A. Chu, B. Hirshberg, D. M. Harlan, A. C. Powers, Assessment of human pancreatic islet architecture and composition by laser scanning confocal microscopy, J Histochem Cytochem 53(9):1087-97 (2005).

Broutier L, et al. Culture and establishment of self-renewing human and mouse adult liver and pancreas 3D organoids and their genetic manipulation. *Nature protocols* 11, 1724-1743 (2016).

Bruin J E, et al. Characterization of polyhormonal insulin-producing cells derived in vitro from human embryonic stem cells. *Stem cell research* 12, 194-208 (2014).

Bruin J E, Rezania A, Xu J, Narayan K, Fox J K, O'Neil J J and Kieffer T J. Maturation and function of human embryonic stem cell-derived pancreatic progenitors in macroencapsulation devices following transplant into mice. Diabetologia; 56:1987-98 (2013).

Cabrera O, Berman D M, Kenyon N S, Ricordi C, Berggren P O, Caicedo A. The unique cytoarchitecture of human pancreatic islets has implications for islet cell function. *Proc Natl Acad Sci USA* 103, 2334-2339 (2006).

Carvalho C P, Barbosa H C, Britan A, Santos-Silva J C, Boschero A C, Meda P and Collares-Buzato C B. Beta cell coupling and connexin expression change during the functional maturation of rat pancreatic islets. Diabetologia; 53:1428-37 (2010).

Chao K C, Chao K F, Fu Y S, Liu S H. Islet-like clusters derived from mesenchymal stem cells in Wharton's Jelly of the human umbilical cord for transplantation to control type 1 diabetes. *PLoS One* 3, e1451 (2008).

Chen S, Borowiak M, Fox J L, Maehr R, Osafune K, Davidow L, Lam K, Peng L F, Schreiber S L, Rubin L L and Melton D. A small molecule that directs differentiation of human ESCs into the pancreatic lineage. Nat Chem Biol.; 5:258-65 (2009).

Chen, Wenhui, Yasuhiko Tabata, and Yen Wah Tong. "Fabricating tissue engineering scaffolds for simultaneous cell growth and drug delivery." Current pharmaceutical design 16, no. 21:2388-2394 (2010).

Cheng, Jennifer Y C, Michael Raghunath, John Whitelock, and Laura Poole-Warren. "Matrix components and scaffolds for sustained islet function." Tissue Engineering Part B: Reviews 17, no. 4:235-247 (2011).

Coronel, Maria M., and Cherie L. Stabler. "Engineering a local microenvironment for pancreatic islet replacement." Current opinion in biotechnology 24, no. 5:900-908 (2013).

Crapo, Peter M., Thomas W. Gilbert, and Stephen F. Badylak. "An overview of tissue and whole organ decellularization processes." Biomaterials 32, no. 12:3233-3243 (2011).

Cross V L, Zheng Y, Won Choi N, Verbridge S S, Sutermaster B A, Bonassar U, Fischbach C and Stroock A D. Dense type I collagen matrices that support cellular remodeling and microfabrication for studies of tumor angiogenesis and vasculogenesis in vitro. Biomaterials; 31:8596-607 (2010).

D'Amour K A, Agulnick A D, Eliazer S, Kelly O G, Kroon E and Baetge E E. Efficient differentiation of human embryonic stem cells to definitive endoderm. Nat Biotechnol.; 23:1534-41 (2005).

D'Amour K A, Bang A G, Eliazer S, Kelly O G, Agulnick A D, Smart N G, Moorman M A, Kroon E, Carpenter M K and Baetge E E. Production of pancreatic hormone-expressing endocrine cells from human embryonic stem cells. Nat Biotechnol.; 24:1392-401 (2006).

Davis, Nicolynn E., Liese N. Beenken-Rothkopf, Annie Mirsoian, Nikola Kojic, David L. Kaplan, Annelise E. Barron, and Magali J. Fontaine. "Enhanced function of pancreatic islets co-encapsulated with ECM proteins and mesenchymal stromal cells in a silk hydrogel." Biomaterials 33, no. 28:6691-6697 (2012).

De Carlo, E., S. Baiguera, M. T. Conconi, S. Vigolo, C. Grandi, S. Lora, C. Martini et al. "Pancreatic acellular matrix supports islet survival and function in a synthetic tubular device: in vitro and in vivo studies." International journal of molecular medicine 25, no. 2:195-202 (2010).

El-Gohary Y, Sims-Lucas S, Lath N, Tulachan S, Guo P, Xiao X, Welsh C, Paredes J, Wiersch J, Prasadan K, Shiota C and Gittes G K. Three-dimensional analysis of the islet vasculature. Anat Rec (Hoboken).; 295:1473-81 (2012).

Faulk D M, et al. The effect of detergents on the basement membrane complex of a biologic scaffold material. *Acta Biomater* 10, 183-193 (2014).

Forster N A, Penington A J, Hardikar A A, Palmer J A, Hussey A, Tai J, Morrison W A and Feeney S J. A prevascularized tissue engineering chamber supports growth and function of islets and progenitor cells in diabetic mice. Islets; 3:271-83 (2011).

Fotino N, Fotino C, Pileggi A. Re-engineering islet cell transplantation. *Pharmacol Res* 98, 76-85 (2015).

Fu J, Wiraja C, Muhammad H B, Xu C and Wang D A. Improvement of endothelial progenitor outgrowth cell (EPOC)-mediated vascularization in gelatin-based hydrogels through pore size manipulation. Acta Biomater. (2017).

Fu, Ru-Huei, Yu-Chi Wang, Shih-Ping Liu, Ton-Ru Shih, Hsin-Lien Lin, Yue-Mi Chen, Jiun-Huei Sung et al. "Decellularization and recellularization technologies in tissue engineering." Cell transplantation 23, no. 4-5:621-630 (2014).

Gibot L, Galbraith T, Bourland J, Rogic A, Skobe M and Auger F A. Tissue-engineered 3D human lymphatic microvascular network for in vitro studies of lymphangiogenesis. Nat Protoc.; 12:1077-1088 (2017).

Goh S K, et al. Perfusion-decellularized pancreas as a natural 3D scaffold for pancreatic tissue and whole organ engineering. *Biomaterials* 34, 6760-6772 (2013).

Goh, Saik Kia. "Bio-engineered pancreas with human embryonic stem cells and whole organ derived extracellular matrix scaffolds." PhD diss., University of Pittsburgh (2015).

Graham M L, Janecek J L, Kittredge J A, Hering B J and Schuurman H J. The streptozotocin-induced diabetic nude mouse model: differences between animals from different sources. Comp Med.; 61:356-60 (2011).

Greggio C, De Franceschi F, Grapin-Botton A. Concise reviews: In vitro-produced pancreas organogenesis models in three dimensions: self-organization from few stem cells or progenitors. *Stem Cells* 33, 8-14 (2015).

Greggio C, et al. Artificial three-dimensional niches deconstruct pancreas development in vitro. *Development* 140, 4452-4462 (2013).

Halban P A. Cellular sources of new pancreatic beta cells and therapeutic implications for regenerative medicine. *Nat Cell Biol* 6, 1021-1025 (2004).

Haque M A, Nagaoka M, Hexig B, Akaike T. Artificial extracellular matrix for embryonic stem cell cultures: a new frontier of nanobiomaterials. *Science and technology of advanced materials* 11, 014106 (2010).

Hoshiba, Takashi, Guoping Chen, Chiho Endo, Hiroka Maruyama, Miyuki Wakui, Eri Nemoto, Naoki Kawazoe, and Masaru Tanaka. "Decellularized extracellular matrix as an in vitro model to study the comprehensive roles of the ECM in stem cell differentiation." Stem cells international 2016 (2015).

Hrvatin S, et al. Differentiated human stem cells resemble fetal, not adult, beta cells. *Proc Natl Acad Sci USA* 111, 3038-3043 (2014).

Hughes C S, Postovit L M, Lajoie G A. Matrigel: a complex protein mixture required for optimal growth of cell culture. *Proteomics* 10, 1886-1890 (2010).

Hunter C S and Stein R W. Evidence for Loss in Identity, De-Differentiation, and Trans-Differentiation of Islet beta-Cells in Type 2 Diabetes. Front Genet.; 8:35 (2017).

Hunter J D, Cannon J A. Biomaterials: So Many Choices, So Little Time. What Are the Differences? *Clin Colon Rect Surg* 27, 134-139 (2014).

Ichii, H, L. Inverardi, A. Pileggi, R. D. Molano, O. Cabrera, A. Caicedo, S. Messinger, Y. Kuroda, P. O. Berggren, C. Ricordi, A novel method for the assessment of cellular composition and beta-cell viability in human islet preparations, Am J Transplant 5(7):1635-45 (2005).

Ionescu-Tirgoviste C, Gagniuc P A, Gubceac E, Mardare L, Popescu I, Dima S and Militaru M. A 3D map of the islet routes throughout the healthy human pancreas. Sci Rep.; 5:14634 (2015).

Islam M S. The islets of Langerhans. Preface. Adv Exp Med Biol.; 654:vii-viii (2010).

Jain R, Lammert E. Cell-cell interactions in the endocrine pancreas. *Diabetes, obesity & metabolism* 11 Suppl 4, 159-167 (2009).

Jang H K, Kim B S. Modulation of stem cell differentiation with biomaterials. *International journal of stem cells* 3, 80-84 (2010).

Jansson L and Carlsson P O. Graft vascular function after transplantation of pancreatic islets. Diabetologia; 45:749-63 (2002).

Jansson L, Barbu A, Bodin B, Drott C J, Espes D, Gao X, Grapensparr L, Kallskog O, Lau J, Liljeback H, Palm F, Quach M, Sandberg M, Stromberg V, Ullsten S and Carlsson P O. Pancreatic islet blood flow and its measurement. Ups J Med Sci.; 121:81-95 (2016).

Jeffries E M, Nakamura S, Lee K W, Clampffer J, Ijima H and Wang Y. Micropatterning electrospun scaffolds to create intrinsic vascular networks. Macromol Biosci.; 14:1514-20 (2014).

Jennings R E, Berry A A, Strutt J P, Gerrard D T and Hanley N A. Human pancreas development. Development; 142: 3126-37 (2015).

Jennings R E, et al. Development of the human pancreas from foregut to endocrine commitment. *Diabetes* 62, 3514-3522 (2013).

Jiang J, Au M, Lu K, Eshpeter A, Korbutt G, Fisk G and Majumdar A S. Generation of insulin-producing islet-like clusters from human embryonic stem cells. Stem Cells; 25:1940-53 (2007).

Jiang W, et al. In vitro derivation of functional insulin-producing cells from human embryonic stem cells. *Cell Res* 17, 333-344 (2007).

Jin S, Wang X, Wang W and Ye K. Bioinspired 3D Scaffold for Inducing Differentiation of Embryonic Stem Cells". In: E. Jabbari, D. Kim, A. Ghaemmaghami and A. Khademhosseini, eds. Handbook of Biomimetics and Bioinspiration Singapore. World Scientific Publishing Co, Pte, Ltd Toh Tuck Link; 9(3):1241-1256 (2014).

Jin S, Yao H, Krisanarungson P, Haukas A, Ye K. Porous membrane substrates offer better niches to enhance the Wnt signaling and promote human embryonic stem cell growth and differentiation. *Tissue Eng Part A* 18, 1419-1430 (2012).

Jin S, Yao H, Weber J L, Melkoumian Z K, Ye K. A synthetic, xeno-free peptide surface for expansion and directed differentiation of human induced pluripotent stem cells. *PLoS One* 7, e50880 (2012).

Jin S. Regeneration of Islet β-cells from stem cells and progenitors. Journal of Stem Cell Research and Transplantation; 1(1):4-8 (2014).

Justin A W, Brooks R A and Markaki A E. Multi-casting approach for vascular networks in cellularized hydrogels. J R Soc Interface; 13 (2016).

Kang H W, Lee S J, Ko I K, Kengla C, Yoo J J and Atala A. A 3D bioprinting system to produce human-scale tissue constructs with structural integrity. Nat Biotechnol.; 34:312-9 (2016).

Kasimir M T, et al. Comparison of different decellularization procedures of porcine heart valves. *Int J Artif Organs* 26, 421-427 (2003).

Kaufman-Francis K, Koffler J, Weinberg N, Dor Y and Levenberg S. Engineered vascular beds provide key signals to pancreatic hormone-producing cells. PLoS One.; 7:e40741 (2012).

Kibbey M C. Maintenance of the EHS sarcoma and Matrigel preparation. *Journal of tissue culture methods* 16, 227-230 (1994).

Kim A, Miller K, Jo J, Kilimnik G, Wojcik P, Hara M. Islet architecture: A comparative study. Islets 1, 129-136 (2009).

Kim Y, Kim H, Ko U H, Oh Y, Lim A, Sohn J W, Shin J H, Kim H and Han Y M. Islet-like organoids derived from human pluripotent stem cells efficiently function in the glucose responsiveness in vitro and in vivo. Sci Rep.; 6:35145 (2016).

Kim, Youngjin, Hyeongseok Kim, Ung Hyun Ko, Youjin Oh, Ajin Lim, Jong-Woo Sohn, Jennifer H. Shin, Hail Kim, and Yong-Mahn Han. "Islet-like organoids derived from human pluripotent stem cells efficiently function in the glucose responsiveness in vitro and in vivo." Scientific reports 6:35145 (2016).

Kolesky D B, Homan K A, Skylar-Scott M A and Lewis J A. Three-dimensional bioprinting of thick vascularized tissues. Proc Natl Acad Sci USA; 113:3179-84 (2016).

Kondo Y, Toyoda T, Inagaki N and Osafune K. iPSC technology-based regenerative therapy for diabetes. J Diabetes Investig. (2017).

Lammert E, Cleaver O and Melton D. Induction of pancreatic differentiation by signals from blood vessels. Science; 294:564-7 (2001).

Lang R, et al. Three-dimensional culture of hepatocytes on porcine liver tissue-derived extracellular matrix. *Biomaterials* 32, 7042-7052 (2011).

Lee V K, Kim D Y, Ngo H, Lee Y, Seo L, Yoo S S, Vincent P A and Dai G. Creating perfused functional vascular channels using 3D bio-printing technology. Biomaterials; 35:8092-102 (2014).

Lee V K, Lanzi A M, Haygan N, Yoo S S, Vincent P A and Dai G. Generation of Multi-Scale Vascular Network System within 3D Hydrogel using 3D Bio-Printing Technology. Cell Mol Bioeng.; 7:460-472 (2014).

Li Y, Xu C, Ma T. In vitro organogenesis from pluripotent stem cells. *Organogenesis* 10, 159-163 (2014).

Matsuoka T A, Artner I, Henderson E, Means A, Sander M, Stein R. The MafA transcription factor appears to be responsible for tissue-specific expression of insulin. *Proc Natl Acad Sci USA* 101, 2930-2933 (2004).

Merani S, Toso C, Emamaullee J and Shapiro A M. Optimal implantation site for pancreatic islet transplantation. Br J Surg.; 95:1449-61 (2008).

Miller J S, Stevens K R, Yang M T, Baker B M, Nguyen D H, Cohen D M, Toro E, Chen A A, Galie P A, Yu X, Chaturvedi R, Bhatia S N and Chen C S. Rapid casting of patterned vascular networks for perfusable engineered three-dimensional tissues. Nat Mater.; 11:768-74 (2012).

Millman J R, Xie C, Van Dervort A, Gurtler M, Pagliuca F W and Melton D A. Generation of stem cell-derived beta-cells from patients with type 1 diabetes. Nat Commun.; 7:11463 (2016).

Mirmalek-Sani, Sayed-Hadi, Giuseppe Orlando, John P. McQuilling, Rajesh Pareta, David L. Mack, Marcus Salvatori, Alan C. Farney et al. "Porcine pancreas extracellular matrix as a platform for endocrine pancreas bioengineering." Biomaterials 34, no. 22:5488-5495 (2013).

Montazeri L, Hojjati-Emami S, Bonakdar S, Tahamtani Y, Hajizadeh-Saffar E, Noori-Keshtkar M, Najar-Asl M, Ashtiani M K and Baharvand H. Improvement of islet engrafts by enhanced angiogenesis and microparticle-mediated oxygenation. Biomaterials; 89:157-65 (2016).

Munoz-Pinto D J, Jimenez-Vergara A C, Gharat T P and Hahn M S. Characterization of sequential collagen-poly (ethylene glycol) diacrylate interpenetrating networks and initial assessment of their potential for vascular tissue engineering. Biomaterials; 40:32-42 (2015).

Nair G, Hebrok M. Islet formation in mice and men: lessons for the generation of functional insulin-producing beta-cells from human pluripotent stem cells. *Curr Opin Genet Dev* 32, 171-180 (2015).

Napierala, H., K-H. Hillebrandt, N. Haep, P. Tang, M. Tintemann, J. Gassner, M. Noesser et al. "Engineering an endocrine Neo-Pancreas by repopulation of a decellularized rat pancreas with islets of Langerhans." Scientific reports 7:41777 (2017).

Narayanan, Karthikeyan, Vivian Y. Lim, Jiayi Shen, Zhen Wei Tan, Divya Rajendran, Shyh-Chyang Luo, Shujun Gao, Andrew C A Wan, and Jackie Y. Ying. "Extracellular matrix-mediated differentiation of human embryonic stem cells: differentiation to insulin-secreting beta cells." Tissue Engineering Part A 20, no. 1-2:424-433 (2013).

Otonkoski, Timo, Gillian M. Beattie, Martin I. Mally, Camillo Ricordi, and Alberto Hayek. "Nicotinamide is a potent inducer of endocrine differentiation in cultured human fetal pancreatic cells." Journal of Clinical Investigation 92, no. 3:1459 (1993).

Pagliuca, Felicia W., Jeffrey R. Millman, Mads Gürtler, Michael Segel, Alana Van Dervort, Jennifer Hyoje Ryu, Quinn P. Peterson, Dale Greiner, and Douglas A. Melton. "Generation of functional human pancreatic β cells in vitro." Cell 159, no. 2:428-439 (2014).

Pan F C, Brissova M. Pancreas development in humans. *Curr Opin Endocrinol Diabetes Obes* 21, 77-82 (2014).

Peloso, Andrea, Luca Urbani, Paolo Cravedi, Ravi Katari, Panagiotis Maghsoudlou, Mario Enrique Alvarez Fallas, Valeria Sordi et al. "The human pancreas as a source of protolerogenic extracellular matrix scaffold for a new-generation bioartificial endocrine pancreas." Annals of surgery 264, no. 1:169-179 (2016).

Pepper A R, Gala-Lopez B, Pawlick R, Merani S, Kin T and Shapiro A M. A prevascularized subcutaneous device-less site for islet and cellular transplantation. Nat Biotechnol.; 33:518-23 (2015).

Perry L, Flugelman M Y and Levenberg S. Elderly Patient-Derived Endothelial Cells for Vascularization of Engineered Muscle. Mol Ther.; 25:935-948 (2017).

Poornejad N, et al. Efficient decellularization of whole porcine kidneys improves reseeded cell behavior. *Biomed Mater* 11, 025003 (2016).

Poornejad N, et al. The impact of decellularization agents on renal tissue extracellular matrix. *J Biomater Appl* 31, 521-533 (2016).

Raikwar S P, Kim E M, Sivitz W I, Allamargot C, Thedens D R, Zavazava N. Human iPS cell-derived insulin producing cells form vascularized organoids under the kidney capsules of diabetic mice. PLoS One 10, e0116582 (2015).

Rajaei B, Shamsara M, Massumi M, Sanati M H. Pancreatic Endoderm-Derived from Diabetic Patient-Specific Induced Pluripotent Stem Cell Generates Glucose-Responsive Insulin-Secreting Cells. *J Cell Physiol*, (2016).

Rana, Deepti, Hala Zreiqat, Nadia Benkirane-Jessel, Seeram Ramakrishna, and Murugan Ramalingam. "Development of decellularized scaffolds for stem cell-driven tissue engineering." Journal of tissue engineering and regenerative medicine 11, no. 4:942-965 (2017).

Reinert R B, Cai Q, Hong J Y, Plank J L, Aamodt K, Prasad N, Aramandla R, Dai C, Levy S E, Pozzi A, Labosky P A, Wright C V, Brissova M and Powers A C. Vascular endothelial growth factor coordinates islet innervation via vascular scaffolding. Development; 141:1480-91 (2014).

Rezania A, Bruin J E, Arora P, Rubin A, Batushansky I, Asadi A, O'Dwyer S, Quiskamp N, Mojibian M, Albrecht T, Yang Y H, Johnson J D and Kieffer T J. Reversal of diabetes with insulin-producing cells derived in vitro from human pluripotent stem cells. Nat Biotechnol.; 32:1121-33 (2014).

Rezania A, Bruin J E, Xu J, Narayan K, Fox J K, O'Neil J J and Kieffer T J. Enrichment of human embryonic stem cell-derived NKX6.1-expressing pancreatic progenitor cells accelerates the maturation of insulin-secreting cells in vivo. Stem Cells; 31:2432-42 (2013).

Rorsman P, Braun M. Regulation of insulin secretion in human pancreatic islets. Annu Rev Physiol 75, 155-179 (2013).

Rose S D, Swift G H, Peyton M J, Hammer R E, MacDonald R J. The role of PTF1-P48 in pancreatic acinar gene expression. J Biol Chem 276, 44018-44026 (2001).

Russ H A, Parent A V, Ringler J J, Hennings T G, Nair G G, Shveygert M, Guo T, Puri S, Haataja L, Cirulli V, Blelloch R, Szot G L, Aryan P and Hebrok M. Controlled induction of human pancreatic progenitors produces functional beta-like cells in vitro. EMBO J 34, 1759-1772 (2015).

Sabetkish, Shabnam, Abdol-Mohammad Kajbafzadeh, Nastaran Sabetkish, Reza Khorramirouz, Aram Akbarzadeh, Sanam Ladi Seyedian, Parvin Pasalar et al. "Whole-organ tissue engineering: Decellularization and recellularization of three-dimensional matrix liver scaffolds." Journal of Biomedical Materials Research Part A 103, no. 4:1498-1508 (2015).

Sachlos E, Reis N, Ainsley C, Derby B and Czernuszka J T. Novel collagen scaffolds with predefined internal morphology made by solid freeform fabrication. Biomaterials.; 24:1487-97 (2003).

Salvatori, Marcus, Ravi Katari, Timil Patel, Andrea Peloso, Jon Mugweru, Kofi Owusu, and Giuseppe Orlando. "Extracellular matrix scaffold technology for bioartificial pancreas engineering: state of the art and future challenges." Journal of diabetes science and technology 8, no. 1:159-169 (2014).

Sato Y, Endo H, Okuyama H, Takeda T, Iwahashi H, Imagawa A, Yamagata K, Shimomura I and Inoue M. Cellular hypoxia of pancreatic beta-cells due to high levels of oxygen consumption for insulin secretion in vitro. J Biol Chem.; 286:12524-32 (2011).

Seymour P A, Sander M. Historical perspective: beginnings of the beta-cell: current perspectives in beta-cell development. Diabetes 60, 364-376 (2011).

Shaer A, Azarpira N, Karimi M H. Differentiation of human induced pluripotent stem cells into insulin-like cell clusters with miR-186 and miR-375 by using chemical transfection. Appl Biochem Biotechnol 174, 242-258 (2014).

Shaer A, Azarpira N, Vandati A, Karimi M H, Shariati M. Differentiation of human-induced pluripotent stem cells into insulin-producing clusters. Exp Clin Transplant 13, 68-75 (2015).

Shi Y, Glaser K J, Venkatesh S K, Ben-Abraham E I and Ehman R L. Feasibility of using 3D M R elastography to determine pancreatic stiffness in healthy volunteers. J Magn Reson Imaging.; 41:369-75 (2015).

Shih H P, Wang A, Sander M. Pancreas organogenesis: from lineage determination to morphogenesis. Annu Rev Cell Dev Biol 29, 81-105 (2013).

Shim J H, Kim J, Han J, An S Y, Jang Y J, Son J, Woo D H, Kim S K and Kim J H. Pancreatic Islet-Like Three-Dimensional Aggregates Derived From Human Embryonic Stem Cells Ameliorate Hyperglycemia in Streptozotocin-Induced Diabetic Mice. Cell Transplant 24, 2155-2168 (2015).

Song W, An D, Kao D I, Lu Y C, Dai G, Chen S and Ma M. Nanofibrous microposts and microwells of controlled shapes and their hybridization with hydrogels for cell encapsulation. ACS Appl Mater Interfaces; 6:7038-44 (2014).

Song W, Lu Y C, Frankel A S, An D, Schwartz R E and Ma M. Engraftment of human induced pluripotent stem cell-derived hepatocytes in immunocompetent mice via 3D co-aggregation and encapsulation. Sci Rep.; 5:16884 (2015).

Song, Jeremy J., and Harald C. Ott. "Organ engineering based on decellularized matrix scaffolds." Trends in molecular medicine 17, no. 8:424-432 (2011).

Stefan Y, Orci L, Malaisse-Lagae F, Perrelet A, Patel Y, Unger R H. Quantitation of endocrine cell content in the pancreas of nondiabetic and diabetic humans. Diabetes 31, 694-700 (1982).

Steiner D J, Kim A, Miller K, Hara M. Pancreatic islet plasticity: interspecies comparison of islet architecture and composition. Islets 2, 135-145 (2010).

Stendahl, John C., Dixon B. Kaufman, and Samuel I. Stupp. "Extracellular matrix in pancreatic islets: relevance to scaffold design and transplantation." Cell transplantation 18, no. 1:1-12 (2009).

Swisa A, Glaser B and Dor Y. Metabolic Stress and Compromised Identity of Pancreatic Beta Cells. Front Genet.; 8:21 (2017).

Takeuchi H, Nakatsuji N, Suemori H. Endodermal differentiation of human pluripotent stem cells to insulin-producing cells in 3D culture. Sci Rep 4, 4488 (2014).

Tapias, Luis F., and Harald C. Ott. "Decellularized scaffolds as a platform for bioengineered organs." Current opinion in organ transplantation 19, no. 2:145 (2014).

Tateishi K, He J, Taranova O, Liang G, D'Alessio A C, Zhang Y. Generation of insulin-secreting islet-like clusters from human skin fibroblasts. J Biol Chem 283, 31601-31607 (2008).

Tuch et al. Scaffolds for islets and stem cells differentiated into insulin-secreting cells. Front Biosci (Landmark Ed), 19:126-38 (2014).

Vegas A J, Veiseh O, Gurtler M, Millman J R, Pagliuca F W, Bader A R, Doloff J C, Li J, Chen M, Olejnik K, Tam H H, Jhunjhunwala S, Langan E, Aresta-Dasilva S, Gandham S, McGarrigle J J, Bochenek M A, Hollister-Lock J, Oberholzer J, Greiner D L, Weir G C, Melton D A, Langer R and Anderson D G. Long-term glycemic control using polymer-encapsulated human stem cell-derived beta cells in immune-competent mice. Nat Med 22, 306-311 (2016).

Veiseh O, Doloff J C, Ma M, Vegas A J, Tam H H, Bader A R, Li J, Langan E, Wyckoff J, Loo W S, Jhunjhunwala S, Chiu A, Siebert S, Tang K, Hollister-Lock J, Aresta-Dasilva S, Bochenek M, Mendoza-Elias J, Wang Y, Qi M, Lavin D M, Chen M, Dholakia N, Thakrar R, Lacik I, Weir G C, Oberholzer J, Greiner D L, Langer R and Anderson D G. Size- and shape-dependent foreign body immune response to materials implanted in rodents and non-human primates. Nat Mater.; 14:643-51 (2015).

Vorotnikova E, et al. Extracellular matrix-derived products modulate endothelial and progenitor cell migration and proliferation in vitro and stimulate regenerative healing in vivo. Matrix Biol 29, 690-700 (2010).

Wang X, Ye K. Three-dimensional differentiation of embryonic stem cells into islet-like insulin-producing clusters. Tissue Eng Part A 15, 1941-1952 (2009).

Wang Y C, Gallego-Arteche E, Iezza G, Yuan X, Math M R, Choo S P, Zuraek M B, Gogia R, Lynn F C, German M S, Bergsland E K, Donner D B, Warren R S and Nakakura E K. Homeodomain transcription factor NKX2.2 functions in immature cells to control enteroendocrine differentiation and is expressed in gastrointestinal neuroendocrine tumors. Endocr Relat Cancer; 16:267-79 (2009).

Wang, Weiwei, Sha Jin, and Kaiming Ye. "Development of Islet Organoids from H9 Human Embryonic Stem Cells in Biomimetic 3D Scaffolds." Stem cells and development 26, no. 6:394-404 (2017).

Wen Y, Jin S. Production of neural stem cells from human pluripotent stem cells. *J Biotechnol* 188, 122-129 (2014).

Wilding L and Gannon M. The role of pdx1 and HNF6 in proliferation and differentiation of endocrine precursors. Diabetes Metab Res Rev.; 20:114-23 (2004).

Wong D Y, Ranganath T and Kasko A M. Low-Dose, Long-Wave U V Light Does Not Affect Gene Expression of Human Mesenchymal Stem Cells. PLoS One.; 10:e0139307 (2015).

Wu D, et al. 3D Culture of MIN-6 Cells on Decellularized Pancreatic Scaffold: In Vitro and In Vivo Study. *BioMed research international* 2015, 432645 (2015).

Wu W, DeConinck A and Lewis J A. Omnidirectional printing of 3D microvascular networks. Adv Mater.; 23:H178-83 (2011).

Yamaguchi T, Sato H, Kato-Itoh M, Goto T, Hara H, Sanbo M, Mizuno N, Kobayashi T, Yanagida A, Umino A, Ota Y, Hamanaka S, Masaki H, Rashid S T, Hirabayashi M and Nakauchi H. Interspecies organogenesis generates autologous functional islets. Nature; 542:191-196 (2017).

Ye K, Jin S and Schultz J S. Genetically engineered fluorescent cell marker for labeling CD34+ hematopoietic stem cells. Biotechnol Prog.; 20:561-5 (2004).

Ye M, Sanchez H M, Hultz M, Yang Z, Bogorad M, Wong A D and Searson P C. Brain microvascular endothelial cells resist elongation due to curvature and shear stress. Sci Rep.; 4:4681 (2014).

Yesmin, S., M. B. Paget, H. E. Murray, and R. Downing. "Bio-scaffolds in organ-regeneration: Clinical potential and current challenges." Current Research in Translational Medicine (2017).

Yu, Yaling, Ali Alkhawaji, Yuqiang Ding, and Jin Mei. "Decellularized scaffolds in regenerative medicine." Oncotarget 7, no. 36:58671 (2016).

Zhang B, Jin S, Jin J, Li F and Montelaro R C. A tumor necrosis factor receptor family protein serves as a cellular receptor for the macrophage-tropic equine lentivirus. Proc Natl Acad Sci USA; 102:9918-23 (2005).

Zhang D, Jiang W, Liu M, Sui X, Yin X, Chen S, Shi Y and Deng H. Highly efficient differentiation of human ES cells and iPS cells into mature pancreatic insulin-producing cells. Cell Res.; 19:429-38 (2009).

Zhang, C, T. Moriguchi, M. Kajihara, R. Esaki, A. Harada, H. Shimohata, H. Oishi, M. Hamada, N. Morito, K. Hasegawa, T. Kudo, J. D. Engel, M. Yamamoto, S. Takahashi, MafA is a key regulator of glucose-stimulated insulin secretion, Mol Cell Biol 25(12):4969-76 (2005).

Zhao X, Liu L, Wang J, Xu Y, Zhang W, Khang G and Wang X. In vitro vascularization of a combined system based on a 3D printing technique. J Tissue Eng Regen Med.; 10:833-842 (2016).

Zhou, Pengcheng, Yibing Guo, Yan Huang, Mingyan Zhu, Xiangjun Fan, Lei Wang, Yao Wang et al. "The dynamic three-dimensional culture of islet-like clusters in decellularized liver scaffolds." Cell and tissue research 365, no. 1:157-171 (2016).

Zhu S, Russ H A, Wang X, Zhang M, Ma T, Xu T, Tang S, Hebrok M and Ding S. Human pancreatic beta-like cells converted from fibroblasts. Nat Commun.; 7:10080 (2016).

What is claimed is:

1. A synthetic pancreatic organoid, comprising:
at least one cross-linked collagen-containing surface, coated with osmotically processed acellular tissue-specific matrix extracted from a mammalian organ without use of detergent, and cell growth factors comprising collagen, mucopolysaccharides, and basement membrane factors; and
stem cells cultured and induced into differentiation on the surface, having at least two differentiated pancreatic cell types.

2. The synthetic pancreatic organoid according to claim 1, wherein the osmotically processed acellular tissue-specific matrix comprises a pancreas tissue-specific matrix, and
wherein the at least two differentiated pancreatic cell types comprise:
about 50-70% pancreatic beta cells,
about 20-30% pancreatic alpha cells,
about 10% pancreatic delta cells, and
less than 5% pancreatic polypeptide cells.

3. The synthetic pancreatic organoid according to claim 2, wherein the pancreatic beta cells, pancreatic alpha cells, pancreatic delta cells, and pancreatic polypeptide cells are derived from human pluripotent stem cells.

4. The synthetic pancreatic organoid according to claim 3, wherein the pancreas tissue-specific matrix is derived from a non-human mammal.

5. The synthetic pancreatic organoid according to claim 1, wherein the acellular tissue-specific matrix is osmotically processed for cellular removal by cycles of different osmotic tension.

6. The synthetic pancreatic organoid according to claim 1, wherein the acellular tissue-specific matrix has a residual DNA content of less than 1% of the DNA of the tissue from which it is derived.

7. A synthetic pancreatic organoid, comprising:
a cross-linked collagen-containing surface,
a coating on the cross-linked collagen-containing surface, comprising an osmotically processed acellular tissue-specific matrix, extracted from a mammalian pancreas, and cell growth factors comprising collagen, mucopolysaccharides, and basement membrane factors, and
a plurality of differentiated pancreatic cell types, derived from stem cells cultured and induced into differentiation on the surface.

8. The synthetic pancreatic organoid according to claim 7, wherein the plurality of differentiated cell types are induced to differentiate by a process comprising sequentially incubating the stem cells in:
RPMI 1640 containing B27, 50 ng/ml activin A and 0.5-1 mM sodium butyrate,
RPMI 1640 containing B27, 250 µM ascorbic acid, 50 ng/ml keratinocyte growth factor, 50 ng/ml Noggin, 1 µM retinoic acid, 300 nM (−)-indolactam V, and 100 nM LDN193189,
DME/F12 containing B27, 1 µM RA, 200 nM LDN, 300 nM ILV, 1 µM 3,3′,5-Triiodo-L-thyronine sodium salt, 10 µM ALK5 inhibitor II, and 10 µg/ml heparin, supplemented with glucose to a final concentration of 20 mM,
RPMI 1640 containing B27, 1 µM T3, 10 µM ALKi, 1 mM N-acetyl cysteine, 0.5 µM R428, 10 µM trolox, 100 nM γ-secretase inhibitor XX, 10 µM zinc sulfate, 10 mM nicotinamide, and 10 µg/ml HP, supplemented with glucose to a final concentration of 20 mM glucose, and
CMRL supplement containing 10% fetal bovine serum, 1 µM T3, 10 µM ALKi, 0.5 µM R428, and 10 mM Nic.

* * * * *